United States Patent
Ko et al.

(10) Patent No.: US 11,618,890 B2
(45) Date of Patent: Apr. 4, 2023

(54) BETA-KETOACYL-ACP SYNTHASE II VARIANTS

(71) Applicant: CORBION BIOTECH, INC., South San Francisco, CA (US)

(72) Inventors: Nien-Hsi Ko, South San Francisco, CA (US); Joshua Ferreira, South San Francisco, CA (US); Janice Lau Wee, South San Francisco, CA (US); William E. Maffe, South San Francisco, CA (US); Douglas A. Hattendorf, South San Francisco, CA (US)

(73) Assignee: Corbion Biotech, Inc., South San Francisco, CA (US)

( * ) Notice: Subject to any disclaimer, the term of this patent is extended or adjusted under 35 U.S.C. 154(b) by 154 days.

(21) Appl. No.: 17/270,141

(22) PCT Filed: Aug. 21, 2019

(86) PCT No.: PCT/US2019/047575
§ 371 (c)(1),
(2) Date: Feb. 22, 2021

(87) PCT Pub. No.: WO2020/041521
PCT Pub. Date: Feb. 27, 2020

(65) Prior Publication Data
US 2021/0246434 A1  Aug. 12, 2021

Related U.S. Application Data

(60) Provisional application No. 62/721,397, filed on Aug. 22, 2018.

(51) Int. Cl.
*C12N 9/10* (2006.01)
*C12P 7/6463* (2022.01)
*C12N 1/13* (2006.01)

(52) U.S. Cl.
CPC .......... *C12N 9/1029* (2013.01); *C12P 7/6463* (2013.01); *C12Y 203/01179* (2013.01)

(58) Field of Classification Search
None
See application file for complete search history.

(56) References Cited

U.S. PATENT DOCUMENTS

| | | |
|---|---|---|
| 5,298,421 A | 3/1994 | Davies et al. |
| 5,304,481 A | 4/1994 | Davies et al. |
| 5,344,771 A | 9/1994 | Davies et al. |
| 5,455,167 A | 10/1995 | Voelker et al. |
| 5,512,482 A | 4/1996 | Voelker et al. |
| 5,639,790 A | 6/1997 | Voelker et al. |
| 5,654,495 A | 8/1997 | Voelker et al. |
| 5,667,997 A | 9/1997 | Voelker et al. |
| 5,723,761 A | 3/1998 | Voelker et al. |
| 5,807,893 A | 9/1998 | Voelker et al. |
| 5,850,022 A | 12/1998 | Dehesh et al. |
| 7,135,290 B2 | 11/2006 | Dillon |
| 8,846,352 B2 | 9/2014 | Chua et al. |
| 8,945,908 B2 * | 2/2015 | Franklin ............... C12P 7/6445 435/189 |
| 9,328,351 B2 | 5/2016 | Franklin et al. |
| 9,512,447 B2 * | 12/2016 | Shankar ................ C07C 31/125 |
| 9,649,368 B2 | 5/2017 | Franklin et al. |
| 10,066,248 B2 * | 9/2018 | Sugihara ................... C12P 7/64 |
| 2012/0283460 A1 | 11/2012 | Franklin et al. |
| 2012/0288930 A1 | 11/2012 | Trimbur et al. |
| 2014/0178950 A1 | 6/2014 | Franklin et al. |
| 2016/0090576 A1 * | 3/2016 | Garg .................... C12N 9/1029 435/15 |

FOREIGN PATENT DOCUMENTS

| | | |
|---|---|---|
| WO | WO 2008/151149 A2 | 12/2008 |
| WO | WO 2010/063032 A2 | 6/2010 |
| WO | WO 2010/120939 A2 | 10/2010 |
| WO | WO 2011/150410 A2 | 12/2011 |
| WO | WO 2011/150411 A1 | 12/2011 |
| WO | WO 2012/106560 A1 | 8/2012 |
| WO | WO 2018/067849 A2 | 4/2018 |

OTHER PUBLICATIONS

Vai et al., Re-engineering ketoacyl synthase specificity, Structure 8, 2000, 565-66. (Year: 2000).*
International Search Report and Written Opinion in International Application No. PCT/US2019/047575, dated Oct. 12, 2019.
Uniprot Database, "Beta-ketoacyl-[acyl-carrier-protein] synthase I," EBI Accession No. V4UP54 (Jun. 20, 2018).
Perez-Vich et al., "Molecular basis of the high-palmitic acid trait in sunflower seed oil," Molecular Breeding, 36(4): 1-12 (2016).
Miao et al., "Biodiesel production from heterotrophic microalgal oil," Bioresource Technology, 97(6): 841-846 (2006).
NCBI Reference Sequence: XP_006447681.1, "3-oxoacyl-[acyl-carrier-protein] synthase, mitochondrial [Citrus clementina]," (Feb. 26, 2018).

* cited by examiner

*Primary Examiner* — Robert B Mondesi
*Assistant Examiner* — Todd M Epstein
(74) *Attorney, Agent, or Firm* — Leydig, Voit & Mayer

(57) ABSTRACT

Provided are non-natural or variant beta-ketoacyl-acyl carrier protein (ACP) synthase (KAS) II enzymes (KASII), polynucleotides encoding such variant KASII, host cells expressing such variant KASII, oils and oil products produced by such cells, and methods of making and using such variant KASII.

22 Claims, No Drawings
Specification includes a Sequence Listing.

SEQUENCE LISTING

```
<160> NUMBER OF SEQ ID NOS: 25

<210> SEQ ID NO 1
<211> LENGTH: 491
<212> TYPE: PRT
<213> ORGANISM: Artificial Sequence
<220> FEATURE:
<223> OTHER INFORMATION: P. moriformis PmKASII enzyme

<400> SEQUENCE: 1

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ala Ala Ala Asp Ala Asn Pro Ala Arg
        35                  40                  45

Pro Glu Arg Arg Val Val Ile Thr Gly Gln Gly Val Val Thr Ser Leu
    50                  55                  60

Gly Gln Thr Ile Glu Gln Phe Tyr Ser Ser Leu Leu Glu Gly Val Ser
65                  70                  75                  80

Gly Ile Ser Gln Ile Gln Lys Phe Asp Thr Thr Gly Tyr Thr Thr Thr
                85                  90                  95

Ile Ala Gly Glu Ile Lys Ser Leu Gln Leu Asp Pro Tyr Val Pro Lys
            100                 105                 110

Arg Trp Ala Lys Arg Val Asp Asp Val Ile Lys Tyr Val Tyr Ile Ala
        115                 120                 125

Gly Lys Gln Ala Leu Glu Ser Ala Gly Leu Pro Ile Glu Ala Ala Gly
    130                 135                 140

Leu Ala Gly Ala Gly Leu Asp Pro Ala Leu Cys Gly Val Leu Ile Gly
145                 150                 155                 160

Thr Ala Met Ala Gly Met Thr Ser Phe Ala Ala Gly Val Glu Ala Leu
                165                 170                 175

Thr Arg Gly Gly Val Arg Lys Met Asn Pro Phe Cys Ile Pro Phe Ser
            180                 185                 190

Ile Ser Asn Met Gly Gly Ala Met Leu Ala Met Asp Ile Gly Phe Met
        195                 200                 205

Gly Pro Asn Tyr Ser Ile Ser Thr Ala Cys Ala Thr Gly Asn Tyr Cys
    210                 215                 220

Ile Leu Gly Ala Ala Asp His Ile Arg Arg Gly Asp Ala Asn Val Met
225                 230                 235                 240

Leu Ala Gly Gly Ala Asp Ala Ala Ile Ile Pro Ser Gly Ile Gly Gly
                245                 250                 255

Phe Ile Ala Cys Lys Ala Leu Ser Lys Arg Asn Asp Glu Pro Glu Arg
            260                 265                 270

Ala Ser Arg Pro Trp Asp Ala Asp Arg Asp Gly Phe Val Met Gly Glu
        275                 280                 285

Gly Ala Gly Val Leu Val Leu Glu Glu Leu Glu His Ala Lys Arg Arg
    290                 295                 300

Gly Ala Thr Ile Leu Ala Glu Leu Val Gly Gly Ala Ala Thr Ser Asp
305                 310                 315                 320

Ala His His Met Thr Glu Pro Asp Pro Gln Gly Arg Gly Val Arg Leu
                325                 330                 335
```

```
Cys Leu Glu Arg Ala Leu Glu Arg Ala Arg Leu Ala Pro Glu Arg Val
            340                 345                 350

Gly Tyr Val Asn Ala His Gly Thr Ser Thr Pro Ala Gly Asp Val Ala
            355                 360                 365

Glu Tyr Arg Ala Ile Arg Ala Val Ile Pro Gln Asp Ser Leu Arg Ile
    370                 375                 380

Asn Ser Thr Lys Ser Met Ile Gly His Leu Leu Gly Ala Gly Ala
385                 390                 395                 400

Val Glu Ala Val Ala Ala Ile Gln Ala Leu Arg Thr Gly Trp Leu His
            405                 410                 415

Pro Asn Leu Asn Leu Glu Asn Pro Ala Pro Gly Val Asp Pro Val Val
            420                 425                 430

Leu Val Gly Pro Arg Lys Glu Arg Ala Glu Asp Leu Asp Val Val Leu
            435                 440                 445

Ser Asn Ser Phe Gly Phe Gly Gly His Asn Ser Cys Val Ile Phe Arg
    450                 455                 460

Lys Tyr Asp Glu Met Asp Tyr Lys Asp His Asp Gly Asp Tyr Lys Asp
465                 470                 475                 480

His Asp Ile Asp Tyr Lys Asp Asp Asp Lys
            485                 490

<210> SEQ ID NO 2
<211> LENGTH: 491
<212> TYPE: PRT
<213> ORGANISM: Artificial Sequence
<220> FEATURE:
<223> OTHER INFORMATION: P. moriformis PmKASII A162X enzyme
<220> FEATURE:
<221> NAME/KEY: misc_feature
<222> LOCATION: (162)..(162)
<223> OTHER INFORMATION: Xaa can be any naturally occurring amino acid

<400> SEQUENCE: 2

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ala Ala Ala Asp Ala Asn Pro Ala Arg
            35                  40                  45

Pro Glu Arg Arg Val Val Ile Thr Gly Gln Gly Val Val Thr Ser Leu
    50                  55                  60

Gly Gln Thr Ile Glu Gln Phe Tyr Ser Ser Leu Leu Glu Gly Val Ser
65                  70                  75                  80

Gly Ile Ser Gln Ile Gln Lys Phe Asp Thr Thr Gly Tyr Thr Thr
                85                  90                  95

Ile Ala Gly Glu Ile Lys Ser Leu Gln Leu Asp Pro Tyr Val Pro Lys
            100                 105                 110

Arg Trp Ala Lys Arg Val Asp Asp Val Ile Lys Tyr Val Tyr Ile Ala
            115                 120                 125

Gly Lys Gln Ala Leu Glu Ser Ala Gly Leu Pro Ile Glu Ala Ala Gly
    130                 135                 140

Leu Ala Gly Ala Gly Leu Asp Pro Ala Leu Cys Gly Val Leu Ile Gly
145                 150                 155                 160

Thr Xaa Met Ala Gly Met Thr Ser Phe Ala Ala Gly Val Glu Ala Leu
            165                 170                 175

Thr Arg Gly Gly Val Arg Lys Met Asn Pro Phe Cys Ile Pro Phe Ser
```

```
                180                 185                 190
Ile Ser Asn Met Gly Gly Ala Met Leu Ala Met Asp Ile Gly Phe Met
            195                 200                 205

Gly Pro Asn Tyr Ser Ile Ser Thr Ala Cys Ala Thr Gly Asn Tyr Cys
        210                 215                 220

Ile Leu Gly Ala Ala Asp His Ile Arg Arg Gly Asp Ala Asn Val Met
225                 230                 235                 240

Leu Ala Gly Gly Ala Asp Ala Ala Ile Ile Pro Ser Gly Ile Gly Gly
                245                 250                 255

Phe Ile Ala Cys Lys Ala Leu Ser Lys Arg Asn Asp Glu Pro Glu Arg
            260                 265                 270

Ala Ser Arg Pro Trp Asp Ala Asp Arg Asp Gly Phe Val Met Gly Glu
        275                 280                 285

Gly Ala Gly Val Leu Val Leu Glu Glu Leu Glu His Ala Lys Arg Arg
    290                 295                 300

Gly Ala Thr Ile Leu Ala Glu Leu Val Gly Gly Ala Ala Thr Ser Asp
305                 310                 315                 320

Ala His His Met Thr Glu Pro Asp Pro Gln Gly Arg Gly Val Arg Leu
                325                 330                 335

Cys Leu Glu Arg Ala Leu Glu Arg Ala Arg Leu Ala Pro Glu Arg Val
            340                 345                 350

Gly Tyr Val Asn Ala His Gly Thr Ser Thr Pro Ala Gly Asp Val Ala
        355                 360                 365

Glu Tyr Arg Ala Ile Arg Ala Val Ile Pro Gln Asp Ser Leu Arg Ile
    370                 375                 380

Asn Ser Thr Lys Ser Met Ile Gly His Leu Leu Gly Gly Ala Gly Ala
385                 390                 395                 400

Val Glu Ala Val Ala Ala Ile Gln Ala Leu Arg Thr Gly Trp Leu His
                405                 410                 415

Pro Asn Leu Asn Leu Glu Asn Pro Ala Pro Gly Val Asp Pro Val Val
            420                 425                 430

Leu Val Gly Pro Arg Lys Glu Arg Ala Glu Asp Leu Asp Val Val Leu
        435                 440                 445

Ser Asn Ser Phe Gly Phe Gly Gly His Asn Ser Cys Val Ile Phe Arg
    450                 455                 460

Lys Tyr Asp Glu Met Asp Tyr Lys Asp His Asp Gly Asp Tyr Lys Asp
465                 470                 475                 480

His Asp Ile Asp Tyr Lys Asp Asp Asp Lys
                485                 490

<210> SEQ ID NO 3
<211> LENGTH: 9271
<212> TYPE: DNA
<213> ORGANISM: Artificial Sequence
<220> FEATURE:
<223> OTHER INFORMATION: pSZ6256

<400> SEQUENCE: 3
agcggaagag cgcccaatgt ttaaacagcc cgcaccctcg ttgatctggg agccctgcgc      60
agccccttaa atcatctcag tcaggtttct gtgttcaact gagcctaaag ggctttcgtc     120
atgcgcacga gcacacgtat atcggccacg cagtttctca aaagcggtag aacagttcgc     180
gagccctcgt aggtcgaaaa cttgcgccag tactattaaa ttaaattaat tgatcgaacg     240
agacgcgaaa cttttgcaga atgccaccga gtttgcccag agaatgggag tggcgccatt     300
```

-continued

```
caccatccgc ctgtgcccgg cttgattcgc cgagacgatg gacggcgaga ccagggagcg      360
gcttgcgagc cccgagccgg tagcaggaac aatgatcgac aatcttcctg tccaattact      420
ggcaaccatt agaaagagcc ggagcgcgtt gaaagtctgc aatcgagtaa ttttcgata       480 cgtcgggcct gctgaaccct aaggctccgg actttgttta aggcgatcca agatgcacgc      540
ggccccaggc acgtatctca agcacaaacc ccagccttag tttcgagact tgggagata      600 gcgaccgata tctagtttgg cattttgtat attaattacc tcaagcaatg gagcgctctg     660
atgcggtgca gcgtcggctg cagcacctgg cagtggcgct agggtcgccc tatcgctcgg     720
aacctggtca gctggctccc gcctcctgct cagcctcttc cggtacccctt tcttgcgcta    780 tgacacttcc agcaaaaggt agggcgggct gcgagacggc ttcccggcgc tgcatgcaac     840
accgatgatg cttcgacccc ccgaagctcc ttcggggctg catgggcgct ccgatgccgc     900
tccagggcga gcgctgttta aatagccagg cccccgattg caaagacatt atagcgagct     960
accaaagcca tattcaaaca cctagatcac taccacttct acacaggcca ctcgagcttg    1020
tgatcgcact ccgctaaggg ggcgcctctt cctcttcgtt tcagtcacaa cccgcaaact    1080
ctagaatatc aatgctgctg caggccttcc tgttcctgct ggccggcttc gccgccaaga    1140
tcagcgcctc catgacgaac gagacgtccg accgccccct ggtgcacttc accccaaca    1200 agggctggat gaacgacccc aacggcctgt ggtacgacga aaggacgcc aagtggcacc     1260 tgtacttcca gtacaacccg aacgacaccg tctggggac gcccttgttc tggggccacg    1320
ccacgtccga cgacctgacc aactgggagg accagcccat cgccatcgcc ccgaagcgca    1380
acgactccgg cgccttctcc ggctccatgg tggtggacta caacaacacc tccggcttct    1440
tcaacgacac catcgacccg cgccagcgct gcgtggccat ctggacctac aacaccccgg    1500
agtccgagga gcagtacatc tcctacagcc tggacggcgg ctacaccttc accgagtacc    1560
agaagaaccc cgtgctggcc gccaactcca cccagttccg cgacccgaag gtcttctggt    1620
acgagccctc ccagaagtgg atcatgaccg cggccaagtc ccaggactac aagatcgaga    1680
tctactcctc cgacgacctg aagtcctgga gctggagtc cgcgttcgcc aacgagggct    1740
tcctcggcta ccagtacgag tgccccggcc tgatcgaggt ccccaccgag caggacccca    1800
gcaagtccta ctgggtgatg ttcatctcca tcaaccccgg cgccccggcc ggcggctcct    1860
tcaaccagta cttcgtcggc agcttcaacg gcacccactt cgaggccttc gacaaccagt    1920
cccgcgtggt ggacttcggc aaggactact acgccctgca gaccttcttc aacaccgacc    1980
cgacctacgg gagcgccctg ggcatcgcgt gggcctccaa ctgggagtac tccgccttcg    2040
tgcccaccaa ccccctggcgc tcctccatgt ccctcgtgcg caagttctcc ctcaacaccg    2100
agtaccaggc caacccggag acggagctga tcaacctgaa ggccgagccg atcctgaaca    2160
tcagcaacgc cggccccctgg agccggttcg ccaccaacac cacgttgacg aaggccaaca    2220
gctacaacgt cgacctgtcc aacagcaccg gcacccctgga gttcgagctg gtgtacgccg    2280
tcaacaccac ccagacgatc tccaagtccg tgttcgcgga cctctcccctc tggttcaagg    2340 gcctggagga ccccgaggag tacctccgca tgggcttcga ggtgtccgcg tcctccttct    2400
tcctggaccg cgggaacagc aaggtgaagt tcgtgaagga aaccccctac ttcaccaacc    2460
gcatgagcgt gaacaaccag cccttcaaga gcgagaacga cctgtcctac tacaaggtgt    2520
acggcttgct ggaccagaac atcctggagc tgtacttcaa cgacggcgac gtcgtgtcca    2580
ccaacaccta cttcatgacc accgggaacg ccctgggctc cgtgaacatg acgacggggg    2640 tggacaaacct gttctacatc gacaagttcc aggtgcgcga ggtcaagtga caattgacgc    2700
```

```
ccgcgcggcg cacctgacct gttctctcga gggcgcctgt tctgccttgc gaaacaagcc    2760
cctggagcat gcgtgcatga tcgtctctgg cgccccgccg cgcggtttgt cgccctcgcg    2820
ggcgccgcgg ccgcgggggc gcattgaaat tgttgcaaac cccacctgac agattgaggg    2880
cccaggcagg aaggcgttga gatggaggta caggagtcaa gtaactgaaa gtttttatga    2940
taactaacaa caaagggtcg tttctggcca gcgaatgaca agaacaagat tccacatttc    3000
cgtgtagagg cttgccatcg aatgtgagcg ggcgggccgc ggacccgaca aaacccttac    3060
gacgtggtaa gaaaaacgtg gcgggcactg tccctgtagc ctgaagacca gcaggagacg    3120
atcggaagca tcacagcaca ggatcccgcg tctcgaacag agcgcgcaga ggaacgctga    3180
aggtctcgcc tctgtcgcac ctcagcgcgg catacaccac aataaccacc tgacgaatgc    3240
gcttggttct tcgtccatta gcgaagcgtc cggttcacac acgtgccacg ttggcgaggt    3300
ggcaggtgac aatgatcggt ggagctgatg gtcgaaacgt tcacagccta gggaattcgg    3360
gagcagttgc tcgaccgccc gcgtcccgca ggcagcgatg acgtgtgcgt ggcctgggtg    3420
tttcgtcgaa aggccagcaa ccctaaatcg caggcgatcc ggagattggg atctgatccg    3480
agtttggacc agatccgccc cgatgcggca cgggaactgc atcgactcgg cgcggaaccc    3540
agctttcgta aatgccagat tggtgtccga tacctggatt tgccatcagc gaaacaagac    3600
ttcagcagcg agcgtatttg gcgggcgtgc taccagggtt gcatacattg cccatttctg    3660
tctggaccgc tttactggcg cagagggtga gttgatgggg ttggcaggca tcgaaacgcg    3720
cgtgcatggt gtgcgtgtct gttttcggct gcacgaattc aatagtcgga tgggcgacgg    3780
tagaattggg tgtggcgctc gcgtgcatgc ctcgccccgt cgggtgtcat gaccgggact    3840
ggaatccccc ctcgcgacca tcttgctaac gctcccgact ctcccgaccg cgcgcaggat    3900
agactcttgt tcaaccaatc gacaactagt gcaggcatgg ccaccgcatc cactttctcg    3960
gcgttcaatg cccgctgcgg cgacctgcgt cgctcggcgg gctccgggcc ccggcgccca    4020
gcgaggcccc tccccgtgcg cgggcgcgcc gccgccgccg ccgacgccaa ccccgcccgc    4080
cccgagcgcc gcgtggtgat caccggccag ggcgtggtga cctccctggg ccagaccatc    4140
gagcagttct actcctccct gctggagggc gtgtccggca tctcccagat ccagaagttc    4200
gacaccaccg gctacaccac caccatcgcc ggcgagatca gtccctgca gctggacccc    4260 tacgtgccca gcgctgggc caagcgcgtg gacgacgtga tcaagtacgt gtacatcgcc    4320
ggcaagcagg ccctggagtc cgccggcctg cccatcgagg ccgccggcct ggccggcgcc    4380
ggcctggacc ccgccctgtg cggcgtgctg atcggcaccg tcatggccgg catgacctcc    4440
ttcgccgccg gcgtggaggc cctgacccgc ggcggcgtgc gcaagatgaa ccccttctgc    4500 atcccctct ccatctccaa catgggcggc gccatgctgg ccatggacat cggcttcatg    4560
ggccccaact actccatctc caccgcctgc gccaccggca actactgcat cctgggcgcc    4620
gccgaccaca tccgccgcgg cgacgccaac gtgatgctgg ccggcggcgc cgacgccgcc    4680
atcatcccct ccggcatcgg cggcttcatc gcctgcaagg ccctgtccaa gcgcaacgac    4740
gagcccgagc gcgcctcccg cccctgggac gccgaccgcg acggcttcgt gatgggcgag    4800
ggcgccggcg tgctggtgct ggaggagctg agcacgcca agcgccgcgg cgccaccatc    4860
ctggccgagc tggtgggcgg cgccgccacc tccgacgccc accacatgac cgagcccgac    4920
ccccagggcc gcgcgtgcg cctgtgcctg agcgcgccc tggagcgcgc ccgcctggcc    4980
cccgagcgcg tgggctacgt gaacgcccac ggcacttcca ccccgccgg cgacgtggcc    5040
```

```
gagtaccgcg ccatccgcgc cgtgatcccc caggactccc tgcgcatcaa ctccaccaag    5100
tccatgatcg gccacctgct gggcggcgcc ggcgccgtgg aggccgtggc cgccatccag    5160
gccctgcgca ccggctggct gcaccccaac ctgaacctgg agaacccggc gccgggcgtg    5220
gaccccgtgg tgctggtggg ccccgcaag gagcgcgccg aggacctgga cgtggtgctg    5280
tccaactcct tcggcttcgg cggccacaac tcctgcgtga tcttccgcaa gtacgacgag    5340
atggactaca aggaccacga cggcgactac aaggaccacg acatcgacta caaggacgac    5400
gacgacaagt gattaattaa atgtggagat gtagggtggt cgactcgttg gaggtgggtg    5460
ttttttttta tcgagtgcgc ggcgcggcaa acgggtccct ttttatcgag gtgttcccaa    5520
cgccgcaccg ccctcttaaa acaacccca ccaccacttg tcgaccttct cgtttgttat    5580
ccgccacggc gccccggagg ggcgtcgtct ggccgcgcgg gcagctgtat cgccgcgctc    5640
gctccaatgg tgtgtaatct tggaaagata ataatcgatg gatgaggagg agagcgtggg    5700
agatcagagc aaggaatata cagttggcac gaagcagcag cgtactaagc tgtagcgtgt    5760
taagaaagaa aaactcgctg ttaggctgta ttaatcaagg agcgtatcaa taattaccga    5820
ccctatacct ttatctccaa cccaatcgcg ggagctcagc gtctgcgtgt tgggagctgg    5880
agtcgtgggc ttgacgacgg cgctgcagct gttgcaggat gtgcctggcg tgcgcgttca    5940
cgtcgtggct gagaaatatg gcgacgaaac gttgacggct ggggccggcg ggctgtggat    6000
gccatacgca ttgggtacgc ggccattgga tgggattgat aggcttatgg agggataata    6060 gagttttgc cggatccaac gcatgtggat gcggtatccc ggtgggctga agtgtggaa     6120 ggatagtgca ttggctattc acatgcactg cccacccctt ttggcaggaa atgtgccggc    6180
atcgttggtg caccgatggg gaaaatcgac gttcgaccac tacatgaaga tttatacgtc    6240
tgaagatgca gcgactgcgg gtgcgaaacg gatgacggtt tggtcgtgta tgtcacagca    6300
tgtgctggat cttgcgggct aactccccct gccacggccc attgcaggtg tcatgttgac    6360
tggagggtac gaccttccgt ccgtcaaatt cccagaggag gacccgctct gggccgacat    6420
tgtgcccact gaagagcgtt taaaccgcct ctccccgcgc gttggccgat tcattaatgc    6480
agctggcacg acaggtttcc cgactggaaa gcgggcagtg agcgcaacgc aattaatgtg    6540
agttagctca ctcattaggc accccaggct ttacactttt atgcttccggc tcgtatgttg    6600 tgtggaattg tgagcggata caatttcac acaggaaaca gctatgacca tgattacgcc    6660
aagctcgaaa ttaaccctca ctaaagggaa caaaagctgg ccaattcgcc ctatagtgag    6720
tcgtattaca attcactggc cgtcgtttta acaacgtcgtg actgggaaaa ccctggcgtt    6780
acccaactta atcgccttgc agcacatccc cctttcgcca gctggcgtaa tagcgaagag    6840
gcccgcaccg atcgcccttc ccaacagttg cgcagcctga atggcgaatg ggacgcgccc    6900
tgtagcggcg cattaagcgc ggcgggtgtg tggttacgc gcagcgtgac cgctacactt    6960
gccagcgccc tagcgcccgc tcctttcgct ttcttccctt cctttctcgc cacgttcgcc    7020
ggctttcccc gtcaagctct aaatcggggg ctcccttag ggttccgatt tagtgcttta    7080
cggcacctcg accccaaaaa acttgattag ggtgatggtt cacgtagtgg gccatcgccc    7140
tgatagacgt tttttcgccc tttgacgttg gagtccacgt tctttaatag tggactcttg    7200
ttccaaactg gaacaacact caaccctatc tcggtctatt cttttgattt ataagggatt    7260
ttgccgattt cggcctattg gttaaaaaat gagctgattt aacaaaaatt taacgcgaat    7320
tttaacaaaa tattaacgct tacaatttag gtggcacttt cggggaaat gtgcgcggaa    7380 cccctatttg tttatttttc taaatacatt caaatatgta tccgctcatg agacaataac    7440
```

```
cctgataaat gcttcaataa tattgaaaaa ggaagagtat gagtattcaa catttccgtg    7500
tcgcccttat tccctttttt gcggcatttt gccttcctgt ttttgctcac ccagaaacgc    7560
tggtgaaagt aaaagatgct gaagatcagt tgggtgcacg agtgggttac atcgaactgg    7620
atctcaacag cggtaagatc cttgagagtt ttcgccccga agaacgtttt ccaatgatga    7680
gcacttttaa agttctgcta tgtggcgcgg tattatcccg tattgacgcc gggcaagagc    7740
aactcggtcg ccgcatacac tattctcaga atgacttggt tgagtactca ccagtcacag    7800
aaaagcatct tacggatggc atgacagtaa gagaattatg cagtgctgcc ataaccatga    7860
gtgataacac tgcggccaac ttacttctga acgatcgg aggaccgaag gagctaaccg    7920
cttttttgca acatgggg gatcatgtaa ctcgccttga tcgttgggaa ccggagctga    7980
atgaagccat accaaacgac gagcgtgaca ccacgatgcc tgtagcaatg gcaacaacgt    8040
tgcgcaaact attaactggc gaactactta ctctagcttc ccggcaacaa ttaatagact    8100
ggatggaggc ggataaagtt gcaggaccac ttctgcgctc ggcccttccg gctggctggt    8160
ttattgctga taaatctgga gccggtgagc gtgggtctcg cggtatcatt gcagcactgg    8220
ggccagatgg taagccctcc cgtatcgtag ttatctacac gacggggagt caggcaacta    8280
tggatgaacg aaatagacag atcgctgaga taggtgcctc actgattaag cattggtaac    8340
tgtcagacca agtttactca tatatacttt agattgattt aaaacttcat ttttaattta    8400
aaaggatcta ggtgaagatc ctttttgata atctcatgac caaaatccct aacgtgagt    8460 tttcgttcca ctgagcgtca gaccccgtag aaaagatcaa aggatcttct tgagatcctt    8520
tttttctgcg cgtaatctgc tgcttgcaaa caaaaaaacc accgctacca gcggtggttt    8580
gtttgccgga tcaagagcta ccaactcttt ttccgaaggt aactggcttc agcagagcgc    8640
agataccaaa tactgtcctt ctagtgtagc cgtagttagg ccaccacttc aagaactctg    8700
tagcaccgcc tacatacctc gctctgctaa tcctgttacc agtggctgct gccagtggcg    8760
ataagtcgtg tcttaccggg ttggactcaa gacgatagtt accggataag gcgcagcggt    8820
cgggctgaac ggggggttcg tgcacacagc ccagcttgga gcgaacgacc tacaccgaac    8880
tgagatacct acagcgtgag ctatgagaaa gcgccacgct cccgaaggg agaaaggcgg    8940 acaggtatcc ggtaagcggc agggtcggaa caggagagcg cacgagggag cttccagggg    9000
gaaacgcctg gtatctttat agtcctgtcg ggtttcgcca cctctgactt gagcgtcgat    9060
ttttgtgatg ctcgtcaggg gggcggagcc tatggaaaaa cgccagcaac gcggcctttt    9120
tacggttcct ggccttttgc tggccttttg ctcacatgtt ctttcctgcg ttatcccctg    9180
attctgtgga taaccgtatt accgcctttg agtgagctga taccgctcgc cgcagccgaa    9240
cgaccgagcg cagcgagtca gtgagcgagg a                                  9271
```

<210> SEQ ID NO 4
<211> LENGTH: 1476
<212> TYPE: DNA
<213> ORGANISM: Artificial Sequence
<220> FEATURE:
<223> OTHER INFORMATION: pSZ6014

<400> SEQUENCE: 4

```
atggccaccg catccacttt ctcggcgttc aatgcccgct gcggcgacct cgtcgctcg      60 gcgggctccg ggccccggcg cccagcgagg cccctccccg tgcgcgggcg cgccgccgcc     120
gccgccgacg ccaaccccgc ccgccccgag cgccgcgtgg tgatcaccgg ccagggcgtg     180
```

| | |
|---|---|
| gtgacctccc tgggccagac catcgagcag ttctactcct ccctgctgga gggcgtgtcc | 240 |
| ggcatctccc agatccagaa gttcgacacc accggctaca ccaccaccat cgccggcgag | 300 |
| atcaagtccc tgcagctgga ccCctacgtg cccaagcgct gggccaagcg cgtggacgac | 360 |
| gtgatcaagt acgtgtacat cgccggcaag caggccctgg agtccgccgg cctgcccatc | 420 |
| gaggccgccg gcctggccgg cgccggcctg accccgccc tgtgcggcgt gctgatcggc | 480 |
| accgccatgg ccggcatgac ctccttcgcc gccggcgtgg aggccctgac ccgcggcggc | 540 |
| gtgcgcaaga tgaaccccttc tgcatcccc ttctccatct ccaacatggg cggcgccatg | 600 |
| ctggccatgg acatcggctt catgggcccc aactactcca tctccaccgc ctgcgccacc | 660 |
| ggcaactact gcatcctggg cgccgccgac cacatccgcc gcggcgacgc caacgtgatg | 720 |
| ctggccggcg gcgccgacgc cgccatcatc ccctccggca tcggcggctt catcgcctgc | 780 |
| aaggccctgt ccaagcgcaa cgacgagccc gagcgcgcct cccgccctg gacgccgac | 840 |
| cgcgacggct tcgtgatggg cgagggcgcc ggcgtgctgg tgctggagga gctggagcac | 900 |
| gccaagcgcc gcgcgccac catcctggcc gagctggtgg gcgcgccgc cacctccgac | 960 |
| gcccaccaca tgaccgagcc cgaccccag ggccgcggcg tgcgcctgtg cctggagcgc | 1020 |
| gccctggagc gcgcccgcct ggccccgag gcgcgtgggc acgtgaacgc ccacggcacc | 1080 |
| tccacccccg ccggcgacgt ggccgagtac cgcgccatcc gccgcgtgat ccccaggac | 1140 |
| tccctgcgca tcaactccac caagtccatg atcggccacc tgctgggcgg cgccggcgcc | 1200 |
| gtggaggccg tggccgccat ccaggccctg cgcaccggct ggctgcaccc caacctgaac | 1260 |
| ctggagaacc cggcgccggg cgtggacccc gtggtgctgg tgggcccccg caaggagcgc | 1320 |
| gccgaggacc tggacgtggt gctgtccaac tccttcggct tcggcggcca caactcctgc | 1380 |
| gtgatcttcc gcaagtacga cgagatggac tacaaggacc acgacggcga ctacaaggac | 1440 |
| cacgacatcg actacaagga cgacgacgac aagtga | 1476 |

<210> SEQ ID NO 5
<211> LENGTH: 1476
<212> TYPE: DNA
<213> ORGANISM: Artificial Sequence
<220> FEATURE:
<223> OTHER INFORMATION: Part of pSZ6256

<400> SEQUENCE: 5

| | |
|---|---|
| atggccaccg catccacttt ctcggcgttc aatgcccgct gcggcgacct cgtcgctcg | 60 |
| gcgggctccg ggccccggcg cccagcgagg cccctccccg tgcgcgggcg cgccgccgcc | 120 |
| gccgccgacg ccaaccccgc ccgccccgag cgccgcgtgg tgatcaccgg ccagggcgtg | 180 |
| gtgacctccc tgggccagac catcgagcag ttctactcct ccctgctgga gggcgtgtcc | 240 |
| ggcatctccc agatccagaa gttcgacacc accggctaca ccaccaccat cgccggcgag | 300 |
| atcaagtccc tgcagctgga ccCctacgtg cccaagcgct gggccaagcg cgtggacgac | 360 |
| gtgatcaagt acgtgtacat cgccggcaag caggccctgg agtccgccgg cctgcccatc | 420 |
| gaggccgccg gcctggccgg cgccggcctg accccgccc tgtgcggcgt gctgatcggc | 480 |
| accgtcatgg ccggcatgac ctccttcgcc gccggcgtgg aggccctgac ccgcggcggc | 540 |
| gtgcgcaaga tgaaccccttc tgcatcccc ttctccatct ccaacatggg cggcgccatg | 600 |
| ctggccatgg acatcggctt catgggcccc aactactcca tctccaccgc ctgcgccacc | 660 |
| ggcaactact gcatcctggg cgccgccgac cacatccgcc gcggcgacgc caacgtgatg | 720 |
| ctggccggcg gcgccgacgc cgccatcatc ccctccggca tcggcggctt catcgcctgc | 780 |

```
aaggccctgt ccaagcgcaa cgacgagccc gagcgcgcct cccgcccctg ggacgccgac      840
cgcgacggct tcgtgatggg cgagggcgcc ggcgtgctgg tgctggagga gctggagcac      900
gccaagcgcc gcggcgccac catcctggcc gagctggtgg cggcgccgc cacctccgac       960 gcccaccaca tgaccgagcc cgaccccag ggccgcggcg tgcgcctgtg cctggagcgc      1020
gccctggagc gcgcccgcct ggccccgag cgcgtgggct acgtgaacgc ccacggcact      1080 tccaccccg ccggcgacgt ggccgagtac cgcgccatcc gcgccgtgat cccccaggac      1140
tccctgcgca tcaactccac caagtccatg atcggccacc tgctgggcgg cgccggcgcc      1200
gtggaggccg tggccgccat ccaggccctg cgcaccggc ggctgcaccc caacctgaac      1260
ctggagaacc cggcgccggg cgtggacccc gtggtgctgg tgggcccccg caaggagcgc      1320
gccgaggacc tggacgtggt gctgtccaac tccttcggct tcggcggcca caactcctgc      1380
gtgatcttcc gcaagtacga cgagatggac tacaaggacc acgacggcga ctacaaggac      1440
cacgacatcg actacaagga cgacgacgac aagtga                                1476

<210> SEQ ID NO 6
<211> LENGTH: 1476
<212> TYPE: DNA
<213> ORGANISM: Artificial Sequence
<220> FEATURE:
<223> OTHER INFORMATION: P. moriformis KASII A162X enzyme variant with
      the CpSAD1tp transit peptide
<220> FEATURE:
<221> NAME/KEY: misc_feature
<222> LOCATION: (484)..(486)
<223> OTHER INFORMATION: n is a, c, g, or t

<400> SEQUENCE: 6
atggccaccg catccacttt ctcggcgttc aatgcccgct gcggcgacct gcgtcgctcg       60
gcgggctccg ggccccggcg cccagcgagg cccctccccg tgcgcgggcg cgccgccgcc      120
gccgccgacg ccaaccccgc ccgccccgag cgccgcgtgg tgatcaccgg ccagggcgtg      180
gtgacctccc tgggccagac catcgagcag ttctactcct ccctgctgga gggcgtgtcc      240
ggcatctccc agatccagaa gttcgacacc accggctaca ccaccaccat cgccggcgag      300
atcaagtccc tgcagctgga cccctacgtg cccaagcgct gggccaagcg cgtggacgac      360
gtgatcaagt acgtgtacat cgccggcaag caggccctgg agtccgccgg cctgcccatc      420
gaggccgccg gcctggccgg cgccggcctg gaccccgccc tgtgcggcgt gctgatcggc      480
accnnnatgg ccggcatgac ctccttcgcc gccggcgtgg aggccctgac ccgcggcggc      540
gtgcgcaaga tgaacccctt ctgcatcccc ttctccatct ccaacatggg cggcgccatg      600
ctggccatgg acatcggctt catgggcccc aactactcca tctccaccgc ctgcgccacc      660
ggcaactact gcatcctggg cgccgccgac cacatccgcc gcggcgacgc caacgtgatg      720
ctggccggcg gcgccgacgc cgccatcatc ccctccggca tcggcggctt catcgccctg      780
aaggccctgt ccaagcgcaa cgacgagccc gagcgcgcct cccgcccctg ggacgccgac      840
cgcgacggct tcgtgatggg cgagggcgcc ggcgtgctgg tgctggagga gctggagcac      900
gccaagcgcc gcggcgccac catcctggcc gagctggtgg cggcgccgc cacctccgac       960 gcccaccaca tgaccgagcc cgaccccag ggccgcggcg tgcgcctgtg cctggagcgc      1020
gccctggagc gcgcccgcct ggccccgag cgcgtgggct acgtgaacgc ccacggcact      1080 tccaccccg ccggcgacgt ggccgagtac cgcgccatcc gcgccgtgat cccccaggac      1140
tccctgcgca tcaactccac caagtccatg atcggccacc tgctgggcgg cgccggcgcc      1200
```

```
gtggaggccg tggccgccat ccaggccctg cgcaccggct ggctgcaccc caacctgaac      1260
ctggagaacc cggcgccggg cgtggacccc gtggtgctgg tgggcccccg caaggagcgc      1320
gccgaggacc tggacgtggt gctgtccaac tccttcggct tcggcggcca caactcctgc      1380
gtgatcttcc gcaagtacga cgagatggac tacaaggacc acgacggcga ctacaaggac      1440
cacgacatcg actacaagga cgacgacgac aagtga                                1476

<210> SEQ ID NO 7
<211> LENGTH: 38
<212> TYPE: PRT
<213> ORGANISM: Artificial Sequence
<220> FEATURE:
<223> OTHER INFORMATION: native CpSAD1tp transit peptide

<400> SEQUENCE: 7

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala
        35

<210> SEQ ID NO 8
<211> LENGTH: 38
<212> TYPE: PRT
<213> ORGANISM: Artificial Sequence
<220> FEATURE:
<223> OTHER INFORMATION: Modified (with codon bias for improved
      expression in P. moriformis) CpSAD1tp transit peptide

<400> SEQUENCE: 8

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile
        35

<210> SEQ ID NO 9
<211> LENGTH: 114
<212> TYPE: DNA
<213> ORGANISM: Artificial Sequence
<220> FEATURE:
<223> OTHER INFORMATION: native CpSAD1tp transit peptide

<400> SEQUENCE: 9
atggccaccg catccacttt ctcggcgttc aatgcccgct gcggcgacct gcgtcgctcg      60
gcgggctccg gccccggcg cccagcgagg cccctccccg tgcgcgggcg cgcc            114

<210> SEQ ID NO 10
<211> LENGTH: 114
<212> TYPE: DNA
<213> ORGANISM: Artificial Sequence
<220> FEATURE:
<223> OTHER INFORMATION: Modified CpSAD1tp transit peptide with codon
      bias for improved expression in P. moriformis

<400> SEQUENCE: 10
atggccaccg cctccacctt ctccgccttc aacgcccgct gcggcgacct gcgccgctcc      60
gccggctccg gccccgccg cccgccccgc ccctgcccg tgcgcgccgc catc             114
```

<210> SEQ ID NO 11
<211> LENGTH: 330
<212> TYPE: PRT
<213> ORGANISM: Artificial Sequence
<220> FEATURE:
<223> OTHER INFORMATION: Wild-type GmFATA thioesterase

<400> SEQUENCE: 11

| Ile | Pro | Pro | Arg | Ile | Ile | Val | Val | Ser | Ser | Ser | Ser | Lys | Val | Asn |
|---|---|---|---|---|---|---|---|---|---|---|---|---|---|---|
| 1 | | | | 5 | | | | | 10 | | | | | 15 |

| Pro | Leu | Lys | Thr | Glu | Ala | Val | Val | Ser | Ser | Gly | Leu | Ala | Asp | Arg | Leu |
|---|---|---|---|---|---|---|---|---|---|---|---|---|---|---|---|
| | | | 20 | | | | | 25 | | | | | 30 | | |

| Arg | Leu | Gly | Ser | Leu | Thr | Glu | Asp | Gly | Leu | Ser | Tyr | Lys | Glu | Lys | Phe |
|---|---|---|---|---|---|---|---|---|---|---|---|---|---|---|---|
| | | 35 | | | | | 40 | | | | | 45 | | | |

| Ile | Val | Arg | Cys | Tyr | Glu | Val | Gly | Ile | Asn | Lys | Thr | Ala | Thr | Val | Glu |
|---|---|---|---|---|---|---|---|---|---|---|---|---|---|---|---|
| | 50 | | | | | 55 | | | | | 60 | | | | |

| Thr | Ile | Ala | Asn | Leu | Leu | Gln | Glu | Val | Gly | Cys | Asn | His | Ala | Gln | Ser |
|---|---|---|---|---|---|---|---|---|---|---|---|---|---|---|---|
| 65 | | | | | 70 | | | | | 75 | | | | | 80 |

| Val | Gly | Tyr | Ser | Thr | Gly | Gly | Phe | Ser | Thr | Thr | Pro | Thr | Met | Arg | Lys |
|---|---|---|---|---|---|---|---|---|---|---|---|---|---|---|---|
| | | | | 85 | | | | | 90 | | | | | 95 | |

| Leu | Arg | Leu | Ile | Trp | Val | Thr | Ala | Arg | Met | His | Ile | Glu | Ile | Tyr | Lys |
|---|---|---|---|---|---|---|---|---|---|---|---|---|---|---|---|
| | | | 100 | | | | | 105 | | | | | 110 | | |

| Tyr | Pro | Ala | Trp | Ser | Asp | Val | Val | Glu | Ile | Glu | Ser | Trp | Gly | Gln | Gly |
|---|---|---|---|---|---|---|---|---|---|---|---|---|---|---|---|
| | | 115 | | | | | 120 | | | | | 125 | | | |

| Glu | Gly | Lys | Ile | Gly | Thr | Arg | Arg | Asp | Trp | Ile | Leu | Arg | Asp | Tyr | Ala |
|---|---|---|---|---|---|---|---|---|---|---|---|---|---|---|---|
| 130 | | | | | 135 | | | | | 140 | | | | | |

| Thr | Gly | Gln | Val | Ile | Gly | Arg | Ala | Thr | Ser | Lys | Trp | Val | Met | Met | Asn |
|---|---|---|---|---|---|---|---|---|---|---|---|---|---|---|---|
| 145 | | | | | 150 | | | | | 155 | | | | | 160 |

| Gln | Asp | Thr | Arg | Arg | Leu | Gln | Lys | Val | Asp | Val | Asp | Val | Arg | Asp | Glu |
|---|---|---|---|---|---|---|---|---|---|---|---|---|---|---|---|
| | | | | 165 | | | | | 170 | | | | | 175 | |

| Tyr | Leu | Val | His | Cys | Pro | Arg | Glu | Leu | Arg | Leu | Ala | Phe | Pro | Glu | Glu |
|---|---|---|---|---|---|---|---|---|---|---|---|---|---|---|---|
| | | | 180 | | | | | 185 | | | | | 190 | | |

| Asn | Asn | Ser | Ser | Leu | Lys | Lys | Ile | Ser | Lys | Leu | Glu | Asp | Pro | Ser | Gln |
|---|---|---|---|---|---|---|---|---|---|---|---|---|---|---|---|
| | | 195 | | | | | 200 | | | | | 205 | | | |

| Tyr | Ser | Lys | Leu | Gly | Leu | Val | Pro | Arg | Arg | Ala | Asp | Leu | Asp | Met | Asn |
|---|---|---|---|---|---|---|---|---|---|---|---|---|---|---|---|
| | 210 | | | | | 215 | | | | | 220 | | | | |

| Gln | His | Val | Asn | Asn | Val | Thr | Tyr | Ile | Gly | Trp | Val | Leu | Glu | Ser | Met |
|---|---|---|---|---|---|---|---|---|---|---|---|---|---|---|---|
| 225 | | | | | 230 | | | | | 235 | | | | | 240 |

| Pro | Gln | Glu | Ile | Ile | Asp | Thr | His | Glu | Leu | Gln | Thr | Ile | Thr | Leu | Asp |
|---|---|---|---|---|---|---|---|---|---|---|---|---|---|---|---|
| | | | | 245 | | | | | 250 | | | | | 255 | |

| Tyr | Arg | Arg | Glu | Cys | Gln | His | Asp | Asp | Val | Val | Asp | Ser | Leu | Thr | Ser |
|---|---|---|---|---|---|---|---|---|---|---|---|---|---|---|---|
| | | | 260 | | | | | 265 | | | | | 270 | | |

| Pro | Glu | Pro | Ser | Glu | Asp | Ala | Glu | Ala | Val | Phe | Asn | His | Asn | Gly | Thr |
|---|---|---|---|---|---|---|---|---|---|---|---|---|---|---|---|
| | | 275 | | | | | 280 | | | | | 285 | | | |

| Asn | Gly | Ser | Ala | Asn | Val | Ser | Ala | Asn | Asp | His | Gly | Cys | Arg | Asn | Phe |
|---|---|---|---|---|---|---|---|---|---|---|---|---|---|---|---|
| | 290 | | | | | 295 | | | | | 300 | | | | |

| Leu | His | Leu | Leu | Arg | Leu | Ser | Gly | Asn | Gly | Leu | Glu | Ile | Asn | Arg | Gly |
|---|---|---|---|---|---|---|---|---|---|---|---|---|---|---|---|
| 305 | | | | | 310 | | | | | 315 | | | | | 320 |

| Arg | Thr | Glu | Trp | Arg | Lys | Lys | Pro | Thr | Arg |
|---|---|---|---|---|---|---|---|---|---|
| | | | | 325 | | | | | 330 |

<210> SEQ ID NO 12
<211> LENGTH: 9271
<212> TYPE: DNA
<213> ORGANISM: Artificial Sequence
<220> FEATURE:

<223> OTHER INFORMATION: pSZ6014 for the expression of wild-type P.
moriformis KASII (PmKASII)in P. moriformis

<400> SEQUENCE: 12

```
agcggaagag cgcccaatgt ttaaacagcc cgcaccctcg ttgatctggg agccctgcgc      60
agccccttaa atcatctcag tcaggtttct gtgttcaact gagcctaaag ggctttcgtc     120
atgcgcacga gcacacgtat atcggccacg cagtttctca aaagcggtag aacagttcgc     180
gagccctcgt aggtcgaaaa cttgcgccag tactattaaa ttaaattaat tgatcgaacg     240
agacgcgaaa cttttgcaga atgccaccga gtttgcccag agaatgggag tggcgccatt     300
caccatccgc ctgtgcccgg cttgattcgc cgagacgatg gacggcgaga ccagggagcg     360
gcttgcgagc cccgagccgg tagcaggaac aatgatcgac aatcttcctg tccaattact     420
ggcaaccatt agaaagagcc ggagcgcgtt gaaagtctgc aatcgagtaa ttttcgata     480
cgtcgggcct gctgaaccct aaggctccgg actttgttta aggcgatcca agatgcacgc     540
ggccccaggc acgtatctca agcacaaacc ccagccttag tttcgagact ttgggagata     600
gcgaccgata tctagtttgg cattttgtat attaattacc tcaagcaatg gagcgctctg     660
atgcggtgca gcgtcggctg cagcacctgg cagtggcgct agggtcgccc tatcgctcgg     720
aacctggtca gctggctccc gcctcctgct cagcctcttc cggtacccct tcttgcgcta     780
tgacacttcc agcaaaaggt agggcgggct gcgagacggc ttcccggcgc tgcatgcaac     840
accgatgatg cttcgacccc ccgaagctcc ttcggggctg catgggcgct ccgatgccgc     900
tccagggcga gcgctgttta aatagccagg ccccgattg caaagacatt atagcgagct     960
accaaagcca tattcaaaca cctagatcac taccacttct acacaggcca ctcgagcttg    1020
tgatcgcact ccgctaaggg ggcgcctctt cctcttcgtt tcagtcacaa cccgcaaact    1080
ctagaatatc aatgctgctg caggccttcc tgttcctgct ggccggcttc gccgccaaga    1140
tcagcgcctc catgacgaac gagacgtccg accgcccct ggtgcacttc accccccaaca    1200
agggctggat gaacgacccc aacggcctgt ggtacgacga aaggacgcc aagtggcacc    1260
tgtacttcca gtacaacccg aacgacaccg tctggggac gcccttgttc tggggccacg    1320
ccacgtccga cgacctgacc aactgggagg accagcccat cgccatcgcc ccgaagcgca    1380
acgactccgg cgccttctcc ggctccatgg tggtggacta caacaacacc tccggcttct    1440
tcaacgacac catcgacccg cgccagcgct gcgtggccat ctggacctac aacacccccgg    1500
agtccgagga gcagtacatc tcctacagcc tggacggcgg ctacaccttc accgagtacc    1560
agaagaaccc cgtgctggcc gccaactcca cccagttccg cgacccgaag gtcttctggt    1620
acgagccctc ccagaagtgg atcatgaccg cggccaagtc ccaggactac aagatcgaga    1680
tctactcctc cgacgacctg aagtcctgga gctggagtc cgcgttcgcc aacgagggct    1740
tcctcggcta ccagtacgag tgccccggcc tgatcgaggt ccccaccgag caggaccccca    1800
gcaagtccta ctgggtgatg ttcatctcca tcaaccccgg cgccccggcc ggcggctcct    1860
tcaaccagta cttcgtcggc agcttcaacg gcacccactt cgaggccttc gacaaccagt    1920
cccgcgtggt ggacttcggc aaggactact acgccctgca gaccttcttc aacaccgacc    1980
cgacctacgg gagcgccctg ggcatcgcgt gggcctccaa ctgggagtac tccgccttcg    2040
tgcccaccaa cccctggcgc tcctccatgt ccctcgtgcg caagttctcc ctcaacaccg    2100
agtaccaggc caacccggag acggagctga tcaacctgaa ggccgagccg atcctgaaca    2160
tcagcaacgc cggccctgg agccggttcg ccaccaacac cacgttgacg aaggccaaca    2220
```

```
gctacaacgt cgacctgtcc aacagcaccg gcaccctgga gttcgagctg gtgtacgccg   2280
tcaacaccac ccagacgatc tccaagtccg tgttcgcgga cctctccctc tggttcaagg   2340
gcctggagga ccccgaggag tacctccgca tgggcttcga ggtgtccgcg tcctccttct   2400
tcctggaccg cgggaacagc aaggtgaagt tcgtgaagga gaaccccta ttcaccaacc   2460
gcatgagcgt gaacaaccag cccttcaaga gcgagaacga cctgtcctac tacaaggtgt   2520
acggcttgct ggaccagaac atcctggagc tgtacttcaa cgacggcgac gtcgtgtcca   2580
ccaacaccta cttcatgacc accgggaacg ccctgggctc cgtgaacatg acgacggggg   2640
tggacaacct gttctacatc gacaagttcc aggtgcgcga ggtcaagtga caattgacgc   2700
ccgcgcggcg cacctgacct gttctctcga gggcgcctgt tctgccttgc gaaacaagcc   2760
cctggagcat gcgtgcatga tcgtctctgg cgccccgccg cgcggtttgt cgccctcgcg   2820
ggcgccgcgg ccgcgggggc gcattgaaat tgttgcaaac cccacctgac agattgaggg   2880
cccaggcagg aaggcgttga gatggaggta caggagtcaa gtaactgaaa gtttttatga   2940
taactaacaa caaagggtcg tttctggcca gcgaatgaca agaacaagat tccacatttc   3000
cgtgtagagg cttgccatcg aatgtgagcg ggcgggccgc ggacccgaca aaaccccttac  3060
gacgtggtaa gaaaaacgtg gcgggcactg tccctgtagc ctgaagacca gcaggagacg   3120
atcggaagca tcacagcaca ggatcccgcg tctcgaacag agcgcgcaga ggaacgctga   3180
aggtctcgcc tctgtcgcac ctcagcgcgg catacaccac aataaccacc tgacgaatgc   3240
gcttggttct tcgtccatta gcgaagcgtc cggttcacac acgtgccacg ttggcgaggt   3300
ggcaggtgac aatgatcggt ggagctgatg gtcgaaacgt tcacagccta gggaattcgg   3360
gagcagttgc tcgaccgccc gcgtcccgca ggcagcgatg acgtgtgcgt ggcctgggtg   3420
tttcgtcgaa aggccagcaa ccctaaatcg caggcgatcc ggagattggg atctgatccg   3480
agtttggacc agatccgccc cgatgcggca cgggaactgc atcgactcgg cgcggaaccc   3540
agctttcgta aatgccagat tggtgtccga tacctggatt tgccatcagc gaaacaagac   3600
ttcagcagcg agcgtatttg gcgggcgtgc taccagggtt gcatacattg cccatttctg   3660
tctggaccgc tttactggcg cagagggtga gttgatgggg ttggcaggca tcgaaacgcg   3720
cgtgcatggt gtgcgtgtct gttttcggct gcacgaattc aatagtcgga tgggcgacgg   3780
tagaattggg tgtggcgctc gcgtgcatgc ctcgccccgt cgggtgtcat gaccgggact   3840
ggaatccccc ctcgcgacca tcttgctaac gctcccgact ctcccgaccg cgcgcaggat   3900
agactcttgt tcaaccaatc gacaactagt gcaggcatgg ccaccgcatc cactttctcg   3960
gcgttcaatg cccgctgcgg cgacctgcgt cgctcggcgg gctccgggcc ccggcgccca   4020
gcgaggcccc tccccgtgcg cgggcgcgcc gccgccgccg ccgacgccaa ccccgcccgc   4080
cccgagcgcc gcgtggtgat caccggccag ggcgtggtga cctccctggg ccagaccatc   4140
gagcagttct actcctccct gctggagggc gtgtccggca tctcccagat ccagaagttc   4200
gacaccaccg gctacaccac caccatcgcc ggcgagatca agtccctgca gctgaccccc   4260
tacgtgccca gcgcctgggc caagcgcgtg gacgacgtga tcaagtacgt gtacatcgcc   4320
ggcaagcagg ccctggagtc cgccggcctg cccatcgagg ccgccggcct ggccggcgcc   4380
ggcctggacc ccgccctgtg cggcgtgctg atcggcaccg ccatggccgg catgacctcc   4440
ttcgccgccg gcgtggaggc cctgaccgcc ggcggcgtgc gcaagatgaa ccccttctgc   4500
atccccttct ccatctccaa catgggcggc gccatgctgg ccatggacat cggcttcatg   4560
ggccccaact actccatctc caccgcctgc gccaccggca actactgcat cctgggcgcc   4620
```

```
gccgaccaca tccgccgcgg cgacgccaac gtgatgctgg ccggcggcgc cgacgccgcc    4680
atcatcccct ccggcatcgg cggcttcatc gcctgcaagg ccctgtccaa gcgcaacgac    4740
gagcccgagc gcgcctcccg cccctgggac gccgaccgcg acggcttcgt gatgggcgag    4800
ggcgccggcg tgctggtgct ggaggagctg agcacgccca gcgccgcgg cgccaccatc    4860 ctggccgagc tggtgggcgg cgccgccacc tccgacgccc accacatgac cgagcccgac    4920
ccccagggcc gcgcgtgcg cctgtgcctg gagcgcgccc tggagcgcgc cgcctggcc    4980 cccgagcgcg tgggctacgt gaacgcccac ggcacctcca ccccgccgg cgacgtggcc    5040 gagtaccgcg ccatccgcgc cgtgatcccc caggactccc tgcgcatcaa ctccaccaag    5100
tccatgatcg gccacctgct gggcggcgcc ggcgccgtgg aggccgtggc cgccatccag    5160
gccctgcgca ccgctggct gcaccccaac ctgaacctgg agaacccggc gccgggcgtg    5220
gaccccgtgg tgctggtggg ccccccgcaag gagcgcgccg aggacctgga cgtggtgctg    5280
tccaactcct tcggcttcgg cggccacaac tcctgcgtga tcttccgcaa gtacgacgag    5340
atggactaca aggaccacga cggcgactac aaggaccacg acatcgacta caaggacgac    5400
gacgacaagt gattaattaa atgtggagat gtagggtggt cgactcgttg gaggtgggtg    5460 tttttttta tcgagtgcgc ggcgcggcaa acgggtccct ttttatcgag gtgttcccaa    5520
cgccgcaccg ccctcttaaa acaaccccca ccaccacttg tcgaccttct cgtttgttat    5580
ccgccacggc gccccggagg ggcgtcgtct ggccgcgcgg gcagctgtat cgccgcgctc    5640
gctccaatgg tgtgtaatct tggaaagata ataatcgatg gatgaggagg agagcgtggg    5700
agatcagagc aaggaatata cagttggcac gaagcagcag cgtactaagc tgtagcgtgt    5760
taagaaagaa aaactcgctg ttaggctgta ttaatcaagg agcgtatcaa taattaccga    5820
ccctatacct ttatctccaa cccaatcgcg ggagctcagc gtctgcgtgt tgggagctgg    5880
agtcgtgggc ttgacgacgg cgctgcagct gttgcaggat gtgcctggcg tgcgcgttca    5940
cgtcgtggct gagaaatatg gcgacgaaac gttgacggct ggggccggcg ggctgtggat    6000
gccatacgca ttgggtacgc ggccattgga tgggattgat aggcttatgg agggataata    6060 gagttttgc cggatccaac gcatgtggat gcggtatccc ggtgggctga aagtgtggaa    6120
ggatagtgca ttggctattc acatgcactg cccaccccct ttggcaggaa atgtgccggc    6180
atcgttggtg caccgatggg gaaaatcgac gttcgaccac tacatgaaga tttatacgtc    6240
tgaagatgca gcgactgcgg gtgcgaaacg gatgacggtt tggtcgtgta tgtcacagca    6300
tgtgctggat cttgcgggct aactcccct gccacgccc attgcaggtg tcatgttgac    6360
tggagggtac gacctttcgt ccgtcaaatt cccagaggag acccgctct gggccgacat    6420 tgtgcccact gaagagcgtt taaaccgcct ctccccgcgc gttggccgat tcattaatgc    6480
agctggcacg acaggtttcc cgactggaaa gcgggcagtg agcgcaacgc aattaatgtg    6540
agttagctca ctcattaggc accccaggct ttacacttta tgcttccggc tcgtatgttg    6600
tgtggaattg tgagcggata caatttcac acaggaaaca gctatgacca tgattacgcc    6660
aagctcgaaa ttaaccctca ctaaagggaa caaaagctgg ccaattcgcc ctatagtgag    6720
tcgtattaca attcactggc cgtcgtttta caacgtcgtg actgggaaaa ccctggcgtt    6780
acccaactta atcgccttgc agcacatccc cctttcgcca gctggcgtaa tagcgaagag    6840
gcccgcaccg atcgcccttc ccaacagttg cgcagcctga atggcgaatg ggacgcgccc    6900
tgtagcggcg cattaagcgc ggcgggtgtg gtggttacgc gcagcgtgac cgctacactt    6960
```

```
gccagcgccc tagcgcccgc tcctttcgct ttcttcccct cctttctcgc cacgttcgcc    7020
ggctttcccc gtcaagctct aaatcggggg ctccctttag ggttccgatt tagtgcttta    7080
cggcacctcg accccaaaaa acttgattag ggtgatggtt cacgtagtgg gccatcgccc    7140
tgatagacgt ttttcgccc tttgacgttg gagtccacgt tctttaatag tggactcttg    7200
ttccaaactg gaacaacact caaccctatc tcggtctatt cttttgattt ataagggatt    7260
ttgccgattt cggcctattg gttaaaaaat gagctgattt aacaaaaatt taacgcgaat    7320
tttaacaaaa tattaacgct tacaatttag gtggcacttt tcggggaaat gtgcgcggaa    7380
cccctatttg tttattttc taaatacatt caaatatgta tccgctcatg agacaataac    7440
cctgataaat gcttcaataa tattgaaaaa ggaagagtat gagtattcaa catttccgtg    7500
tcgcccttat tcccttttt gcggcatttt gccttcctgt ttttgctcac ccagaaacgc    7560
tggtgaaagt aaaagatgct gaagatcagt tgggtgcacg agtgggttac atcgaactgg    7620
atctcaacag cggtaagatc cttgagagtt ttcgccccga agaacgtttt ccaatgatga    7680
gcactttaa agttctgcta tgtggcgcgg tattatcccg tattgacgcc gggcaagagc    7740
aactcggtcg ccgcatacac tattctcaga atgacttggt tgagtactca ccagtcacag    7800
aaaagcatct tacggatggc atgacagtaa gagaattatg cagtgctgcc ataaccatga    7860
gtgataacac tgcggccaac ttacttctga caacgatcgg aggaccgaag gagctaaccg    7920
cttttttgca acatggggg gatcatgtaa ctcgccttga tcgttgggaa ccggagctga    7980
atgaagccat accaaacgac gagcgtgaca ccacgatgcc tgtagcaatg gcaacaacgt    8040
tgcgcaaact attaactggc gaactactta ctctagcttc ccggcaacaa ttaatagact    8100
ggatggaggc ggataaagtt gcaggaccac ttctgcgctc ggcccttccg gctggctggt    8160
ttattgctga taaatctgga gccggtgagc gtgggtctcg cggtatcatt gcagcactgg    8220
ggccagatgg taagccctcc cgtatcgtag ttatctacac gacggggagt caggcaacta    8280
tggatgaacg aaatagacag atcgctgaga taggtgcctc actgattaag cattggtaac    8340
tgtcagacca agtttactca tatatacttt agattgattt aaaacttcat ttttaattta    8400
aaaggatcta ggtgaagatc ctttttgata atctcatgac caaaatccct taacgtgagt    8460
tttcgttcca ctgagcgtca gaccccgtag aaaagatcaa aggatcttct tgagatcctt    8520
ttttttctgcg cgtaatctgc tgcttgcaaa caaaaaaacc accgctacca gcggtggttt    8580
gtttgccgga tcaagagcta ccaactcttt ttccgaaggt aactggcttc agcagagcgc    8640
agataccaaa tactgtcctt ctagtgtagc cgtagttagg ccaccacttc aagaactctg    8700
tagcaccgcc tacatacctc gctctgctaa tcctgttacc agtggctgct gccagtggcg    8760
ataagtcgtg tcttaccggg ttggactcaa gacgatagtt accggataag gcgcagcggt    8820
cgggctgaac ggggggttcg tgcacacagc ccagcttgga gcgaacgacc tacaccgaac    8880
tgagatacct acagcgtgag ctatgagaaa gcgccacgct tcccgaaggg agaaaggcgg    8940
acaggtatcc ggtaagcggc agggtcggaa caggagagcg cacgagggag cttccagggg    9000
gaaacgcctg gtatctttat agtcctgtcg ggtttcgcca cctctgactt gagcgtcgat    9060
ttttgtgatg ctcgtcaggg gggcggagcc tatggaaaaa cgccagcaac gcggcctttt    9120
tacggttcct ggccttttgc tggccttttg ctcacatgtt ctttcctgcg ttatcccctg    9180
attctgtgga taaccgtatt accgcctttg agtgagctga taccgctcgc cgcagccgaa    9240
cgaccgagcg cagcgagtca gtgagcgagg a                                    9271
```

<210> SEQ ID NO 13
<211> LENGTH: 1476
<212> TYPE: DNA
<213> ORGANISM: Artificial Sequence
<220> FEATURE:
<223> OTHER INFORMATION: P. moriformis KASII (PmKASII) gene variants in constructs pSZ7122 and pSZ7104 to pSZ7121
<220> FEATURE:
<221> NAME/KEY: misc_feature
<222> LOCATION: (484)..(486)
<223> OTHER INFORMATION: n is a, c, g, or t

<400> SEQUENCE: 13

```
atggccaccg catccacttt ctcggcgttc aatgcccgct gcggcgacct gcgtcgctcg      60
gcgggctccg ggccccggcg cccagcgagg cccctccccg tgcgcgggcg cgccgccgcc     120
gccgccgacg ccaaccccgc cgcccccgag cgccgcgtgg tgatcaccgg ccagggcgtg     180
gtgacctccc tgggccagac catcgagcag ttctactcct ccctgctgga gggcgtgtcc     240
ggcatctccc agatccagaa gttcgacacc accggctaca ccaccaccat cgccggcgag     300
atcaagtccc tgcagctgga cccctacgtg cccaagcgct gggccaagcg cgtggacgac     360
gtgatcaagt acgtgtacat cgccggcaag caggccctgg agtccgccgg cctgcccatc     420
gaggccgccg gcctggccgg cgccggcctg daccccgccc tgtgcggcgt gctgatcggc     480
accnnnatgg ccggcatgac ctccttcgcc gccggcgtgg aggccctgac ccgcggcggc     540
gtgcgcaaga tgaaccccctt ctgcatcccc ttctccatct ccaacatggg cggcgccatg     600
ctggccatgg acatcggctt catgggcccc aactactcca tctccaccgc ctgcgccacc     660
ggcaactact gcatcctggg cgccgccgac cacatccgcc gcggcgacgc caacgtgatg     720
ctggccggcg gcgccgacgc cgccatcatc ccctccggca tcggcggctt catcgcctgc     780
aaggccctgt ccaagcgcaa cgacgagccc gagcgcgcct cccgcccctg ggacgccgac     840
cgcgacggct tcgtgatggg cgagggcgcc ggcgtgctgg tgctggagga gctggagcac     900
gccaagcgcc gcggcgccac catcctggcc gagctggtgg gcggcgccgc cacctccgac     960
gcccaccaca tgaccgagcc cgaccccccag ggccgcggcg tgcgcctgtg cctggagcgc    1020
gccctggagc gcgcccgcct ggccccccgag cgcgtgggcg acgtgaacgc ccacggcacc    1080
tccacccccg ccggcgacgt ggccgagtac cgcgccatcc gcgccgtgat ccccccaggac    1140
tccctgcgca tcaactccac caagtccatg atcggccacc tgctgggcgg cgccggcgcc    1200
gtggaggccg tggccgccat ccaggccctg cgcaccggct ggctgcaccc caacctgaac    1260
ctggagaacc cggcgccggg cgtggacccc gtggtgctgg tgggcccccg caaggagcgc    1320
gccgaggacc tggacgtggt gctgtccaac tccttcggct tcggcggcca caactcctgc    1380
gtgatcttcc gcaagtacga cgagatggac tacaaggacc acgacggcga ctacaaggac    1440
cacgacatcg actacaagga cgacgacgac aagtga                              1476
```

<210> SEQ ID NO 14
<211> LENGTH: 1476
<212> TYPE: DNA
<213> ORGANISM: Artificial Sequence
<220> FEATURE:
<223> OTHER INFORMATION: P. moriformis KASII (PmKASII) gene variants in constructs pSZ7122 and pSZ7104 to pSZ7121
<220> FEATURE:
<221> NAME/KEY: misc_feature
<222> LOCATION: (484)..(486)
<223> OTHER INFORMATION: n is a, c, g, or t

<400> SEQUENCE: 14

-continued

| | |
|---|---|
| atggccaccg catccacttt ctcggcgttc aatgcccgct gcggcgacct gcgtcgctcg | 60 |
| gcgggctccg ggccccggcg cccagcgagg cccctcccg tgcgcgggcg cgccgccgcc | 120 |
| gccgccgacg ccaaccccgc ccgccccgag cgccgcgtgg tgatcaccgg ccagggcgtg | 180 |
| gtgacctccc tgggccagac catcgagcag ttctactcct ccctgctgga gggcgtgtcc | 240 |
| ggcatctccc agatccagaa gttcgacacc accggctaca ccaccaccat cgccggcgag | 300 |
| atcaagtccc tgcagctgga cccctacgtg cccaagcgct gggccaagcg cgtggacgac | 360 |
| gtgatcaagt acgtgtacat cgccggcaag caggccctgg agtccgccgg cctgcccatc | 420 |
| gaggccgccg gcctggccgg cgccggcctg accccgccc tgtgcggcgt gctgatcggc | 480 |
| accnnnatgg ccggcatgac ctccttcgcc gccggcgtgg aggccctgac ccgcggcggc | 540 |
| gtgcgcaaga tgaacccctt ctgcatcccc ttctccatct ccaacatggg cggcgccatg | 600 |
| ctggccatgg acatcggctt catgggcccc aactactcca tctccaccgc ctgcgccacc | 660 |
| ggcaactact gcatcctggg cgccgccgac cacatccgcc gcggcgacgc caacgtgatg | 720 |
| ctggccggcg gcgccgacgc cgccatcatc ccctccggca tcggcggctt catcgcctgc | 780 |
| aaggccctgt ccaagcgcaa cgacgagccc gagcgcgcct cccgcccctg gacgccgac | 840 |
| cgcgacggct tcgtgatggg cgagggcgcc ggcgtgctgg tgctggagga gctggagcac | 900 |
| gccaagcgcc gcggcgccac catcctggcc gagctggtgg gcggcgccgc cacctccgac | 960 |
| gcccaccaca tgaccgagcc cgaccccag ggccgcggcg tgcgcctgtg cctggagcgc | 1020 |
| gccctggagc gcgcccgcct ggccccgag cgcgtgggct acgtgaacgc ccacggcacc | 1080 |
| tccaccccg ccggcgacgt ggccgagtac cgcgccatcc gcgccgtgat cccccaggac | 1140 |
| tccctgcgca tcaactccac caagtccatg atcggccacc tgctgggcgg cgccggcgcc | 1200 |
| gtggaggccg tggccgccat ccaggccctg cgcaccggct ggctgcaccc caacctgaac | 1260 |
| ctggagaacc cggcgccggg cgtggacccc gtggtgctgg tgggcccccg caaggagcgc | 1320 |
| gccgaggacc tggacgtggt gctgtccaac tccttcggct tcggcggcca caactcctgc | 1380 |
| gtgatcttcc gcaagtacga cgagatggac tacaaggacc acgacggcga ctacaaggac | 1440 |
| cacgacatcg actacaagga cgacgacgac aagtga | 1476 |

<210> SEQ ID NO 15
<211> LENGTH: 38
<212> TYPE: PRT
<213> ORGANISM: Artificial Sequence
<220> FEATURE:
<223> OTHER INFORMATION: Plastid transit peptide

<400> SEQUENCE: 15

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala
        35

<210> SEQ ID NO 16
<211> LENGTH: 13
<212> TYPE: PRT
<213> ORGANISM: Artificial Sequence
<220> FEATURE:
<223> OTHER INFORMATION: Plastid transit peptide

<400> SEQUENCE: 16

```
Ser Gly Pro Arg Arg Pro Ala Arg Pro Leu Pro Val Arg
1               5                   10
```

<210> SEQ ID NO 17
<211> LENGTH: 28
<212> TYPE: PRT
<213> ORGANISM: Artificial Sequence
<220> FEATURE:
<223> OTHER INFORMATION: Plastid transit peptide

<400> SEQUENCE: 17

```
Ser Gly Pro Arg Arg Pro Ala Arg Pro Leu Pro Val Arg Ala Ala Ile
1               5                   10                  15

Ala Ser Glu Val Pro Val Ala Thr Thr Ser Pro Arg
            20                  25
```

<210> SEQ ID NO 18
<211> LENGTH: 12
<212> TYPE: PRT
<213> ORGANISM: Artificial Sequence
<220> FEATURE:
<223> OTHER INFORMATION: Plastid transit peptide

<400> SEQUENCE: 18

```
Arg Pro Ala Arg Pro Leu Pro Val Arg Gly Arg Ala
1               5                   10
```

<210> SEQ ID NO 19
<211> LENGTH: 24
<212> TYPE: PRT
<213> ORGANISM: Artificial Sequence
<220> FEATURE:
<223> OTHER INFORMATION: Plastid transit peptide

<400> SEQUENCE: 19

```
Arg Pro Ala Arg Pro Leu Pro Val Arg Ala Ala Ile Ala Ser Glu Val
1               5                   10                  15

Pro Val Ala Thr Thr Ser Pro Arg
            20
```

<210> SEQ ID NO 20
<211> LENGTH: 26
<212> TYPE: PRT
<213> ORGANISM: Artificial Sequence
<220> FEATURE:
<223> OTHER INFORMATION: Plastid transit peptide

<400> SEQUENCE: 20

```
Arg Cys Gly Asp Leu Arg Arg Ser Ala Gly Ser Gly Pro Arg Arg Pro
1               5                   10                  15

Ala Arg Pro Leu Pro Val Arg Gly Arg Ala
            20                  25
```

<210> SEQ ID NO 21
<211> LENGTH: 38
<212> TYPE: PRT
<213> ORGANISM: Artificial Sequence
<220> FEATURE:
<223> OTHER INFORMATION: Plastid transit peptide

<400> SEQUENCE: 21

```
Arg Cys Gly Asp Leu Arg Arg Ser Ala Gly Ser Gly Pro Arg Arg Pro
1               5                   10                  15

Ala Arg Pro Leu Pro Val Arg Ala Ala Ile Ala Ser Glu Val Pro Val
            20                  25                  30
```

```
Ala Thr Thr Ser Pro Arg
        35

<210> SEQ ID NO 22
<211> LENGTH: 8
<212> TYPE: PRT
<213> ORGANISM: Artificial Sequence
<220> FEATURE:
<223> OTHER INFORMATION: Plastid transit peptide

<400> SEQUENCE: 22

Pro Ala Arg Pro Leu Pro Val Arg
1               5

<210> SEQ ID NO 23
<211> LENGTH: 23
<212> TYPE: PRT
<213> ORGANISM: Artificial Sequence
<220> FEATURE:
<223> OTHER INFORMATION: Plastid transit peptide

<400> SEQUENCE: 23

Pro Ala Arg Pro Leu Pro Val Arg Ala Ala Ile Ala Ser Glu Val Pro
1               5                   10                  15

Val Ala Thr Thr Ser Pro Arg
            20

<210> SEQ ID NO 24
<211> LENGTH: 10
<212> TYPE: PRT
<213> ORGANISM: Artificial Sequence
<220> FEATURE:
<223> OTHER INFORMATION: Plastid transit peptide

<400> SEQUENCE: 24

Arg Arg Pro Ala Arg Pro Leu Pro Val Arg
1               5                   10

<210> SEQ ID NO 25
<211> LENGTH: 25
<212> TYPE: PRT
<213> ORGANISM: Artificial Sequence
<220> FEATURE:
<223> OTHER INFORMATION: Plastid transit peptide

<400> SEQUENCE: 25

Arg Arg Pro Ala Arg Pro Leu Pro Val Arg Ala Ala Ile Ala Ser Glu
1               5                   10                  15

Val Pro Val Ala Thr Thr Ser Pro Arg
            20                  25
```

BETA-KETOACYL-ACP SYNTHASE II VARIANTS

CROSS-REFERENCE TO RELATED APPLICATIONS

This patent application is the U.S. national stage of PCT/US2019/047575, filed Aug. 21, 2019, which claims the benefit of U.S. Provisional Patent Application No. 62/721,397, filed Aug. 22, 2018, each of which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 52,140 Byte ASCII (Text) file named "Sequence Listing.TXT," dated Feb. 17, 2021.

BACKGROUND

The elongation of C14:0 acyl-ACP to C16:0 acyl-ACP or the elongation of C16:0 acyl-ACP to C18:0 acyl-ACP in the fatty acid biosynthetic pathway is catalyzed by the β-ketoacyl-ACP synthase II (KASII). An increase in the rate of this reaction in Prototheca moriformis through over-expression of multiple copies of the endogenous KASII gene (PmKASII) has previously resulted in the production of oils with an increase in long-chain and very long-chain fatty acid content (e.g., C18+C20+C22+C24) and a decrease in medium-chain fatty acid, myristic acid and palmitic acid content (e.g., C8+C10+C12+C14+C16). Here, we report on the ability to achieve a similar shift in oil composition through the use of a more active PmKASII variant identified from an error-prone PCR library.

SUMMARY

In one aspect, provided are polynucleotides encoding a non-natural or variant β-ketoacyl-acyl carrier protein (ACP) synthase (KAS) II enzyme (KASII). In some embodiments, the non-natural KASII comprises at least about 80%, 85%, 90%, 91%, 92%, 93%, 94%, 95%, 96%, 97%, 98% or 99% sequence identity to amino acid residues 39-469 of SEQ ID NO:2 and comprises X at the position corresponding to position 162; wherein X is an amino acid residue selected from the group consisting of cysteine (C), aspartate (D), glutamate (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W) and tyrosine (Y), wherein the positions are with reference to SEQ ID NO:2, and wherein the non-natural KASII catalyzes the elongation of C14 acyl-ACP, e.g., from C14 to C16. In some embodiments, the non-natural KASII comprises at least about 80%, 85%, 90%, 91%, 92%, 93%, 94%, 95%, 96%, 97%, 98% or 99% sequence identity to amino acid residues 39-469 of SEQ ID NO:2 and comprises X at the position corresponding to position 162; wherein X is an amino acid residue selected from the group consisting of cysteine (C), aspartate (D), glutamate (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W) and tyrosine (Y), wherein the positions are with reference to SEQ ID NO:2, and wherein the non-natural KASII catalyzes the elongation of C16 acyl-ACP, e.g., from C16 to C18. In some embodiments, the non-natural KASII comprises at least about 80%, 85%, 90%, 91%, 92%, 93%, 94%, 95%, 96%, 97%, 98% or 99% sequence identity to amino acid residues 1-469 of SEQ ID NO:2 and comprises an X at the position corresponding to position 162; wherein X is an amino acid residue selected from the group consisting of cysteine (C), aspartate (D), glutamate (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W) and tyrosine (Y), wherein the positions are with reference to SEQ ID NO:2, and wherein the non-natural KASII catalyzes the elongation of C14 acyl-ACP, e.g., from C14 to C16. In some embodiments, the non-natural KASII comprises at least about 80%, 85%, 90%, 91%, 92%, 93%, 94%, 95%, 96%, 97%, 98% or 99% sequence identity to amino acid residues 1-469 of SEQ ID NO:2 and comprises an X at the position corresponding to position 162; wherein X is an amino acid residue selected from the group consisting of cysteine (C), aspartate (D), glutamate (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W) and tyrosine (Y), wherein the positions are with reference to SEQ ID NO:2, and wherein the non-natural KASII catalyzes the elongation of C16 acyl-ACP, e.g., from C16 to C18. In some embodiments, the non-natural KASII preferentially produces C18 acyl-ACP, e.g., C18:0 acyl-ACP, C18:1 acyl-ACP and/or C18:2 acyl-ACP. In some embodiments, the non-natural KASII facilitates the production of increased levels of C18, C20, C22, and/or C24 fatty acids in comparison to a wild-type KASII. In some embodiments, non-natural KASII facilitates the production of increased levels of C18:1 fatty acid in comparison to a wild-type KASII. In some embodiments, the X at position 162 is an amino acid residue selected from serine (S), threonine (T), and valine (V). In some embodiments, the amino acid X at position 162 is an amino acid residue selected from isoleucine (I), leucine (L) and valine (V). In some embodiments, the amino acid X at position 162 is a valine (V) residue. In some embodiments, the amino acid X at position 162 is an amino acid residue selected from cysteine (C), glutamate (E), lysine (K), methionine (M), serine (S), tryptophan (W), valine (V), asparagine (N), aspartate (D), glutamine (Q), histidine (H), leucine (L), phenylalanine (F), threonine (T), and tyrosine (Y). In one embodiment, the amino acid X at position 162 is selected from valine (V), asparagine (N), aspartate (D), glutamine (Q), histidine (H), leucine (L), phenylalanine (F), threonine (T), and tyrosine (Y). In some embodiments, the amino acid X at position 162 is valine (V) and the non-natural KASII facilitates a decreased level of C16:0 fatty acids in comparison to a wild-type KASII. In some embodiments, the amino acid X at position 162 is asparagine (N) and the non-natural KASII facilitates a decreased level of C16:0 fatty acids in comparison to a wild-type KASII. In some embodiments, the amino acid X at position 162 is aspartate (D) and the non-natural KASII facilitates a decreased level of C16:0 fatty acids in comparison to a wild-type KASII. In some embodiments, the amino acid X at position 162 is glutamine (Q) and the non-natural KASII facilitates a decreased level of C16:0 fatty acids in comparison to a wild-type KASII. In some embodiments, the amino acid X at position 162 is histidine (H) and the non-natural KASII facilitates a decreased level of C16:0 fatty acids in comparison to a wild-type KASII. In some embodiments, the amino acid X at position 162 is leucine (L) and the non-natural KASII facilitates a decreased level of C16:0 fatty acids in comparison to a wild-type KASII. In some embodiments, the amino acid X at position 162 is phenylalanine (F) and the non-natural KASII facilitates a decreased level of C16:0 fatty acids in comparison to a wild-type KASII. In some embodiments, the amino acid X at position 162 is threonine (T) and the non-natural KASII facilitates a decreased level of C16:0 fatty acids in comparison to a wild-type KASII. In some embodiments, the amino acid X at position 162 is tyrosine (Y) and the non-natural KASII facilitates a decreased level of C16:0 fatty acids in comparison to a wild-type KASII. In some embodiments, the non-natural or variant KASII comprises a plastid transit peptide. In some embodiments, the plastid transit peptide comprises at least about 80%, 85%, 90%, 91%, 92%, 93%, 94%, 95%, 96%, 97%, 98% or 99% identity to SEQ ID NO:7 or SEQ ID NO:8. In some embodiments, the plastid transit peptide is encoded by a polynucleotide comprising at least about 80%, 85%, 90%, 91%, 92%, 93%, 94%, 95%, 96%, 97%, 98% or 99% identity to SEQ ID NO:9 or SEQ ID NO:10. In some embodiments, the polynucleotide comprises at least about 80%, 85%, 90%, 91%, 92%, 93%, 94%, 95%, 96%, 97%, 98% or 99% identity to nucleic acid residues 115-1407 of SEQ ID NO:6. In some embodiments, the polynucleotide comprises at least about 80%, 85%, 90%, 91%, 92%, 93%, 94%, 95%, 96%, 97%, 98% or 99% identity to nucleic acid residues 1-1407 of SEQ ID NO:6. In some embodiments, the polynucleotide comprises at least about 80%, 85%, 90%, 91%, 92%, 93%, 94%, 95%, 96%, 97%, 98% or 99% identity to SEQ ID NO:6. In some embodiments, the polynucleotide comprises a thymine (T) at residue position 1080, the residue position in reference to SEQ ID NO: 6. In some embodiments, the polynucleotide comprises codon bias for improved expression in a microalgal host cell, e.g., a Prototheca or Chlorella microalgal host cell.

In another aspect, provided are expression cassettes comprising a polynucleotide encoding a non-natural or variant β-ketoacyl-acyl carrier protein (ACP) synthase (KAS) II enzyme (KASII), as described above and herein.

In another aspect, provided are vectors comprising the polynucleotide and/or the expression cassettes comprising a polynucleotide encoding a non-natural or variant β-ketoacyl-acyl carrier protein (ACP) synthase (KAS) II enzyme (KASII), as described above and herein. In some embodiments, the vector further comprises a polynucleotide encoding an exogenous lipid biosynthesis enzyme, e.g., fatty acid biosynthesis enzymes and/or triglyceride biosynthesis enzymes. In some embodiments, the thioesterase preferentially hydrolyzes C18 acyl-ACP substrates, e.g., C18:0 acyl-ACP substrates, C18:1 acyl-ACP substrates or C18:2 acyl-ACP substrates. In some embodiments, the thioesterase is from a plant genus selected from Brassica, Carthamus, Camelina, Garcinia, Glycine, Mangifera, Helianthus, Madhura, Arachis, Morus, Ricinus, Herrania, Corchorus, Corchorus, Jatropha, Ziziphus, Trema orientalis, Hevea, Theobroma, Quercus, Cucurbita, Dorcoceras, Rosa, Asparagus, Cephalotus, Parasponia, Carica, Arabidopsis, Capsella and Eutrema. In some embodiments, the thioesterase is from a plant species selected from Brassica napus, Brassica campestris, Brassica juncea, Carthamus tinctorius, Camelina sativa, Garcinia mangostana, Glycine max, Mangifera indica, Helianthus annuus, Madhura longifolia, Arachis hypogaea, Morus notabilis, Ricinus communis, Herrania umbratical, Corchorus olitorius, Corchorus capsularis, Jatropha curcas, Ziziphus jujube, Trema orientalis, Hevea brasiliensis, Theobroma cacao, Quercus suber, Cucurbita maxima, Cucurbita pepo, Cucurbita moschata, Dorcoceras hygrometricum, Rosa chinensis, Asparagus officinalis, Cephalotus follicularis, Parasponia andersonii, Carica papaya, Arabidopsis thaliana, Capsella rubella and Eutrema salsugineum. In some embodiments, the polynucleotide encodes a Garcinia mangostana (GmFATA) thioesterase, optionally comprising one or more amino acid substitutions selected from the group consisting of L91F, L91K, L91S, G96A, G96T, G96V, G108A, G108V, S111A, S111V, T156F, T156A, T156K, T156V and V193A, wherein the amino acid positions are with reference to SEQ ID NO:11.

In a further aspect, provided are non-natural or variant KASII polypeptides encoded by the polynucleotides described above and herein. In some embodiments, the non-natural or variant KASII comprises an amino acid sequence of SEQ ID NO:2. In some embodiments, the non-natural or variant KASII comprises an amino acid sequence of amino acid residues 39-469 of SEQ ID NO:2. In some embodiments, the non-natural or variant KASII comprises an amino acid sequence of SEQ ID NO:2 or an amino acid sequence of amino acid residues 39-469 of SEQ ID NO:2, wherein the amino acid X at position 162 is cysteine (C), glutamate (E), lysine (K), methionine (M), serine (S), tryptophan (W), valine (V), asparagine (N), aspartate (D), glutamine (Q), histidine (H), leucine (L), phenylalanine (F), threonine (T), or tyrosine (Y)

In another aspect, provided are fusion proteins comprising the non-natural or variant KASII polypeptides, as described above and herein, and a heterologous or an exogenous peptide or polypeptide.

In another aspect, provided are microalgal host cells comprising a polynucleotide encoding a non-natural or variant β-ketoacyl-acyl carrier protein (ACP) synthase (KAS) II enzyme (KASII), an expression cassette, and/or a vector, as described above and herein. In some embodiments, the host cell further comprises a polynucleotide encoding a heterologous fatty acyl-ACP thioesterase. In some embodiments, the thioesterase preferentially hydrolyzes C18 acyl-ACP substrates, e.g., C18:0 acyl-ACP substrates, C18:1 acyl-ACP substrates or C18:2 acyl-ACP substrates. In some embodiments, the thioesterase is from a plant genus selected from Brassica, Carthamus, Camelina, Garcinia, Glycine, Mangifera, Helianthus, Madhura, Arachis, Morus, Ricinus, Herrania, Corchorus, Corchorus, Jatropha, Ziziphus, Trema orientalis, Hevea, Theobroma, Quercus, Cucurbita, Dorcoceras, Rosa, Asparagus, Cephalotus, Parasponia, Carica, Arabidopsis, Capsella and Eutrema. In some embodiments, the thioesterase is from a plant species selected from Brassica napus, Brassica campestris, Brassica juncea, Carthamus tinctorius, Camelina sativa, Garcinia mangostana, Glycine max, Mangifera indica, Helianthus annuus, Madhura longifolia, Arachis hypogaea, Morus notabilis, Ricinus communis, Herrania umbratical, Corchorus olitorius, Corchorus capsularis, Jatropha curcas, Ziziphus jujube, Trema orientalis, Hevea brasiliensis, Theobroma cacao, Quercus suber, Cucurbita maxima, Cucurbita pepo, Cucurbita moschata, Dorcoceras hygrometricum, Rosa chinensis, Asparagus officinalis, Cephalotus follicularis, Parasponia andersonii, Carica papaya, Arabidopsis thaliana, Capsella rubella and Eutrema salsugineum. In some embodiments, the thioesterase is a Garcinia mangostana (GmFATA) thioesterase, optionally comprising one or more amino acid substitutions selected from the group consisting of L91F, L91K, L91S, G96A, G96T, G96V, G108A, G108V, S111A, S111V, T156F, T156A, T156K, T156V and V193A, wherein the amino acid positions are with reference to SEQ ID NO:11. In some embodiments, one or more endogenous lipid biosynthesis enzymes (e.g., fatty acid biosynthesis enzymes and/or triglyceride biosynthesis enzymes) are selected from the group consisting of fatty acyl thioesterase A (FATA), a fatty acyl thioesterase B (FATB), fatty acyl desaturases (FADs), including without limitation phosphatidylglycerol desaturase (FAD4), plastidial oleate desaturase (FADE), plastidial linoleate desaturase (FAD7/FAD8), endoplasmic reticulum oleate desaturase (FAD2), endoplasmic reticulum linolate desaturase (FAD3), delta 12 fatty acid desaturase (Δ12 FAD) and the delta 15 fatty acid desaturase (Δ15 FAD), stearoyl-ACP desaturase 2 (SAD2), 1-acylglycerol-3-phosphate O-acyltransferase (LPAAT), glycerol-3-phosphate acyltransferase (GPAT), acyl CoA:diacylglycerol acyltransferase (DGAT), fatty acid elongase (FAE), and long-chain acyl-CoA synthetase (LACS) are deleted, knocked out or knocked down. In some embodiments, the host cell further comprises one or more exogenous or heterologous lipid biosynthesis enzymes, e.g., selected from the group consisting of a fatty acyl thioesterase A (FATA), a fatty acyl thioesterase B (FATB), a fatty acyl desaturase (FAD), including without limitation phosphatidylglycerol desaturase (FAD4), plastidial oleate desaturase (FADE), plastidial linoleate desaturase (FAD7/FAD8), endoplasmic reticulum oleate desaturase (FAD2), endoplasmic reticulum linolate desaturase (FAD3), delta 12 fatty acid desaturase (Δ12 FAD), delta 15 fatty acid desaturase (Δ15 FAD), and stearoyl-ACP desaturase 2 (SAD2); a 1-acylglycerol-3-phosphate O-acyltransferase (LPAAT), a glycerol-3-phosphate acyltransferase (GPAT), an acyl CoA:diacylglycerol acyltransferase (DGAT), a fatty acid and a fatty acid elongase (FAE), and a long-chain acyl-CoA synthetase (LACS). In some embodiments, the host cell further comprises one or more exogenous or heterologous enzymes, such as a sucrose invertase, an alpha galactosidase, and a 4-amino-5-hydroxymethyl-2-methylpyrimidine phosphate synthase (THIC). In some embodiments, the host cell is an oleaginous microbial cell (e.g., oleaginous yeasts, such as *Yarrowia lipolytica*). In some embodiments, the microbial host cell is an oleaginous microalgal cell. In some embodiments, the host cell is a heterotrophic microalga. In some embodiments, the host cell is a microalga of the phylum Chlorpophya. In some embodiments, the host cell is a microalga of the class Trebouxiophytae. In some embodiments, the host cell is a microalga of the order Chlorellales. In some embodiments, the host cell is a microalga of the family Chlorellacae. In some embodiments, the host cell is a microalga cell of the genus *Prototheca* or *Chlorella*. In some embodiments, the microalgal cell is selected from the group consisting of *Prototheca moriformis, Prototheca krugani, Prototheca stagnora, Prototheca zopfii* and *Chlorella protothecoides*. In some embodiments, the host cell has a fatty acid profile comprising at least 40%, 45%, 50%, 55%, 60%, 65%, 70%, 75%, 80%, 85%, 90%, 95%, 97%, or more, C18, C20, C22 and/or C24 fatty acids.

In a further aspect, provided are methods of producing a microalga that produces an oil having a desired fatty acid profile. In some embodiments, the methods comprise transforming a microalgal host cell with a polynucleotide encoding a non-natural or variant 3-ketoacyl-acyl carrier protein (ACP) synthase (KAS) II enzyme (KASII), an expression cassette, and/or a vector, as described above and herein, and cultivating the microalgal host cell so as to produce the oil. In some embodiments, the microalgal host cell produces on oil comprising at least 1%, 2%, 3%, 4%, 5%, 6%, 7%, 8%, 9%, 10%, 20%, 40%, 45%, 50%, 55%, 60%, 65%, 70%, 75%, 80%, 85%, 90%, 95%, 97%, or more, C18 (e.g., C18:0, C18:1 and/or C18:2), C20, C22 and/or C24 fatty acids. In some embodiments, the microalgal host cell produces an oil with an increased C18 (e.g., C18:0, C18:1 and/or C18:2), C20, C22 and/or C24 fatty acid level of at least 1%, 2%, 3%, 4%, 5%, 6%, 7%, 8%, 9%, 10%, 20%, 40%, 50%, 80%, 100%, 200%, or more, in comparison to an untransformed microalga or a microalga transformed with a wild-type KASII. In some embodiments, the microalgal host cell produces an oil with an increased C18:1 fatty acid level of at least 1%, 2%, 3%, 4%, 5%, 6%, 7%, 8%, 9%, 10%, 20%, 40%, 50%, 80%, 100%, 200%, or more, in comparison to an untransformed microalga or a microalga transformed with a wild-type KASII. In some embodiments, the microalgal host cell produces an oil with an increase in C18 (e.g., C18:0, C18:1 and/or C18:2) fatty acid level of at least 2-fold, 3-fold, 4-fold, 5-fold, 6-fold, 7-fold, 8-fold, 9-fold, 10-fold, 11-fold, 12-fold, 13-fold, 14-fold, 15-fold, or more, in comparison to an untransformed microalga or a microalga transformed with a wild-type KASII. In some embodiments, the microalgal host cell produces an oil with an increase in C18, C20, C22, and/or C24 fatty acid level of between 1% and 200%, between 1% and 100%, between 1% and 50%, between 1% and 10%, between 2% and 10%, and/or between 3% and 10%. In some embodiments, the microalgal host cell produces an oil with an increased C18:1 fatty acid level of between 1% and 200%, between 1% and 100%, between 1% and 50%, between 1% and 10%, between 2% and 10%, and/or between 3% and 10%. In some embodiments, the oil is a triglyceride oil. In some embodiments, the method further comprises the step of recovering the oil.

In another aspect, provided are methods of producing an oil comprising predominantly C18 (e.g., C18:0, C18:1 and/or C18:2) fatty acids, comprising transforming a microalgal host cell with a polynucleotide encoding a non-natural or variant β-ketoacyl-acyl carrier protein (ACP) synthase (KAS) II enzyme (KASII), an expression cassette, and/or a vector, as described above and herein, and cultivating the microalgal host cell so as to produce an oil comprising at least about 40% C18 (e.g., C18:0, C18:1 and/or C18:2) fatty acids, e.g., at least about 45%, 50%, 55%, 60%, 65%, 70%, 75%, 80%, 85%, 90%, 95%, 97%, or more, C18 (e.g., C18:0, C18:1 and/or C18:2) fatty acids.

In another aspect, provided are methods for increasing the level of C18 fatty acids and/or the ratio of C18 fatty acids to the sum of other fatty acids (e.g., C8+C10+C12+C14+C16+C20+C22+C24) composing the fatty acid profile of an oil produced by an optionally oleaginous host cell, the method comprising, providing a parent gene encoding a KASII enzyme, mutating the gene so as to encode a non-natural or variant KASII polypeptide as described above and herein; expressing the mutated gene in the host cell; and producing the oil, whereby the level of C18 fatty acids and/or the ratio of C18 fatty acids to the sum of other fatty acids (e.g., C8+C10+C12+C14+C16+C20+C22+C24) composing the fatty acid profile of the oil are increased.

In another aspect, provided are methods for increasing the level of C18, C20, C22 and/or C24 fatty acids and/or the ratio of C18, C20, C22 and/or C24 fatty acids to the sum of other fatty acids composing the fatty acid profile of an oil produced by an optionally oleaginous host cell, the method comprising, providing a parent gene encoding a KASII enzyme, mutating the gene so as to encode a non-natural or variant KASII polypeptide as described above and herein; expressing the mutated gene in the host cell; and producing the oil, whereby the level of C18, C20, C22 and/or C24 fatty acids and/or the ratio of C18, C20, C22 and/or C24 fatty acids to the sum of other fatty acids composing the fatty acid profile of the oil are increased.

With respect to embodiments of the methods, in some embodiments, the methods further comprise co-expressing a polynucleotide encoding a fatty acyl-ACP thioesterase. In some embodiments, the thioesterase preferentially hydrolyzes C18 acyl-ACP substrates. In some embodiments, the thioesterase preferentially hydrolyzes C18:0 acyl-ACP substrates, C18:1 acyl-ACP substrates or C18:2 acyl-ACP substrates. In some embodiments, the thioesterase is from a plant genus selected from *Brassica, Carthamus, Camelina, Garcinia, Glycine, Mangifera, Helianthus, Madhura, Arachis, Morus, Ricinus, Herrania, Corchorus, Corchorus, Jatropha, Ziziphus, Trema orientalis, Hevea, Theobroma, Quercus, Cucurbita, Dorcoceras, Rosa, Asparagus, Cephalotus, Parasponia, Carica, Arabidopsis, Capsella* and *Eutrema*. In some embodiments, the thioesterase is from a plant species selected from *Brassica napus, Brassica campestris, Brassica juncea, Carthamus tinctorius, Camelina sativa, Garcinia mangostana, Glycine max, Mangifera indica, Helianthus annuus, Madhura longifolia, Arachis hypogaea, Morus notabilis, Ricinus communis, Herrania umbratical, Corchorus olitorius, Corchorus capsularis, Jatropha curcas, Ziziphus jujube, Trema orientalis, Hevea brasiliensis, Theobroma cacao, Quercus suber, Cucurbita maxima, Cucurbita pepo, Cucurbita moschata, Dorcoceras hygrometricum, Rosa chinensis, Asparagus officinalis, Cephalotus follicularis, Parasponia andersonii, Carica papaya, Arabidopsis thaliana, Capsella rubella* and *Eutrema salsugineum*. In some embodiments, the thioesterase is a *Garcinia mangostana* (GmFATA) thioesterase, optionally comprising one or more amino acid substitutions selected from the group consisting of L91F, L91K, L91S, G96A, G96T, G96V, G108A, G108V, S111A, S111V, T156F, T156A, T156K, T156V and V193A, wherein the amino acid positions are with reference to SEQ ID NO:11. In some embodiments, the host cell is an oleaginous microbial cell (e.g., oleaginous yeasts, such as *Yarrowia lipolytica*). In some embodiments, the microbial host cell is an oleaginous microalgal cell. In some embodiments, the host cell is a heterotrophic microalga. In some embodiments, the host cell is a microalga of the phylum Chlorpophya. In some embodiments, the host cell is a microalga of the class Trebouxiophytae. In some embodiments, the host cell is a microalga of the order Chlorellales. In some embodiments, the host cell is a microalga of the family Chlorellacae. In some embodiments, the host cell is a microalga cell of the genus *Prototheca* or *Chlorella*. In some embodiments, the microalgal cell is selected from the group consisting of *Prototheca moriformis, Prototheca krugani, Prototheca stagnora, Prototheca zopfii* and *Chlorella protothecoides*.

In another aspect, provided is an oil produced by the methods described above and herein.

Definitions

As used herein, an "acyl-ACP thioesterase," "fatty acyl-ACP thioesterase," "acyl-ACP TE," or "thioesterase" interchangeably refers to an enzyme that catalyzes the cleavage of a fatty acid from an acyl carrier protein (ACP) during lipid biosynthesis. Acyl-acyl carrier protein (ACP) thioesterases (TEs) hydrolyze acyl-ACP thioester bonds, releasing free fatty acids and ACP.

The term "acyl-ACP preferring TE" refers to the fatty acyl-ACP substrate specificity of a TE. An acyl-ACP preferring TE preferentially liberates a particular fatty acid from an acyl-ACP substrate. For example, the acyl-ACP preferring TE can preferentially liberate a given fatty acid (e.g., C8:0 fatty acids) over all other fatty acids in the set of C8:0, C10:0, C12:0, C14:0, C16:0, C18:0, C18:1, and C18:2 fatty acids. The preference of the acyl-ACP preferring TE can be detected as a higher $V_{max}$ (or a higher $k_{cat}$, or a higher V/K) in comparison to other non-preferred fatty acid-ACP substrates. The preference can be inferred from changes in fatty acid profile of a cell genetically engineered to overexpress the acyl-ACP preferring TE relative to a control cell that does not overexpress the acyl-ACP preferring TE.

Numbering of a given amino acid polymer or nucleic acid polymer "corresponds to" or is "relative to" the numbering of a selected amino acid polymer or nucleic acid polymer when the position of any given polymer component (e.g., amino acid, nucleotide, also referred to generically as a "residue") is designated by reference to the same or to an equivalent position (e.g., based on an optimal alignment or a consensus sequence) in the selected amino acid or nucleic acid polymer, rather than by the actual numerical position of the component in the given polymer.

A "variant" is a polypeptide comprising a sequence which differs in one or more amino acid position(s) from that of a parent polypeptide sequence (e.g., by substitution, deletion, or insertion). A variant may comprise a sequence which differs from the parent polypeptides sequence in up to 40% of the total number of residues of the parent polypeptide sequence, such as in up to 40%, 35%, 30%, 25%, 20%, 15%, 10%, 9%, 8%, 7%, 6%, 5%, 4%, 3% 2% or 1% of the total number of residues of the parent polypeptide sequence. For example, a variant of a 400 amino acid polypeptide sequence comprises a sequence which differs in up to 40% of the total number of residues of the parent polypeptide sequence, that is, in up to 160 amino acid positions within the 400 amino acid polypeptide sequence (such as in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 85, 90, 95, 100, 105, 110, 115, 120, 125, 130, 135, 140, 145, 150, 155, or 160 amino acid positions within the reference sequence.

"Naturally occurring" as applied to a composition that can be found in nature as distinct from being artificially produced by man. For example, a polypeptide or polynucleotide that is present in an organism (including viruses, bacteria, protozoa, insects, plants or mammalian tissue) that can be isolated from a source in nature and which has not been intentionally modified by man in the laboratory is naturally occurring. "Non-naturally occurring" (also termed "synthetic" or "artificial") as applied to an object means that the object is not naturally-occurring—i.e., the object cannot be found in nature as distinct from being artificially produced by man.

A "cell oil" or "cell fat" shall mean a predominantly triglyceride oil obtained from an organism, where the oil has not undergone blending with another natural or synthetic oil, or fractionation so as to substantially alter the fatty acid profile of the oil. In connection with an oil comprising triglycerides of a particular regiospecificity, the cell oil or cell fat has not been subjected to interesterification or other synthetic process to obtain that regiospecific triglyceride profile, rather the regiospecificity is produced naturally, by a cell or population of cells. For a cell oil or cell fat produced by a cell, the sterol profile of oil is generally determined by the sterols produced by the cell, not by artificial reconstitution of the oil by adding sterols in order to mimic the cell oil. In connection with a cell oil or cell fat, and as used generally throughout the present disclosure, the terms oil and fat are used interchangeably, except where otherwise noted. Thus, an "oil" or a "fat" can be liquid, solid, or partially solid at room temperature, depending on the makeup of the substance and other conditions. Here, the term "fractionation" means removing material from the oil in a way that changes its fatty acid profile relative to the profile produced by the organism, however accomplished. The terms "cell oil" and "cell fat" encompass such oils obtained from an organism, where the oil has undergone minimal processing, including refining, bleaching and/or degumming, which does not substantially change its triglyceride profile. A cell oil can also be a "noninteresterified cell oil", which means that the cell oil has not undergone a process in which fatty acids have been redistributed in their acyl linkages to glycerol and remain essentially in the same configuration as when recovered from the organism.

The terms "lipid", "neutral lipid", "triglyceride", "triacylglyceride", "triacylglycerol", "TAG", and "triglyceride oil" are used interchangeably in the present disclosure, except where otherwise noted.

"Fatty acids" shall mean free fatty acids, fatty acid salts, or fatty acyl moieties in a glycerolipid. It will be understood that fatty acyl groups of glycerolipids can be described in terms of the carboxylic acid or anion of a carboxylic acid that is produced when the triglyceride is hydrolyzed or saponified.

As used herein, an oil is said to be "enriched" in one or more particular fatty acids if there is at least a 10% increase in the mass of that fatty acid in the oil relative to the non-enriched oil. For example, in the case of a cell expressing a heterologous fatty acyl-ACP thioesterase gene described herein, the oil produced by the cell is said to be enriched in, e.g., C10 fatty acids, if the mass of these fatty acids in the oil is at least 10% greater than in oil produced by a cell of the same type that does not express the heterologous fatty acyl-ACP thioesterase gene (e.g., wild type oil).

A "fatty acid profile" is the distribution of fatty acyl groups in the triglycerides of the oil without reference to attachment to a glycerol backbone. Fatty acid profiles are typically determined by conversion to a fatty acid methyl ester (FAME), followed by gas chromatography (GC) analysis with flame ionization detection (FID). The fatty acid profile can be expressed as one or more percent of a fatty acid in the total fatty acid signal determined from the area under the curve for that fatty acid. FAME-GC-FID measurement approximate weight percentages of the fatty acids.

"Microalgae" are microbial organisms that contain a chloroplast or plastid, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, Volvox, which is a simple multicellular photosynthetic microbe of two distinct cell types. Microalgae include eukaryotic Chlorophyceae such as *Chlorella, Dunaliella*, and *Prototheca*. Microalgae also include other microbial photosynthetic organisms that exhibit cell-cell adhesion, such as *Agmenellum, Anabaena*, and *Pyrobotrys*. Microalgae also include obligate heterotrophic microorganisms that have lost the ability to perform photosynthesis, such as certain dinoflagellate algae species and species of the genus *Prototheca* or *Chlorella*.

An "oleaginous" cell is a non-human cell capable of producing at least 20% lipid by dry cell weight, naturally or through recombinant or classical strain improvement. An "oleaginous microbe" or "oleaginous microorganism" is a microbe, including a microalga that is oleaginous.

As used with respect to polypeptides or polynucleotides, the term "isolated" refers to a polypeptide or polynucleotide that has been separated from at least one other component that is typically present with the polypeptide or polynucleotide. Thus, a naturally occurring polypeptide is isolated if it has been purified away from at least one other component that occurs naturally with the polypeptide or polynucleotide. A recombinant polypeptide or polynucleotide is isolated if it has been purified away from at least one other component present when the polypeptide or polynucleotide is produced.

The terms "polypeptide" and "protein" are used interchangeably herein to refer a polymer of amino acids, and unless otherwise limited, include atypical amino acids that can function in a similar manner to naturally occurring amino acids.

The term "sequence", as used in connection with a polypeptide or nucleic acid polymer refers to the order of monomers making up the polymer or the sub-polymer or fragment having that sequence.

A "subsequence" of an amino acid or nucleotide sequence is a portion of a larger sequence or the peptide or nucleic acid sub-polymer or fragment characterized by the portion of the larger sequence.

The term "percent sequence identity," in the context of two or more amino acid or nucleic acid sequences, refers to two or more sequences or subsequences that are the same or have a specified percentage of amino acid residues or nucleotides that are the same, when compared and aligned for maximum correspondence, as measured using a sequence comparison algorithm or by visual inspection. For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence (e.g., SEQ ID NOs: 1-14), based on the designated program parameters. Optimal alignment of sequences for comparison can be conducted using the NCBI BLAST software (ncbi.nlm.nih.gov/BLAST/) set to default parameters. For example, to compare two nucleic acid sequences, one may use BLASTN program with its default parameters: (General Parameters: Max target sequences: 100; Expect threshold: 10; Word size: 28, Max matches in a query range: 0; Scoring parameters: Match/Mismatch Scores: 1, -2; Gap Costs: linear). For polypeptide sequence alignment and sequence identity calculations, BLASTP program can be used with its default parameters (General Parameters: Max target sequences: 100, Expect threshold: 10; Word size: 6; Max matches in a query range: 0; Scoring Parameters: Matrix=BLOSUM62; Gap costs: Existence=11, Extension=1; Compositional adjustments=Conditional compositional score). In certain embodiments, the sequence identity between two polypeptide sequences is determined using the Needleman-Wunsch algorithm (Needleman and Wunsch, 1970, J. Mol. Biol. 48: 443-453) as implemented in the Needle program of the EMBOSS package (https://www.ebi-.ac.uk/Tools/psa/emboss_needle/) from the European Bioinformatics Institute, using its default parameters (Matrix:

BLOSUM62; Gap Open: 10; Gap Extend: 0.5; End Gap Penalty: false; End Gap Open: 10; End Gap Extend: 0.5). In certain embodiments, the sequence identity between two nucleic acid sequences is determined using the Needleman-Wunsch algorithm described above using its default parameters (Matrix: DNAfull; Gap Open: 10; Gap Extend: 0.5; End Gap Penalty; false; End Gap Open: 10; End Gap Extend: 0.5). In certain embodiments, the sequence alignment of two or more sequences are performed using Clustal Omega or ClustalW using the suggested default parameters (Dealign input sequences: no; Mbed-like clustering guide-tree: yes; Mbed-like clustering iteration: yes; number of combined iterations: default (0); Max guide tree iterations: default; Max HMM iterations: default; Order: aligned).

As used with reference to polypeptides, the term "wild-type" refers to any polypeptide having an amino acid sequence present in a polypeptide from a naturally occurring organism, regardless of the source of the molecule; i.e., the term "wild-type" refers to sequence characteristics, regardless of whether the molecule is purified from a natural source; expressed recombinantly, followed by purification; or synthesized.

The term "mutation" shall mean a change in a protein, polypeptide, or peptide sequence or subsequence produced by altering one or more nucleotides in a nucleotide coding for the protein, polypeptide, or peptide, however the alteration is obtained. For example, a mutation can be produced randomly, by PCR mutation, by synthesis of entire gene, or any other method.

The term "vector" is used herein to describe a DNA construct containing a polynucleotide. Such a vector can be propagated stably or transiently in a host cell. The vector can, for example, be a plasmid, a viral vector, or simply a potential genomic insert. Once introduced into a suitable host, the vector may replicate and function independently of the host genome, or may, in some instances, integrate into the host genome.

As used herein, the terms "expression vector" or "expression construct" or "expression cassette" refer to a nucleic acid construct, generated recombinantly or synthetically, with a series of specified nucleic acid elements that permit transcription of a particular nucleic acid in a host cell. The expression vector can be part of a plasmid, virus, or nucleic acid fragment. An "expression cassette" includes a coding nucleic acid (CDS) to be transcribed operably linked to a promoter and a 3'UTR. Optionally, and in the Examples below, the promoter of an expression cassette is a heterologous promoter.

"Exogenous gene" refers to a nucleic acid transformed into a cell. The exogenous gene may be from a different species (and so heterologous), or from the same species (and so homologous) relative to the cell being transformed. In the case of a homologous gene, it occupies a different location in the genome of the cell relative to the endogenous copy of the gene. The exogenous gene may be present in more than one copy in the cell. The exogenous gene may be maintained in a cell as an insertion into the genome or as an episomal molecule.

The term "heterologous" refers to amino acid subsequences that are not encoded by the naturally occurring gene. This can be accomplished in any way known in the art, including, e.g., swapping of individual domains with an altered and/or non-naturally occurring domain, introduction of point mutations, introduction of altered or non-naturally occurring subsequences, or deletion of single amino acid residues, subsequences and/or domains.

An "inducible promoter" is one that mediates transcription of an operably linked gene in response to a particular stimulus.

As used herein, the phrase "in operable linkage" refers to a functional linkage between two sequences, such a control sequence (typically a promoter) and the linked sequence. A promoter is in operable linkage with an exogenous gene if it can mediate transcription of the gene.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

"Recombinant" is a cell, nucleic acid, protein or vector that has been modified due to the introduction of an exogenous nucleic acid or the alteration of a native nucleic acid. Thus, e.g., recombinant (host) cells can express genes that are not found within the native (non-recombinant) form of the cell or express native genes differently than those genes are expressed by a non-recombinant cell. Recombinant cells can, without limitation, include recombinant nucleic acids that encode a gene product or suppression elements such as mutations, knockouts, knockdowns, antisense, interfering RNA (RNAi) or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, using chemical synthesis, or otherwise is in a form not normally found in nature. Recombinant nucleic acids may be produced, for example, to place two or more nucleic acids in operable linkage. Thus, an isolated nucleic acid or an expression vector formed in vitro by nucleic by ligating DNA molecules that are not normally joined in nature, are both considered recombinant for the purposes of this invention. Recombinant nucleic acids can also be produced in other ways; e.g., using chemical DNA synthesis. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

A "transit peptide" is an amino acid sequence that directs the trafficking of a polypeptide fused to the signal sequence. In connection with plastidic cells expressing the polypeptide, the transit peptide may direct trafficking of the polypeptide to the plastid (i.e., a plastid targeting peptide).

The term "polynucleotide" refers to a deoxyribonucleotide or ribonucleotide polymer, and unless otherwise limited, includes known analogs of natural nucleotides that can function in a similar manner to naturally occurring nucleotides. The term "polynucleotide" refers any form of DNA or RNA, including, for example, genomic DNA; complementary DNA (cDNA), which is a DNA representation of mRNA, usually obtained by reverse transcription of messenger RNA (mRNA) or amplification; DNA molecules produced synthetically or by amplification; and mRNA. The term "polynucleotide" encompasses double-stranded nucleic acid molecules, as well as single-stranded molecules. In double-stranded polynucleotides, the polynucleotide strands need not be coextensive (i.e., a double-stranded polynucleotide need not be double-stranded along the entire length of both strands).

The term "host cell" refers to a cell capable of maintaining a vector either transiently or stably. Host cells include, without limitation, bacterial cells, yeast cells, insect cells, algal cells (e.g., microalgal cells), plant cells and mammalian cells. Other host cells known in the art, or which become known, are also suitable for use.

As used herein, the term "complementary" refers to the capacity for precise pairing between two nucleotides. For example, if a nucleotide at a given position of a nucleic acid molecule is capable of hybridizing with a nucleotide of another nucleic acid molecule, then the two nucleic acid molecules are considered to be complementary to one another at that position. The term "substantially complementary" describes sequences that are sufficiently complementary to one another to allow for specific hybridization under stringent hybridization conditions. In various embodiments, the variant genes encoding variant FATB genes disclosed below can be replaced with a substantially complementary gene having suitable activity.

The phrase "stringent hybridization conditions" generally refers to a temperature about 5° C. lower than the melting temperature (Tm) for a specific sequence at a defined ionic strength and pH. Exemplary stringent conditions suitable for achieving specific hybridization of most sequences are a temperature of at least about 60° C. and a salt concentration of about 0.2 molar at pH 7.0.

DETAILED DESCRIPTION

1. Introduction

Provided are heterologous KAS II enzymes that preferentially produce C18 acyl-ACP to facilitate the production of appreciable levels of C18 fatty acids, e.g., stearic (C18:0) acid, oleic (C18:1) acid and/or linoleic acid (C18:2), as well as increasing levels of C20 (e.g., eicosapentaenoic acid, arachidonic acid), C22 (e.g., docosahexaenoic acid, erucic acid) and/or C24 fatty acids, in microalgal (e.g., *Prototheca*) host cells. The KAS II enzyme variants can coordinate with a heterologous thioesterase that preferentially hydrolyzes C18-acyl ACP substrates into stearic (C18:0) acid, oleic (C18:1) acid and/or linoleic acid (C18:2) and acyl carrier proteins (ACPs), so that the resulting stearic, oleic and/or linoleic fatty acids can be incorporated into triglycerides (TAGs). Here, we report on the identification of a more active variant, PmKASII$^{A162X}$, for strain engineering. By over-expressing one or more copies of the PmKASII$^{A162X}$ gene variant in a *Prototheca* host strain, the resulting transgenic strains can produce triglyceride oils with modified fatty acid profiles, for example, fatty acid profiles comprising greater than 80%, 85%, 90%, or more, C18, C20, C22, and/or C24 fatty acids. These triglyceride oils also comprise a high level of monosaturated fatty acids (e.g., C18:1 fatty acid) and provide health benefits compared with saturated, hydrogenated (trans fats) often found in conventional food products.

2. β-Ketoacyl-ACP Synthase (KAS) II Variants

The variant β-ketoacyl-ACP synthase (KAS) II enzymes (KASII) can be used in genetic constructs and genetically engineered oleaginous cells (e.g., plants, algae, microalgae) with one or more exogenous genes to produce fatty acids, acyl glycerides, or derivatives thereof. For example, microalgae or oilseed crops that would naturally, or through genetic modification, produce high levels of triglycerides can be engineered (or further engineered) to express an exogenous variant KASII, which can catalyze the elongation of C14 acyl-ACP or C16 acyl-ACP to long-chain fatty acyl-ACP, e.g., from C14 to C16 or from C16 to C18, optionally producing C18 acyl-ACP, and/or facilitating the production of increased levels of C18, C20, C22, and/or C24 fatty acids, e.g., in comparison to a wild-type KASII. The fatty acids synthesized may be incorporated into acyl glycerides including triglycerides (TAGs, triacylglycerol). The triglycerides can be recovered or, through further enzymatic processing within the cell, or in vitro, yield other useful compounds.

Generally, the variant KASII enzymes described herein have preferential substrate specificity for C14 ACP or C16 ACP-fatty acyl substrates (e.g., to promote the elongation of C16 fatty acids to C18 fatty acids, and therefore, the production of C18 fatty acids). The variant KASII enzymes described herein catalyze the elongation of C14 acyl-ACP or C16 acyl-ACP to long-chain fatty acyl-ACP, e.g., from C14 to C16 or from C16 to C18 carbon atoms in length, and are categorized as EC 2.3.1.179 (β-ketoacyl-acyl-carrier-protein (ACP) synthase II).

In some embodiments, the non-natural KASII comprises at least about 80%, 85%, 90%, 91%, 92%, 93%, 94%, 95%, 96%, 97%, 98% or 99% sequence identity to amino acid residues 39-469 of SEQ ID NO:2, e.g., to amino acid residues 1-469 of SEQ ID NO:2, and comprises an X at the position corresponding to position 162; wherein X is an amino acid residue selected from the group consisting of cysteine (C), aspartate (D), glutamate (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W) and tyrosine (Y), wherein the positions are with reference to SEQ ID NO:2, and wherein the non-natural KASII catalyzes the elongation of C14 acyl-ACP, e.g., from C14 to C16. In some embodiments, the non-natural KASII comprises at least about 80%, 85%, 90%, 91%, 92%, 93%, 94%, 95%, 96%, 97%, 98% or 99% sequence identity to amino acid residues 39-469 of SEQ ID NO:2, e.g., to amino acid residues 1-469 of SEQ ID NO:2, and comprises an X at the position corresponding to position 162; wherein X is an amino acid residue selected from the group consisting of cysteine (C), aspartate (D), glutamate (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W) and tyrosine (Y), wherein the positions are with reference to SEQ ID NO:2, and wherein the non-natural KASII catalyzes the elongation of C16 acyl-ACP, e.g., from C16 to C18. In some embodiments, the non-natural KASII preferentially produces C18 acyl-ACP, e.g., C18:0 acyl-ACP, C18:1 acyl-ACP and/or C18:2 acyl-ACP. In some embodiments, the non-natural KASII facilitates the production of increased levels of C18, C20, C22, and/or C24 fatty acids in comparison to a wild-type KASII.

In some embodiments, the amino acid X at position 162 is an amino acid residue selected from serine (S), threonine (T) and valine (V). In some embodiments, the amino acid X at position 162 is an amino acid residue selected from isoleucine (I), leucine (L) and valine (V). In some embodiments, the amino acid X at position 162 is a valine (V) residue.

In some embodiments, the amino acid X at position 162 is an amino acid residue selected from cysteine (C), glutamate (E), lysine (K), methionine (M), serine (S), tryptophan (W), valine (V), asparagine (N), aspartate (D), glutamine (Q), histidine (H), leucine (L), phenylalanine (F), threonine (T), and tyrosine (Y).

In another embodiment, the amino acid at position at position 162 is selected from valine (V), asparagine (N), aspartate (D), glutamine (Q), histidine (H), leucine (L), phenylalanine (F), threonine (T), and tyrosine (Y).

In some embodiments, the non-natural or variant KASII comprises a plastid transit peptide. In some embodiments, the plastid transit peptide comprises at least about 80%, 85%, 90%, 91%, 92%, 93%, 94%, 95%, 96%, 97%, 98% or 99% identity to amino acid residues 1-35 of SEQ ID NO:7 or SEQ ID NO:8. In some embodiments, the plastid transit peptide is encoded by a polynucleotide comprising at least about 80%, 85%, 90%, 91%, 92%, 93%, 94%, 95%, 96%, 97%, 98% or 99% identity to SEQ ID NO:9 or SEQ ID NO:10.

In some embodiments, the polynucleotide comprises at least about 80%, 85%, 90%, 91%, 92%, 93%, 94%, 95%, 96%, 97%, 98% or 99% identity to nucleic acid residues 115-1407 of SEQ ID NO:6, e.g., wherein the nucleic acid base at position 1080 is a thymine (T). In some embodiments, the polynucleotide comprises at least about 80%, 85%, 90%, 91%, 92%, 93%, 94%, 95%, 96%, 97%, 98% or 99% identity to nucleic acid residues 1-1407 of SEQ ID NO:6, e.g., wherein the nucleic acid base at position 1080 is a T. In some embodiments, the polynucleotide comprises at least about 80%, 85%, 90%, 91%, 92%, 93%, 94%, 95%, 96%, 97%, 98% or 99% identity to SEQ ID NO:6. In some embodiments, the polynucleotide comprises codon bias for improved expression in a microalgal host cell, e.g., a *Prototheca* or *Chlorella* microalgal host cell.

In certain embodiments, provided is a fragment of any of the above-described proteins or nucleic acids (including fragments of protein or nucleic acid variants), wherein the protein fragment has activity, e.g., to catalyze the elongation of C14 acyl-ACP or C16 acyl-ACP, e.g., from C14 to C16 or from C16 to C18, optionally producing C18:0 acyl-ACP, C18:1 acyl-ACP and/or C18:2 acyl-ACP, and/or facilitating the production of increased levels of C18, C20, C22, and/or C24 fatty acids, e.g., in comparison to a wild-type KASII. Also contemplated are nucleic acid fragments encoding such protein fragments. In other embodiments, the fragment includes a domain of the KASII enzyme that mediates a particular function, e.g., elongation of C14 to C16 or C16 to C18 fatty acids. Illustrative fragments can be produced by C-terminal and/or N-terminal truncations and include at least 50%, 55%, 60%, 65%, 70%, 75%, 80%, 85%, 90%, 95%, 96%, 97%, 98%, or 99% of the full-length sequences disclosed herein.

3. Co-Expression with C18-Preferring Thioesterases

In some embodiments, the variant KASII enzyme is co-expressed with a heterologous or exogenous fatty acyl-ACP thioesterase. In an embodiment, polynucleotide encoding a variant KASII enzyme, as described herein, is co-expressed in a host cell with an exogenous FATA or FATB acyl-ACP thioesterase gene. FATA genes encode enzymes that preferentially, but not exclusively, hydrolyze long-chain fatty acids with highest activity towards C18:1, and in some instances C18:0. FATB genes encode a group of enzymes with more heterogeneous substrate specificities but generally show higher activity toward saturated fatty acids. The substrate specificities of FATB enzymes are quite heterogenous; there are a number of FATB enzymes that show high activity towards C18:0 and C18:1. FATA and FATB enzymes terminate the synthesis of fatty acids by hydrolyzing the thioester bond between the acyl moiety and the acyl carrier protein (ACP).

In some embodiments, the thioesterase preferentially hydrolyzes C18 acyl-ACP substrates, e.g., catalyzes the production of increased levels of C18 (e.g., C18:0, C18:1, C18:2), C20, C22, and/or C24 fatty acids and/or has increased specificity for C18 fatty acids in comparison to a wild-type thioesterase. Illustrative C18-preferring thioesterases of use for co-expression include without limitation a thioesterase from a plant genus selected from *Brassica, Carthamus, Camelina, Garcinia, Glycine, Mangifera, Helianthus, Madhura, Arachis, Morus, Ricinus, Herrania, Corchorus, Corchorus, Jatropha, Ziziphus, Trema orientalis, Hevea, Theobroma, Quercus, Cucurbita, Dorcoceras, Rosa, Asparagus, Cephalotus, Parasponia, Carica, Arabidopsis, Capsella* and *Eutrema*. In some embodiments, the variant KASII is co-expressed with a thioesterase from a plant species selected from *Brassica napus, Brassica campestris, Brassica juncea, Carthamus tinctorius, Camelina saliva, Garcinia mangostana, Glycine max, Mangifera indica, Helianthus annuus, Madhura longifolia, Arachis hypogaea, Morus notabilis, Ricinus communis, Herrania umbratical, Corchorus olitorius, Corchorus capsularis, Jatropha curcas, Ziziphus jujube, Trema orientalis, Hevea brasiliensis, Theobroma cacao, Quercus suber, Cucurbita maxima, Cucurbita pepo, Cucurbita moschata, Dorcoceras hygrometricum, Rosa chinensis, Asparagus officinalis, Cephalotus follicularis, Parasponia andersonii, Carica papaya, Arabidopsis thaliana, Capsella rubella* and *Eutrema salsugineum*. In some embodiments, the variant KASII is co-expressed with a *Garcinia mangostana* (GmFATA) thioesterase, optionally comprising one or more amino acid substitutions selected from the group consisting of L91F, L91K, L91S, G96A, G96T, G96V, G108A, G108V, S111A, S111V, T156F, T156A, T156K, T156V and V193A, wherein the amino acid positions are with reference to SEQ ID NO:11. In some embodiments, the variant KASII is co-expressed with *Brassica napus* BnOTE (Accession No. CAA52070) and its variants, e.g., as described in US2016/0083758, which is hereby incorporated herein by reference in its entirety for all purposes.

4. Co-Expression with Other Lipid Biosynthesis Enzymes

In some embodiments, the variant KASII enzyme is co-expressed with one or more heterologous or exogenous lipid biosynthesis enzymes. In some embodiments, the variant KASII enzyme is co-expressed with one or more heterologous or exogenous lipid biosynthesis enzymes selected from the group consisting of a fatty acyl thioesterase A (FATA), a fatty acyl thioesterase B (FATB), a fatty acyl desaturase (FAD), including without limitation phosphatidylglycerol desaturase (FAD4), plastidial oleate desaturase (FADE), plastidial linoleate desaturase (FAD7/FAD8), endoplasmic reticulum oleate desaturase (FAD2), endoplasmic reticulum linolate desaturase (FAD3), delta 12 fatty acid desaturase (412 FAD), delta 15 fatty acid desaturase (Δ15 FAD), and stearoyl-ACP desaturase 2 (SAD2); a 1-acylglycerol-3-phosphate O-acyltransferase (LPAAT), a glycerol-3-phosphate acyltransferase (GPAT), an acyl CoA:diacylglycerol acyltransferase (DGAT), a fatty acid and a fatty acid elongase (FAE), and a long-chain acyl-CoA synthetase (LACS). In some embodiments, the variant KASII enzyme is co-expressed with one or more exogenous or heterologous enzymes, such as a sucrose invertase, an alpha galactosidase, and a 4-amino-5-hydroxymethyl-2-methylpyrimidine phosphate synthase (THIC). Recombinant expression of heterologous or exogenous lipid biosynthesis enzymes is described, e.g., in U.S. Patent Publ. No. 2014/0178950, which is incorporated herein by reference in its entirety for all purposes. For example, one or more polynucleotides encoding one or more of the aforementioned lipid biosynthesis enzymes can be used in a variety of genetic constructs including plasmids or other vectors for expression or recombination in a host cell. The genes can be codon optimized for expression in a target host cell. The genes can be included in an expression cassette that includes a promoter (e.g., a heterologous promoter) and downstream regulatory element. The vector can include flanking sequences for homologous recombination. For example, the vector can cause insertion into a chromosome of the host cell, where it can be stably expressed. The proteins produced by the genes can be used in vivo or in purified form. In an embodiment, an expression cassette comprises a homologous promoter, a CDS operable to express one or more lipid biosynthesis enzymes and a 3'UTR. The 3'UTR can comprise a polyadenylation site.

In some embodiments, one or more lipid biosynthesis enzymes endogenous to the host cell selected from the group consisting of a fatty acyl thioesterase A (FATA), a fatty acyl thioesterase B (FATB), a fatty acyl desaturase (FAD), including without limitation phosphatidylglycerol desaturase (FAD4), plastidial oleate desaturase (FADE), plastidial linoleate desaturase (FAD7/FAD8), endoplasmic reticulum oleate desaturase (FAD2), endoplasmic reticulum linolate desaturase (FAD3), delta 12 fatty acid desaturase (Δ12 FAD), delta 15 fatty acid desaturase (Δ15 FAD), and stearoyl-ACP desaturase 2 (SAD2); a 1-acylglycerol-3-phosphate O-acyltransferase (LPAAT), a glycerol-3-phosphate acyltransferase (GPAT), an acyl CoA:diacylglycerol acyltransferase (DGAT), a fatty acid elongase (FAE) and a long-chain acyl-CoA synthetase (LACS) are deleted, knocked out or knocked down. For example, one or more polynucleotides encoding one or more of the aforementioned lipid biosynthesis enzymes can also be used to prepare antisense, or inhibitory RNA (e.g., RNAi or hairpin RNA) to inhibit complementary genes in the microalgal host cell. For example, armed with the knowledge of a gene sequence encoding one of the aforementioned proteins, one can engineer a microalgal host cells with the same or similar gene to express an RNAi construct, gene knockout, knockdown, point mutation, or the like, and thereby reduce the expression and/or activity of one or more of the enzymes in the microalgal host cell. As a result, the microalgae can produce an oil with an altered fatty acid profile in which the mean chain length is decreased or increased, depending on the presence of other fatty acid synthesis genes. In some embodiments, a mutation (including knockout) or inhibition (e.g., using antisense or RNAi) of one or more endogenous desaturase genes (e.g., a stearoyl-ACP desaturase or fatty acid desaturase including a delta 12 fatty acid desaturase) can reduce or eliminate desaturase activity to produce a more fully saturated oil profile.

Depending on the desired properties of the lipid molecule to be produced, one or more genes encoding enzymes that utilize fatty acids or fatty acyl molecules as substrates to produce lipid molecules may be attenuated or over-expressed in the host cell (e.g., microalga), for example using RNAi, hairpin constructs, knockdowns, double or single knockouts or replacement (e.g., replacing an endogenous gene with a heterologous gene).

5. Codon-Bias for Improved Expression in Microalgal Host Cells

DNA encoding a polypeptide to be expressed in a microorganism, e.g., a KASII variant, optionally with an exogenous lipid biosynthesis enzyme, e.g., a fatty acyl-ACP thioesterase, and selectable marker can be codon-optimized cDNA. Methods of recoding genes for expression in microalgae are described in U.S. Pat. No. 7,135,290. Additional information for codon optimization is available, e.g., at the Codon Usage Database at kazusa.or.jp/codon/. The table for *Prototheca* preferred codon usage is also provided in U.S. Patent Publ. No. 2012/0283460. Preferred codon usage in *Prototheca* and *Chlorella protothecoides* is provided in Tables A and B.

TABLE A

Preferred codon usage in *Prototheca* strains.

| Amino Acid | Codon | Usage Frequency |
|---|---|---|
| Ala | GCG | 36% |
| | GCA | 7% |
| | GCT | 11% |
| | GCC | 46% |
| Arg | AGG | 6% |
| | AGA | 2% |
| | CGG | 18% |
| | CGA | 8% |
| | CGT | 9% |
| | CGC | 57% |
| Asn | AAT | 4% |
| | AAC | 96% |
| Asp | GAT | 12% |
| | GAC | 88% |
| Cys | TGT | 10% |
| | TGC | 90% |
| Gln | CAG | 82% |
| | CAA | 18% |
| Glu | GAG | 96% |
| | GAA | 4% |
| Gly | GGG | 12% |
| | GGA | 7% |
| | GGT | 10% |
| | GGC | 71% |
| His | CAT | 21% |
| | CAC | 79% |
| Ile | ATA | 1% |
| | ATT | 8% |
| | ATC | 91% |
| Lys | AAG | 98% |
| | AAA | 2% |
| Leu | TTG | 4% |
| | TTA | 0% |
| | CTG | 61% |
| | CTA | 3% |
| | CTT | 6% |
| | CTC | 26% |
| Met | ATG | 100% |
| Phe | TTT | 29% |
| | TTC | 71% |
| Pro | CCG | 29% |
| | CCA | 9% |
| | CCT | 13% |
| | CCC | 49% |
| Ser | AGT | 3% |
| | AGC | 22% |
| | TCG | 28% |
| | TCA | 6% |
| | TCT | 10% |
| | TCC | 31% |
| Thr | ACG | 38% |
| | ACA | 5% |
| | ACT | 5% |
| | ACC | 52% |
| Tyr | TAT | 5% |
| | TAC | 95% |

TABLE A-continued

Preferred codon usage in *Prototheca* strains.

| Amino Acid | Codon | Usage Frequency |
|---|---|---|
| Trp | TGG | 100% |
| Val | GTG | 50% |
|  | GTA | 1% |
|  | GTT | 6% |
|  | GTC | 43% |
| Stop | TGA/TAG/TAA | |

TABLE B

Preferred codon usage in Chlorella protothecoides.

| Amino Acid | Preferred Codon |
|---|---|
| Arg | CGC |
| Ala | GCC |
| Asn | AAC |
| Asp | GAC |
| Cys | TGC |
| Gln | CAG |
| Glu | GAG |
| Gly | GGC |
| His | CAC |
| Ile | ATC |
| Leu | CTG |
| Lys | AAG |
| Met | ATG |
| Phe | TTC |
| Pro | CCC |
| Ser | TCC |
| Thr | ACC |
| Trp | TGG |
| Tyr | TAC |
| Val | GTG |
| Stop | TGA |

In various embodiments, the nucleic acids encoding the KASII variants, and optionally the exogenous co-expressed lipid biosynthesis enzyme, e.g., fatty acyl-ACP thioesterase, can be codon biased for improved expression in a target host cell. For expression in a *Prototheca* or a *Chlorella* host cell, the encoding polynucleotide can be recoded, using the preferred codons identified in Tables A or B, respectively. For example, in some embodiments, at least 60%, 65%, 70%, 75%, 80%, 85%, 90%, 95%, or 100% of the codons used in the encoding polynucleotide can be the most preferred codon according to Tables A or B. In some embodiments, at least 60%, 65%, 70%, 75%, 80%, 85%, 90%, 95%, or 100% of the codons used in the encoding polynucleotide can be the first or second most preferred codon according to Tables A and B. In some embodiments, the non-natural or variant β-ketoacyl-ACP synthase (KAS) II enzyme (KASII) is encoded by a polynucleotide comprising at least about 80%, 85%, 90%, 91%, 92%, 93%, 94%, 95%, 96%, 97%, 98% or 99% identity to nucleic acid residues 115-1407 of SEQ ID NO:6, e.g., nucleic acid residues 1-1407 of SEQ ID NO:6. In some embodiments, the non-natural or variant β-ketoacyl-ACP synthase (KAS) II enzyme (KASII) is encoded by a polynucleotide comprising at least about 80%, 85%, 90%, 91%, 92%, 93%, 94%, 95%, 96%, 97%, 98% or 99% identity to SEQ ID NO:6.

6. Expression and Targeting to Plastids

Heterologous or exogenous proteins expressed in the nuclear genome of *Prototheca* can be targeted to the plastid using plastid targeting signals. Plastid targeting sequences endogenous to *Chlorella* are known, such as genes in the *Chlorella* nuclear genome that encode proteins that are targeted to the plastid; see for example GenBank Accession numbers AY646197 and AF499684, and in one embodiment, such control sequences are used in the vectors described herein, e.g., to target expression of a protein to a *Prototheca* plastid.

The Examples below describe the use of algal plastid targeting sequences to target heterologous proteins to the correct compartment in the host cell. cDNA libraries were made using *Prototheca moriformis* and *Chlorella protothecoides* cells and are described in the Examples of U.S. Patent Publ. No. 2012/0283460 and in PCT Application No. PCT/US2009/066142. Amino acid sequences of the algal plastid targeting sequences identified from the cDNA libraries useful plastid targeting of recombinantly expressed variant KASII enzymes are provided in U.S. Patent Publ. No. 2012/0283460 and herein. In some embodiments, the plastid transit peptide comprises an amino acid sequence selected from the group consisting of MATASTFSAFNAR-CGDLRRSAGSGPRRPARPLPVRGRA (SEQ ID NO:15), SGPRRPARPLPVR (SEQ ID NO:16), SGPRRPAR-PLPVRAAIASEVPVATTSPR (SEQ ID NO:17), RPAR-PLPVRGRA (SEQ ID NO:18), RPARPLPVRAAIASEVP-VATTSPR (SEQ ID NO:19), RCGDLRRSAGSGPRRPARPLPVRGRA (SEQ ID NO:20), RCGDLRRSAGSGPRRPARPLPVRAAIASEVP-VATTSPR (SEQ ID NO:21), PARPLPVR (SEQ ID NO:22), PARPLPVRAAIASEVPVATTSPR (SEQ ID NO:23), RRPARPLPVR (SEQ ID NO:24), and RRPARPLPVRAA-IASEVPVATTSPR (SEQ ID NO:25). In some embodiments, the plastid transit peptide comprises at least about 80%, 85%, 90%, 91%, 92%, 93%, 94%, 95%, 96%, 97%, 98% or 99% identity to amino acid residues 1-33 of SEQ ID NO:1, amino acid residues 1-33 of SEQ ID NO:2, SEQ ID NO:7 or SEQ ID NO:8. In some embodiments, the plastid transit peptide is encoded by a polynucleotide comprising at least about 80%, 85%, 90%, 91%, 92%, 93%, 94%, 95%, 96%, 97%, 98% or 99% identity to SEQ ID NO:9 or SEQ ID NO:10.

Where novel KASII variants are disclosed here, it will be understood that a variety of heterologous plastid transit peptides can be used. In other words, the non-targeting peptide domain is more highly conserved. Accordingly, embodiments described herein feature the novel KASII enzymatic domain with or without a plastid targeting sequence. For example, where a percent identity to a novel KASII gene is given herein, the same identity can be applied (where specified) to the same sequence absent the targeting peptide. A substitute targeting peptide can optionally be used in connection with such a sequence.

7. Host Cells—Oil- or Lipid-Producing Microorganisms

Any species of organism that produces suitable triglycerides can be used, although microorganisms that naturally produce high levels of suitable triglyceride are preferred. Considerations for the selection of microorganisms include, in addition to production of suitable triglycerides for production of oils and oleochemicals: (1) high lipid content as a percentage of dry cell weight; (2) ease of growth; (3) ease of genetic engineering; and (4) ease of biomass processing. In particular embodiments, the wild-type, classically improved or genetically engineered microorganism yields cells that are at least 40%, at least 45%, at least 50%, at least 55%, at least 60%, at least 65%, or at least 70% or more lipid as a percentage of their dry cell weight. Preferred organisms grow heterotrophically (on sugars in the absence of light) or can be engineered to do so using, for example, methods disclosed herein. The ease of transformation and availability of selectable markers and promoters, constitutive or inducible, that are functional in the microorganism affect the ease of genetic engineering. Examples of selectable markers useful in microalgae include sucrose invertase, alpha galactosidase (for selection on melibiose) and antibiotic resistance genes. Processing considerations can include, for example, the availability of effective means for lysing the cells.

Microalgae

In some embodiments, the microorganism is a microalga. Non-limiting examples of microalgae that can be used for expression of variant KASII enzymes include, e.g., *Achnanthes orientalis, Agmenellum, Amphiprora hyaline, Amphora coffeiformis, Amphora coffeiformis linea, Amphora coffeiformis punctata, Amphora coffeiformis taylori, Amphora coffeiformis tenuis, Amphora delicatissima, Amphora delicatissima capitata, Amphora* sp., *Anabaena, Ankistrodesmus, Ankistrodesmus fakatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri subsalsum, Chaetoceros* sp., *Chlorella anitrata, Chlorella Antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora* (strain SAG 37.88), *Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides* (including any of UTEX strains 1806, 411, 264, 256, 255, 250, 249, 31, 29, 25), *Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris f. tertia, Chlorella vulgaris* var. *autotrophica, Chlorella vulgaris* var. *viridis, Chlorella vulgaris* var. *vulgaris, Chlorella vulgaris* var. *vulgaris f. tertia, Chlorella vulgaris* var. *vulgaris f. viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena, Franceia* sp., *Fragilaria crotonensis, Fragilaria* sp., *Gleocapsa* sp., *Gloeothamnion* sp., *Hymenomonas* sp., *Isochrysis aff. galbana, Isochrysis galbana, Lepocinclis, Micractinium, Micractinium* (UTEX LB 2614), *Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pellicuosa, Navicula saprophila, Navicula* sp., *Nephrochloris* sp., *Nephroselmis* sp., *Nitschia communis, Nitzschia alexandrina, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Tetraedron, Tetraselmis* sp., *Tetraselmis suecica, Thalassiosira weissflogii,* and *Viridiella fridericiana.*

Illustrative host cells feature oleaginous cells that produce altered fatty acid profiles and/or altered regiospecific distribution of fatty acids in glycerolipids, and products produced from the cells. Examples of oleaginous cells include microbial cells having a type II lipid biosynthesis pathway, including plastidic oleaginous cells such as those of oleaginous algae. Specific examples of cells include heterotrophic or obligate heterotrophic microalgae of the phylum Chlorpophya, the class Trebouxiophytae, the order Chlorellales, or the family Chlorellacae. Examples of oleaginous microalgae are provided in Published PCT Patent Applications WO2008/151149, WO2010/06032, WO2011/150410, and WO2011/150411, including species of *Chlorella* and *Prototheca*, a genus comprising obligate heterotrophs. The oleaginous cells can be, for example, capable of producing 25, 30, 40, 50, 60, 70, 80, 85, or about 90% oil by dry cell weight, ±5%. The above mentioned publications also disclose methods for cultivating such cells and extracting oil, especially from microalgal cells; such methods are applicable to the cells disclosed herein. In any of the embodiments described herein, the cells can be heterotrophic cells comprising an exogenous sucrose invertase gene so as to allow the cells to produce oil from a sucrose feedstock.

The oleaginous cells produce a storage oil, which may be stored in storage vesicles of the cell. A raw oil may be obtained from the cells by disrupting the cells and isolating the oil. The oils produced may be refined, bleached and deodorized (RBD) as known in the art or as described in WO2010/120939. The raw or RBD oils may be used in a variety of food, chemical, and industrial products or processes. After recovery of the oil, a valuable residual biomass remains. Uses for the residual biomass include the production of paper, plastics, absorbents, adsorbents, as animal feed, for human nutrition, or for fertilizer.

Where a fatty acid profile of a triglyceride cell oil is given, it will be understood that this refers to a nonfractionated sample of the storage oil extracted from the cell analyzed under conditions in which phospholipids have been removed or with an analysis method that is substantially insensitive to the fatty acids of the phospholipids (e.g. using chromatography and mass spectrometry). Because the cells are oleaginous, in some cases the storage oil will constitute the bulk of all the triglycerides in the cell.

In some embodiments, the host cell is a plastidic cell, e.g., a heterotrophic microalga of the phylum Chlorpophya, the class Trebouxiophytae, the order Chlorellales, or the family Chlorellacae. In some embodiments, the cell is oleaginous and capable of accumulating at least 40% oil by dry cell weight. The cell can be an obligate heterotroph, such as a species of *Prototheca*, including *Prototheca moriformis* or *Prototheca zopfii*. The nucleic acid encoding the variant KASII enzymes described herein can also be expressed in autotrophic algae or plants. Optionally, the cell is capable of using sucrose to produce oil and a recombinant invertase gene may be introduced to allow metabolism of sucrose, as described in PCT Publications WO2008/151149, WO2010/06032, WO2011/150410, WO2011/150411, and international patent application PCT/US12/23696. The invertase can be codon-biased and integrated into a chromosome of the cell, as well as any of the genes mentioned herein. Codon usage for different algal and plant species of interest is known in the art and can be found, e.g., on the internet at the Codon Usage Database at kazusa.or.jp/codon/.

The polynucleotides encoding the variant KASII enzymes described herein further can be expressed in a wide variety of plant and microalgal host cells. Of particular interest are plant cells of plants involved in the production of vegetable oils for edible and industrial uses, including e.g., temperate oilseed crops. Plants of interest include, but are not limited to, rapeseed (Canola and High Erucic Acid varieties), sunflower, safflower, cotton, *Cuphea*, soybean, peanut, coconut and oil palms, and corn. See, U.S. Pat. Nos. 5,850,022; 5,723,761; 5,639,790; 5,807,893; 5,455,167; 5,654,495; 5,512,482; 5,298,421; 5,667,997; and U.S. Pat. Nos. 5,344,771; 5,304,481.

8. Methods of Culturing Microorganisms

Microorganisms are cultured both for purposes of conducting genetic manipulations and for subsequent production of oil or triglycerides (TGs, triacylglycerols, TAGs, or triacylglycerides). The former type of culture is conducted on a small scale and initially, at least, under conditions in which the starting microorganism can grow. For example, if the starting microorganism is a photoautotroph the initial culture is conducted in the presence of light. The culture conditions can be changed if the microorganism is evolved or engineered to grow independently of light. Culture for purposes of oil or triglyceride production is usually conducted on a large scale. Preferably a fixed carbon source is present. The culture can also be exposed to light some or all of the time.

Microalgae can be cultured in liquid media. The culture can be contained within a bioreactor. Optionally, the bioreactor does not allow light to enter. Alternatively, microalgae can also be cultured in photobioreactors that contain a fixed carbon source and allow light to strike the cells. Exposure of microalgal cells to light, even in the presence of a fixed carbon source that the cells transport and utilize (i.e., mixotrophic growth), nonetheless accelerates growth compared to culturing cells in the dark. Culture condition parameters can be manipulated to increase or improve total triglyceride production, the combination of triglyceride species produced, and/or production of a triglyceride species. In some instances it is preferable to culture cells in the dark, such as, for example, when using extremely large (e.g., 10,000 L, 40,000 L, 100,000 L, 500,000 L, or larger, bioreactors) fermentors that do not allow light to strike the culture.

Microalgal culture media typically contain components such as a fixed nitrogen source, trace elements, vitamins (e.g., thiamine), optionally a buffer for pH maintenance, and phosphate. Other components can include a fixed carbon source such as acetate or glucose, and salts such as sodium chloride, particularly for seawater microalgae. Examples of trace elements include zinc, boron, cobalt, copper, manganese, and molybdenum in, for example, the respective forms of $ZnCl_2$, $H_3BO_3$, $CoCl_2.6H_2O$, $CuCl_2.2H_2O$, $MnCl_2.4H_2O$ and $(NH_4)_6Mo_7O_{24}.4H_2O$.

For organisms able to grow on a fixed carbon source, the fixed carbon source can be, for example, glucose, fructose, sucrose, galactose, xylose, mannose, rhamnose, N-acetylglucosamine, glycerol, floridoside, and/or glucuronic acid. The one or more carbon source(s) can be supplied at a concentration of at least about 50 μM, at least about 100 μM, at least about 500 μM, at least about 5 mM, at least about 50 mM, and at least about 500 mM, of one or more exogenously provided fixed carbon source(s). Some microalgal species can grow by utilizing a fixed carbon source such as glucose or acetate in the absence of light. Such growth is known as heterotrophic growth. For *Chlorella* and/or *Prototheca*, for example, heterotrophic growth results in high production of biomass and accumulation of high lipid content in cells.

Some microorganisms naturally grow on or can be engineered to grow on a fixed carbon source that is a heterogeneous source of compounds such as municipal waste, secondarily treated sewage, wastewater, and other sources of fixed carbon and other nutrients such as sulfates, phosphates, and nitrates. The sewage component serves as a nutrient source in the production of triglycerides, and the culture provides an inexpensive source of triglycerides.

Other culture parameters can also be manipulated, such as the pH of the culture media, the identity and concentration of trace elements and other media constituents.

Heterotrophic Growth

As an alternative to photosynthetic growth of microorganisms, some microorganisms can be cultured under heterotrophic growth conditions in which a fixed carbon source provides energy for growth and lipid accumulation.

In one heterotrophic culture method, crude, partially purified, or purified glycerol produced as a byproduct of lipid transesterification can be employed as a feedstock for fermenting, for example, lipid-producing microbial cultures. Thus, the methods can involve culturing a microbe (e.g., a microalga) in a first microbial culture; recovering microbial lipid from the culture; subjecting the microbial lipid to transesterification to produce fatty acid ester(s) and glycerol, as described above; and adding the glycerol to a second microbial culture as a feedstock. The first and second microbial cultures can, but need not, be cultures of the same microbe. If desired, a continuous system can be devised whereby glycerol produced from the lipid recovered from a culture can be fed back into the same culture.

Provided are significantly improved culture parameters incorporating the use of glycerol for fermentation of multiple genera of both eukaryotic and prokaryotic microbes, including microbes of the genera *Prototheca, Chlorella, Navicula, Scenedesmus*, and *Spirulina*. Standard methods for the growth and propagation of *Chlorella* and/or *Prototheca* are known (see for example Miao and Wu, J. Biotechnology, 2004, 11:85-93 and Miao and Wu, Biosource Technology (2006) 97:841-846). In addition, multiple species of *Chlorella* and/or *Prototheca* and multiple strains within a species can be grown, e.g., in the presence of a sugar (e.g., glucose, sucrose, xylose) and/or glycerol, including glycerol byproduct from biodiesel transesterification.

For oil production, cells, including recombinant cells described herein, are preferably cultured or fermented in large quantities. The culturing may be in large liquid volumes, such as in suspension cultures as an example. Other examples include starting with a small culture of cells which expand into a large biomass in combination with cell growth and propagation as well as oil production. Bioreactors or steel fermentors can be used to accommodate large culture volumes. A fermentor similar to those used in the production of beer and/or wine is suitable, as are extremely large fermentors used in the production of ethanol.

Appropriate nutrient sources for culture in a fermentor are provided. These include raw materials such as one or more of the following: a fixed carbon source such as glucose, corn starch, depolymerized cellulosic material, sucrose, sugar cane, sugar beet, lactose, milk whey, or molasses; a fat source, such as fats or vegetable oils; a nitrogen source, such as protein, soybean meal, cornsteep liquor, ammonia (pure or in salt form), nitrate or nitrate salt, or molecular nitrogen; and a phosphorus source, such as phosphate salts. Additionally, a fermentor allows for the control of culture conditions such as temperature, pH, oxygen tension, and carbon dioxide levels. Optionally, gaseous components, like oxygen or nitrogen, can be bubbled through a liquid culture. Other starch (polymerized glucose) sources such as wheat, potato, rice, and sorghum. Other carbon sources include process streams such as technical grade glycerol, black liquor, organic acids such as acetate, and molasses. Carbon sources can also be provided as a mixture, such as a mixture of sucrose and depolymerized sugar beet pulp.

A fermentor can be used to allow cells to undergo the various phases of their growth cycle. As an example, an inoculum of oil-producing cells can be introduced into a medium followed by a lag period (lag phase) before the cells begin growth. Following the lag period, the growth rate increases steadily and enters the log, or exponential, phase. The exponential phase is in turn followed by a slowing of growth due to decreases in nutrients and/or increases in toxic substances. After this slowing, growth stops, and the cells enter a stationary phase or steady state, depending on the particular environment provided to the cells.

Oil production by cells disclosed herein can occur during the log phase or thereafter, including the stationary phase wherein nutrients are supplied, or still available, to allow the continuation of oil production in the absence of cell division.

In some embodiments, microorganisms grown using conditions described herein and comprise at least about 20% by weight of lipids, preferably at least about 40% by weight, at least about 50% by weight, and more preferably at least about 60% by weight, even more preferably at least about 70%, 75%, 80% or 85% by weight.

In one heterotrophic growth method, sucrose, produced by example from sugar cane or sugar beet, is used as a feedstock. Oil production can be facilitated or made more efficient through the engineering of microbes such as *Chlorella* and/or *Prototheca*, to utilize sucrose as a carbon source. For example, expression of a sucrose transporter and a sucrose invertase allows *Chlorella* and/or *Prototheca* to transport sucrose into the cell from the culture media and hydrolyze sucrose to yield glucose and fructose. Optionally, a fructokinase can be expressed as well in instances where endogenous hexokinase activity is insufficient for maximum phosphorylation of fructose. Examples of suitable sucrose transporters are Genbank accession numbers CAD91334, CAB92307, and CAA53390. Examples of suitable sucrose invertases are Genbank accession numbers CAB95010, NP012104 and CAA06839. Examples of suitable fructokinases are Genbank accession numbers P26984, P26420 and CAA43322. Vectors for transformation of microalgae, including *Chlorella* and/or *Prototheca*, encoding one or more of such genes can be designed as described herein.

Secretion of a sucrose invertase can obviate the need for expression of a transporter that can transport sucrose into the cell. This is because a secreted invertase catalyzes the conversion of a molecule of sucrose into a molecule of glucose and a molecule of fructose, both of which can be transported and utilized by microbes disclosed herein. For example, expression of a sucrose invertase with a secretion signal generates invertase activity outside the cell. See Hawkins et al., Current Microbiology Vol. 38 (1999), pp. 335-341 for examples of secretion signals active in *Chlorella* and/or *Prototheca*. Expression of such a protein, as enabled by the genetic engineering methodology disclosed herein, allows cells already capable of utilizing extracellular glucose as an energy source to utilize sucrose as an extracellular energy source. *Chlorella* and/or *Prototheca* cells can use both extracellular fructose and extracellular glucose as an energy source, secretion of an invertase can provide the sole catalytic activity necessary for use of sucrose as an efficient, inexpensive energy source.

For example, *Chlorella* and/or *Prototheca* cells can be engineered with a sucrose invertase gene under the regulatory control of one of three promoters (Cauliflower mosaic virus 35S promoter (CMV), *Chlorella* virus promoter (CV), or *Chlorella* HUP1 promoter (HUP 1)). The sucrose invertase gene used in this example comprises codon-bias to the *S. cerevisiae* SUC2 gene to improve expression in a *C. protothecoides* host cell. Expression of a secretable sucrose invertase, such as that described herein, permits the use of molasses, sugar cane juice, and other sucrose-containing feedstocks for cell fermentation.

Alternatively, a sucrose invertase can also be expressed intracellularly in cells that express a sucrose transporter, as well as in cells that express any carbohydrate transporter that allows sucrose to enter the cell.

Bioreactors can be employed for use in heterotrophic growth methods. As will be appreciated, provisions made to make light available to the cells in photosynthetic growth methods are unnecessary when using a fixed-carbon source in the heterotrophic growth methods described herein.

The specific examples of process conditions and heterotrophic growth methods described herein can be combined in any suitable manner to improve efficiencies of microbial growth and/or lipid production. Additionally, conditions and heterotrophic growth methods are useful in the selection and/or genetic engineering of microbes, such as microalgae, to produce microbes that are even more suitable for use in the above-described methods. For example, the microbes having a greater ability to utilize any of the above-described feedstocks for increased proliferation and/or lipid (e.g., fatty acid) production are within the scope of the compositions and methods described herein.

Growth Media

Microorganisms useful in accordance with the methods described herein are found in various locations and environments throughout the world. As a consequence of their isolation from other species and their resulting evolutionary divergence, the particular growth medium for optimal growth and generation of triglyceride constituents can be difficult to predict. In some cases, certain strains of microorganisms may be unable to grow on a particular growth medium because of the presence of some inhibitory component or the absence of some essential nutritional requirement required by the particular strain of microorganism.

Solid and liquid growth media are generally available from a wide variety of sources, and instructions for the preparation of particular media that is suitable for a wide variety of strains of microorganisms can be found, for example, online at utex.org/, a site maintained by the University of Texas at Austin for its culture collection of algae (UTEX). For example, various fresh water and salt water media are provided in U.S. Patent Publ. No. 2012/0288930, hereby incorporated herein by reference in its entirety for all purposes.

In a particular example, a medium suitable for culturing *Chlorella* and/or *Prototheca* cells comprises Proteose Medium. This medium is suitable for axenic cultures, and a 1 L volume of the medium (pH .about.6.8) can be prepared by addition of 1 g of proteose peptone to 1 liter of Bristol Medium. Bristol medium comprises 2.94 mM NaNO$_3$, 0.17 mM CaCl$_2$2H$_2$O, 0.3 mM MgSO$_4$7H$_2$O, 0.43 mM, 1.29 mM KH$_2$PO$_4$, and 1.43 mM NaCl in an aqueous solution. For 1.5% agar medium, 15 g of agar can be added to 1 L of the solution. The solution is covered and autoclaved, and then stored at a refrigerated temperature prior to use.

Other suitable media for use with the methods described herein can be readily identified by consulting the URL identified above, or by consulting other organizations that maintain cultures of microorganisms, such as SAG, CCAP, or CCALA. SAG refers to the Culture Collection of Algae at the University of Gottingen (Gottingen, Germany), CCAP refers to the culture collection of algae and protozoa managed by the Scottish Association for Marine Science (Scotland, United Kingdom), and CCALA refers to the culture collection of algal laboratory at the Institute of Botany (ccala.butbn.cas.cz/, Czech Republic).

Increasing Production of Lipids

Process conditions can be adjusted to increase the production of lipids suitable for a particular use and/or to reduce production cost. For example, in certain embodiments, an oleaginous cell (e.g., a plant, an algae, a microalga) is cultured in the presence of a limiting concentration of one or more nutrients, such as, for example, carbon and/or nitrogen, phosphorous, or sulfur, while providing an excess of fixed carbon energy such as glucose. Nitrogen limitation tends to increase microbial lipid production over microbial lipid production in a culture in which nitrogen is provided in excess. In particular embodiments, the increase in lipid production is at least about: 10%, 20%, 30%, 40%, 50%, 75%, 100%, 200%, 300%, 400%, or 500%. The oleaginous cells (e.g., plant cells, algae cells, microalgal cells) can be cultured in the presence of a limiting amount of a nutrient for a portion of the total culture period or for the entire period. In particular embodiments, the nutrient concentration is cycled between a limiting concentration and a non-limiting concentration at least twice during the total culture period.

In another embodiment, lipid production is increased by culturing oleaginous cells or an oleaginous organism (e.g., plants, algae, microalgae) in the presence of one or more cofactor(s) for a lipid biosynthesis enzyme (e.g., a fatty acid synthetic enzyme). Generally, the concentration of the cofactor(s) is sufficient to increase microbial lipid (e.g., fatty acid) production over microbial lipid production in the absence of the cofactor(s). In a particular embodiment, the cofactor(s) are provided to the culture by including in the culture oleaginous cells (e.g., plant cells, algae cells, microalgal cells) containing an exogenous gene encoding the cofactor(s). Alternatively, cofactor(s) may be provided to a culture by including an oleaginous cell (e.g., a plant, an algae, a microalga) containing an exogenous gene that encodes a protein that participates in the synthesis of the cofactor. In certain embodiments, suitable cofactors include any vitamin required by a lipid biosynthesis enzyme, such as, for example: biotin, pantothenate. Genes encoding cofactors suitable for use in the present compositions and methods or that participate in the synthesis of such cofactors are well known and can be introduced into oleaginous cells (e.g., plant cells, algae cells, microalgal cells), using constructs and techniques such as those described above and herein.

In some embodiments, the cells can be fully auxotrophic or partially auxotrophic (i.e., synthetic sickness or lethality) with respect to one or more types of fatty acid. The cells are cultured with supplementation of the fatty acid(s) so as to increase the cell number, then allowing the cells to accumulate oil (e.g., to at least 40% by dry cell weight). Alternatively, the cells comprise a regulatable fatty acid synthesis gene that can be switched in activity based on environmental conditions and the environmental conditions during a first, cell division, phase favor production of the fatty acid and the environmental conditions during a second, oil accumulation phase disfavor production of the fatty acid.

As a result of applying either of these supplementation or regulation methods, a cell oil may be obtained from the cell that has low amounts of one or more fatty acids essential for optimal cell propagation. Specific examples of oils that can be obtained include those low in stearic, linoleic and/or linolenic acids. Optionally, the cells are oleaginous plastidic microbes such as those of the division Chlorophyta.

Accordingly, in some embodiments, provided are methods for producing an oil or fat. The method comprises cultivating a recombinant oleaginous cell in a growth phase under a first set of conditions that is permissive to cell division so as to increase the number of cells due to the presence of a fatty acid, cultivating the cell in an oil production phase under a second set of conditions that is restrictive to cell division but permissive to production of an oil that is enriched in C18, C20, C22 and/or C24 fatty acids. The cell can be cultivated heterotrophically. In some embodiments, the cell can be a microalgal cell and may produce at least 40%, 50%, 60%, 70%, 80%, or 90% oil by dry cell weight.

9. Oils with Non-Naturally Occurring Fatty Acid Profiles

Oils disclosed herein are distinct from other naturally occurring oils that are high in C18 long-chain fatty acids, including corn, peanut, cotton seed, apricot seed, mustard seed, neem, olive, palm, safflower, sesame, soybean and sunflower oils. For example, levels of contaminants such as carotenoids are far higher in corn, peanut, cotton seed, apricot seed, mustard seed, neem, olive, palm, safflower, sesame, soybean and sunflower oils than in the oils described herein. Plant oils in particular contain alpha and beta carotenes and lycopene in much higher amounts than are in the oils described herein. The oils described herein contain very few carotenoids species and very low levels. In addition, the levels of vitamin E compounds such as tocotrienols are far higher in plant oils than in the oils described herein.

In some cases, the oleaginous cells (e.g., *Prototheca* strains) containing a transgene encoding a variant KASII has a fatty acid profile characterized by at least about 40%, 45%, 50%, 55%, 60%, 65%, 70%, 75%, 80%, 85%, 90%, 95%, 97%, or more, C18, C20, C22, and/or C24 fatty acids. In other cases, the *Prototheca* strains containing a transgene encoding a variant KASII, has activity towards fatty acyl-ACP substrates of chain length C16 and produces fatty acids of the chain length C18 with a ratio of C18 to the sum of other fatty acids (e.g., C8+C10+C12+C14+C16+C20+C22+C24) of at least about 6.0, e.g., at least about 6.5, 7.0, 7.5, 8.0, 8.5, 9.0, 9.5, 10.0, 10.5, 11.0, 11.5, 12, 13, 14, 15, 16, 17, 18, 19, 20, 21, 22, 23, 24, 25, 26, 27, 28, 29, 30, 31, 32, or higher. The oleaginous cells can optionally co-express an exogenous lipid biosynthesis enzyme, e.g., a C18-preferring fatty acyl-ACP thioesterase, In some instances, keeping the transgenic *Prototheca* strains under constant and high selective pressure to retain exogenous genes is advantageous due to the increase in the desired fatty acid of a specific chain length. High levels of exogenous gene retention can also be achieved by inserting exogenous genes into the nuclear chromosomes of the cells using homologous recombination vectors and methods disclosed herein. Recombinant cells containing exogenous genes integrated into nuclear chromosomes are also contemplated.

Microalgal oil can also include other constituents produced by the microalgae, or incorporated into the microalgal oil from the culture medium. These other constituents can be present in varying amounts depending on the culture conditions used to culture the microalgae, the species of microalgae, the extraction method used to recover microalgal oil from the biomass and other factors that may affect microalgal oil composition. Non-limiting examples of such constituents include carotenoids, present from 0.1-0.4 micrograms/ml, chlorophyll present from 0-0.02 milligrams/kilogram of oil, gamma tocopherol present from 0.4-0.6 milligrams/100 grams of oil, and total tocotrienols present from 0.2-0.5 milligrams/gram of oil.

The other constituents can include, without limitation, phospholipids, tocopherols, tocotrienols, carotenoids (e.g., alpha-carotene, beta-carotene, lycopene, etc.), xanthophylls (e.g., lutein, zeaxanthin, alpha-cryptoxanthin and beta-cryptoxanthin), and various organic or inorganic compounds. Additionally, microalgal oils contain long-chain polyunsaturated fatty acids, particularly eicosapentaenoic (EPA).

Generally, higher carotenoid levels accumulate in algae grown photosynthetically than in algae grown heterotrophically. In some cases, the oil extracted from *Prototheca* species comprises no more than 0.02 mg/kg chlorophyll. In some cases, the oil extracted from *Prototheca* species comprises no more than 0.4 mcg/ml total carotenoids. In some cases the *Prototheca* oil comprises between 0.40-0.60 milligrams of gamma tocopherol per 100 grams of oil. In other cases, the *Prototheca* oil comprises between 0.2-0.5 milligrams of total tocotrienols per gram of oil.

Oils produced from host cells expressing a variant KASII, optionally co-expressing an exogenous lipid biosynthesis enzyme, e.g., a C18-preferring fatty acyl-ACP thioesterase, will have an isotopic profile that distinguishes it, e.g., from blended oils from other sources. The stable carbon isotope value $\delta 13C$ is an expression of the ratio of 13C/12C relative to a standard (e.g. PDB, carbonite of fossil skeleton of *Belemnite americana* from Peedee formation of South Carolina). The stable carbon isotope value $\delta 13C$ (0/00) of the oils can be related to the $\delta 13C$ value of the feedstock used. In some embodiments the oils are derived from oleaginous organisms heterotrophically grown on sugar derived from a C4 plant such as corn or sugarcane. In some embodiments, the $\delta 13C$ (0/00) of the oil is from 10 to −17 0/00 or from 13 to −16 0/00.

The oils produced according to the above methods in some cases are made using a microalgal host cell. As described above, the microalga can be, without limitation, fall in the classification of Chlorophyta, Trebouxiophyceae, Chlorellales, Chlorellaceae, or Chlorophyceae. Microalgae of Trebouxiophyceae can be distinguished from vegetable oils based on their sterol profiles. Oil produced by *Chlorella protothecoides* has been found to contain ergosterol and brassicasterols as major sterols. Both of these sterols feature C24β stereochemistry, in contrast to the C24α stereochemistry found in the majority of common plant sterols. Additional minor sterols present in *Chlorella* are also believed to primarily have C24β stereochemistry. Thus, the oils produced by the microalgae described above can be distinguished from plant oils by the preponderance of sterols with C24β stereochemistry in the sterols present. For example, the oils produced may contain 22, 23-dihydrobrassicasterol while lacking campesterol; contain clionasterol, while lacking in β-sitosterol, and/or contain poriferasterol while lacking stigmasterol. Alternately, or in addition, the oils may contain significant amounts of $\Delta^7$-poriferasterol. Accordingly, in some embodiments, the oils produced according to the methods described herein lack C24-α sterols.

In one embodiment, the oils provided herein are not vegetable oils. Vegetable oils are oils extracted from plants and plant seeds. Vegetable oils can be distinguished from the non-plant oils provided herein on the basis of their oil content. A variety of methods for analyzing the oil content can be employed to determine the source of the oil or whether adulteration of an oil provided herein with an oil of a different (e.g. plant) origin has occurred. The determination can be made on the basis of one or a combination of the analytical methods. These tests include but are not limited to analysis of one or more of free fatty acids, fatty acid profile, total triacylglycerol content, diacylglycerol content, peroxide values, spectroscopic properties (e.g. UV absorption), sterol profile, sterol degradation products, antioxidants (e.g. tocopherols), pigments (e.g. chlorophyll), d13C values and sensory analysis (e.g. taste, odor, and mouth feel). Many such tests have been standardized for commercial oils such as the *Codex Alimentarius* standards for edible fats and oils.

Sterol profile analysis is a particularly well-known method for determining the biological source of organic matter. Campesterol, β-sitosterol, and stigamsterol are common plant sterols, with β-sitosterol being a principle plant sterol. For example, β-sitosterol was found to be in greatest abundance in an analysis of certain seed oils, approximately 64% in corn, 29% in rapeseed, 64% in sunflower, 74% in cottonseed, 26% in soybean, and 79% in olive oil (Gul et al. J. Cell and Molecular Biology 5:71-79, 2006).

Oil isolated from *Prototheca moriformis* strain UTEX1435 were separately clarified (CL), refined and bleached (RB), or refined, bleached and deodorized (RBD) and were tested for sterol content according to the procedure described in JAOCS vol. 60, no. 8, August 1983. Results of the analysis are shown below (units in mg/100 g) in Table C:

TABLE C

| | Sterol | Crude | Clarified | Refined & bleached | Refined, bleached, & deodorized |
|---|---|---|---|---|---|
| 1 | Ergosterol | 384 (56%) | 398 (55%) | 293 (50%) | 302 (50%) |
| 2 | 5,22-cholestadien-24-methyl-3-ol (Brassicasterol) | 15 (2.1%) | 19 (2.6%) | 14 (2.4%) | 15 (2.5%) |
| 3 | Other sterols | 287 | 302 | 283 | 284 |
| | Total sterols | 686 | 719 | 590 | 601 |

These results show three striking features. First, ergosterol was found to be the most abundant of all the sterols, accounting for about 50% or more of the total sterols. Ergosterol is a sterol commonly found in fungus and not commonly found in plants, and its presence particularly in significant amounts serves as a useful marker for non-plant oils. Secondly, the oil was found to contain brassicasterol. In summary, *Prototheca moriformis* strain UTEX1435 has been found to contain both significant amounts of ergosterol and only trace amounts of β-sitosterol as a percentage of total sterol content. Accordingly, the ratio of ergosterol:β-sitosterol or in combination with the presence of brassicasterol can be used to distinguish this oil from plant oils.

In some embodiments, the oil content of an oil provided herein contains, as a percentage of total sterols, less than 20%, 15%, 10%, 5%, 4%, 3%, 2%, or 1% β-sitosterol. In other embodiments the oil is free from β-sitosterol.

In some embodiments, the oil is free from one or more of β-sitosterol, campesterol, or stigmasterol. In some embodiments the oil is free from β-sitosterol, campesterol, and stigmasterol. In some embodiments the oil is free from campesterol. In some embodiments the oil is free from stigmasterol.

In some embodiments, the oil content of an oil provided herein contains ergosterol or brassicasterol or a combination of the two. In some embodiments, the oil content contains, as a percentage of total sterols, at least 5%, 10%, 20%, 25%, 35%, 40%, 45%, 50%, 55%, 60%, or 65% ergosterol. In some embodiments, the oil content contains, as a percentage of total sterols, at least 25% ergosterol. In some embodiments, the oil content contains, as a percentage of total sterols, at least 40% ergosterol. In some embodiments, the oil content contains, as a percentage of total sterols, at least 5%, 10%, 20%, 25%, 35%, 40%, 45%, 50%, 55%, 60%, or 65% of a combination of ergosterol and brassicasterol.

In some embodiments, the oil content contains, as a percentage of total sterols, at least 1%, 2%, 3%, 4% or 5% brassicasterol. In some embodiments, the oil content contains, as a percentage of total sterols less than 10%, 9%, 8%, 7%, 6%, or 5% brassicasterol.

In some embodiments the ratio of ergosterol to brassicasterol is at least 5:1, 10:1, 15:1, or 20:1.

Sterols contain from 27 to 29 carbon atoms (C27 to C29) and are found in all eukaryotes. Animals exclusively make C27 sterols as they lack the ability to further modify the C27 sterols to produce C28 and C29 sterols. Plants however are able to synthesize C28 and C29 sterols, and C28/C29 plant sterols are often referred to as phytosterols. The sterol profile of a given plant is high in C29 sterols, and the primary sterols in plants are typically the C29 sterols β-sitosterol and stigmasterol. In contrast, the sterol profiles of non-plant organisms contain greater percentages of C27 and C28 sterols. For example the sterols in fungi and in many microalgae are principally C28 sterols. The sterol profile and particularly the striking predominance of C29 sterols over C28 sterols in plants has been exploited for determining the proportion of plant and marine matter in soil samples (Huang, Wen-Yen, Meinschein W. G., "Sterols as ecological indicators"; Geochimica et Cosmochimia Acta. Vol 43. pp 739-745).

In some embodiments the primary sterols in the microalgal oils provided herein are sterols other than β-sitosterol and stigmasterol. In some embodiments of the microalgal oils, C29 sterols make up less than 50%, 40%, 30%, 20%, 10%, or 5% by weight of the total sterol content.

In some embodiments the microalgal oils provided herein contain C28 sterols in excess of C29 sterols. In some embodiments of the microalgal oils, C28 sterols make up greater than 50%, 60%, 70%, 80%, 90%, or 95% by weight of the total sterol content. In some embodiments the C28 sterol is ergosterol. In some embodiments the C28 sterol is brassicasterol.

In some embodiments, oleaginous cells expressing one or more of the polynucleotides described herein can produce an oil with at least 40%, 45%, 50%, 55%, 60%, 65%, 70%, 75%, 80%, 85%, 90%, 95%, 97%, or more, C18, C20, C22, and/or C24 fatty acids.

In some embodiments, a recombinant cell comprises nucleic acids operable to express an exogenous gene encoding a variant KASII that catalyzes the elongation of C14 acyl-ACP or C16 acyl-ACP to long-chain fatty acids, optionally co-expressing an exogenous lipid biosynthesis enzyme, e.g., C18-preferring fatty acyl-ACP thioesterase. In some embodiments, the oil produced has a fatty acid profile that is elevated in C18, C20, C22, and/or C24 fatty acids and reduced in C8, C10, C12, C14 and/or C16 fatty acids as a result of the expression of the recombinant nucleic acids. In some embodiments, the increase in C18 (e.g., C18:0, C18:1, C18:2), C20, C22 and/or C24 fatty acids is greater than 1%, 2%, 3%, 4%, 5%, 6%, 7%, 8%, 9%, 10%, 20%, 30%, 40%, 50%, 60%, 70%, from 75-85%, from 70-90%, from 90-200%, from 200-300%, from 300-400%, from 400-500%, or greater than 500%. In some embodiments, the increase in C18, C20, C22, and/or C24 fatty acids is at least 2-fold, 3-fold, 4-fold, 5-fold, 6-fold, 7-fold, 8-fold, 9-fold, 10-fold, 11-fold, 12-fold, 13-fold, 14-fold, 15-fold, or more, in comparison to an untransformed microalga or a microalga transformed with a wild-type KASII enzyme.

The high long-chain oils or fatty acids derived from hydrolysis of these oils may be particularly useful in food, fuel and oleochemical applications including the production of lubricants and surfactants. For example, fatty acids derived from the cells can be esterified, cracked, reduced to an aldehyde or alcohol, aminated, sulfated, sulfonated, or subjected to other chemical process known in the art.

The following examples, which are offered to illustrate, but not to limit, the compositions and methods described herein.

EXAMPLES

The following examples are offered to illustrate, but not to limit the claimed invention.

Example 1

Improved Variants of *Prototheca moriformis* KAS II Enzyme

Random mutations were introduced into the wild-type PmKASII gene and the nucleotide sequence encoding the heterologous *Chlorella protothecoides* SAD1 transit peptide (CpSAD1tp) (SEQ ID NO: 4) via error-prone PCR (epPCR) using the commercially-available GeneMorph II Random Mutagenesis Kit (Agilent Technologies). Construct pSZ6014 (SEQ ID NO: 4) was used as the PCR template, while the oligonucleotides 5'-CGCGCGCAGGATAGACT-3' and 5'-AAACACCCACCTCCAACG-3' were used as the forward and reverse primers, respectively, for the mutagenesis reaction. The template concentration and the number of PCR cycles were adjusted to produce a library of variant genes containing an average of 4-5 mutations. This library was then subjected to gel purification using techniques familiar to those skilled in the art. The resulting isolated insert (~1.5-kb) was cloned into a pUC19-based vector (~8-kb) via SLIC, a sequence and ligase independent cloning technique familiar to those skilled in the art, at an insert to vector ratio of 20:1. This vector was obtained from the digestion of construct pSZ6014 with restriction enzymes, SpeI and PacI, followed by gel purification. Both the insert and vector share homologous sequences of approximately 40 bp at their 5' and 3' ends. The SLIC reaction was transformed into electrocompetent *Escherichia coli* cells, and the resulting transformants were grown on LB agar with 100 mg/L ampicillin for selection.

Quality control was performed on 20 randomly selected *E. coli* transformants via colony PCR and Sanger sequencing, techniques that are familiar to those skilled in the art, to confirm the mutagenized inserts they harbor exhibit high mutational diversity but with minimal frame-shift mutations. Plasmid DNA for the epPCR library was then prepared from an *E. coli* culture that was inoculated with approximately 16,000 transformants and grown in LB medium with 200 mg/L ampicillin for selection. This DNA was digested with the PmeI restriction enzyme to yield a ~6.6-kb fragment of interest for transformation into the *P. moriformis* high oleic base strain, S8758, via a suitable technique (as described in U.S. Pat. Nos. 8,846,352; 9,328,351 and 9,649,368). This fragment includes: 1) the 5' and 3' homology arms for targeted integration into the DAO1b locus of *P. moriformis*, 2) the PmSAD2-Iv3 promoter and the PmATP 3'-UTR for expression of the PmKASII variant genes, and 3) an expression cassette for the *S. cerevisiae* SUC2 gene to enable algal transformants to grow on medium containing sucrose as the sole carbon source. S8758 is a classically-improved derivative of the wild-type strain UTEX 1435, which was obtained from the University of Texas collection and was classically mutagenized to increase the oleic acid content of its oil.

Approximately 1,100 *P. moriformis* transformants were selected from agar plates containing growth medium (as detailed in U.S. Pat. Nos. 8,846,352; 9,328,351 and 9,649,368) with 20 g/L sucrose as the sole carbon source. These transformants were cultured individually in nitrogen-replete growth medium at pH 5 and 28° C. in microtiter plates until they reached mid-log phase. They were then pooled and used to inoculate 10-mL cultures containing nitrogen-replete growth medium that was supplemented with 80-120 µM cerulenin, a known inhibitor of KASII, to enrich for clones harboring PmKASII variants with increased activity. After approximately 40 h of growth at pH 5 and 28° C., the enrichment culture was plated for clonal isolation.

The resulting clones were grown at pH 5 and 28° C. for 3 or 5 days and screened under low-nitrogen conditions suitable for lipid production (as detailed in the Examples of PCT Patent Application WO 2018/067849). Those that consistently produced oils with a combined C14+C16 fatty acid content that was at least 3 standard deviations below the mean of the control strain S8786, which is also derived from strain S8758 but over-expresses one copy of the wild-type PmKASII gene, were considered as potential hits. Their PmKASII variant genes were PCR-amplified from their genomic DNA and subsequently sequenced to identify the causative mutations that led to their shift in lipid composition compared to strain S8786 using techniques familiar to those skilled in the art. Clones that harbored more than one PmKASII variant gene according to the sequencing data were eliminated from further evaluation.

The PmKASII variant gene (PmKASII$^{A162V}$) that conferred the greatest decrease in C14+C16 fatty acid content and increase in long-chain and very long-chain fatty acid content (C18+C20+C22+C24) contains two nucleotide mutations (SEQ ID NO: 5). One of them consists of a cytosine to thymine change at nucleotide position 485, which results in the replacement of an alanine to a valine at amino-acid position 162 of the encoded enzyme. The other, which consists of the cytosine to thymine change at nucleotide position 1080, is a silent mutation. To confirm the improved activity of the PmKASII$^{A162V}$ enzyme (SEQ ID NO: 2) in *P. moriformis*, the variant gene was re-cloned into the same expression vector that can be obtained through excision of construct pSZ6014 (as described above). The resulting construct pSZ6256 (SEQ ID NO: 3) was then re-transformed into strain S8758, and 12 clonally-purified transformants were selected for evaluation in 5-day lipid production cultures at pH 5 and 28° C. under low-nitrogen conditions. The transformants over-expressing one copy of the PmKASII$^{A162V}$ variant gene produced oils that on average showed a decrease in C14+C16 content from 3.9% to 2.8% and an increase in C18+C20+C22+C24 content from 95.3% to 96.9% compared to the control strain S8786, which over-expresses one copy of the wild-type PmKASII gene (Table 1). Despite the fact that a very low C14+C16 content can already be reached with the wild-type PmKASII (SEQ ID NO: 1), a further drop in C14+C16 content that is of statistical significance (t-test, p<0.01) was achieved with the PmKASII$^{A162V}$ variant. These results highlight the enhanced elongation activity of the PmKASII$^{A162V}$ variant and its utility for producing oils with reduced levels of C14 or C16 fatty acids and elevated levels of long-chain or very long-chain fatty acids.

TABLE 1

Comparison of Overexpression of PmKASII$^{A162V}$ and Wild-type PmKASII in *P. moriformis* strain S8758 on Oil Composition.*

| Strain/ Transformant | PmKASII | n | | C14:0 | C16:0 | C16:1 cis-7 | C16:1 cis-9 | C14 + C16 | C18:0 | C18:1 | C18:2 |
|---|---|---|---|---|---|---|---|---|---|---|---|
| S8758-pSZ6256 | A162V | 9 | Avg | 0.3 | 2.4 | 0.0 | 0.1 | 2.8 | 6.5 | 81.5 | 5.5 |
|  |  |  | Std Dev | — | 0.07 | — | — | 0.08 | 0.15 | 0.25 | 0.01 |
| S8786 (Control) | Wild-type | 3 | Avg | 0.5 | 3.2 | 0.0 | 0.1 | 3.9 | 5.6 | 82.3 | 5.9 |
|  |  |  | Std Dev | — | 0.01 | — | — | 0.01 | 0.04 | 0.04 | 0.05 |
| S8758 (High Oleic Base Strain) | None | 3 | Avg | 0.4 | 10.9 | 0.0 | 0.3 | 11.7 | 3.6 | 77.5 | 5.8 |
|  |  |  | Std Dev | — | 0.08 | — | — | 0.09 | 0.03 | 0.07 | 0.00 |

TABLE 1-continued

Comparison of Overexpression of PmKASII$^{A162V}$ and Wild-type PmKASII
in *P. moriformis* strain S8758 on Oil Composition.*

| Strain/ Transformant | PmKASII | n | | C18:3 α | C20:0 | C20:1 | C20:2 | C22:0 | C24:0 | C18 + C20 + C22 + C24 |
|---|---|---|---|---|---|---|---|---|---|---|
| S8758- pSZ6256 | A162V | 9 | Avg | 0.6 | 0.7 | 1.9 | 0.0 | 0.1 | 0.1 | 96.9 |
|  |  |  | Std Dev | — | — | 0.06 | — | — | — | 0.09 |
| S8786 (Control) | Wild- type | 3 | Avg | 0.6 | 0.4 | 0.3 | 0.0 | 0.1 | 0.1 | 95.3 |
|  |  |  | Std Dev | — | — | — | — | — | — | 0.01 |
| S8758 (High Oleic Base Strain) | None | 3 | Avg | 0.5 | 0.2 | 0.3 | 0.0 | 0.0 | 0.0 | 88.0 |
|  |  |  | Std Dev | — | — | — | — | — | — | 0.08 |

*All strains and transformants were tested in 5-day lipid production cultures at pH 5 and 28° C. under low-nitrogen conditions. Data for outlier transformants are not included.

Example 2

Saturation Mutagenesis at Amino Acid Residue 162 of the *Prototheca moriformis* KAS II Enzyme Example 1 demonstrated that overexpression of the wild-type PmKASII enzyme (SEQ NO ID: 1) can decrease the C14+C16 fatty acid content of the oil produced by *P. moriformis*, while increasing the long-chain and very long-chain fatty acid content (C18+C20+C22+C24). It also showed that an additional shift in oil composition toward long-chain and very long-chain fatty acids can be achieved by overexpressing a PmKASII enzyme variant that contains an Ala to Val mutation at amino acid residue 162 (SEQ NO ID: 2). In this example, results from saturation mutagenesis at position 162 of the PmKASII enzyme confirm the importance of this amino acid position in producing oils with elevated levels of long-chain (C18) and/or very long-chain (C20+C22+C24) fatty acids.

An expression construct that targets integration of the wild-type PmKASII gene (pSZ6014, SEQ NO ID: 12), the PmKASII$^{A162V}$ gene variant (pSZ7122, SEQ NO ID: 13), or the remaining eighteen PmKASII$^{A162X}$ gene variants (pSZ7104-pSZ7121, SEQ NO ID: 13) to the DAO1 locus in *P. moriformis* was transformed into the base strain S7485. These constructs also contain an expression cassette for the *S. cerevisiae* SUC2 (ScSUC2) gene, which enables growth of the resulting transformants on medium containing sucrose as the sole carbon source. Expression of the PmKASII$^{A162X}$ variants in the transgenic strains is driven by the constitutive PmSAD2-1 promoter. S7485 is a classically-improved derivative of the wild-type strain UTEX 1435, which was classically mutagenized to increase oil yield and productivity. The classical mutagenesis did not substantively alter the oleic acid content of the oil produced by S7485 when compared to UTEX 1435.

Clonally-purified transformants derived from strain S7485 and expressing a single copy of one of the PmKASII$^{A162X}$ variants (pSZ6014, pSZ7122, or pSZ7104-pSZ7121) were evaluated in 5-day lipid production cultures at pH 5 (as detailed in the Examples of PCT Patent Application WO 2018/067849) to determine their lipid profiles. The parental strain S7485 was also assessed as a control under the same conditions. The fatty acid profile of the oils produced by these transformants and strain are presented in Table 2. Compared to the parental strain S7485, the transformants expressing one additional copy of the wild-type PmKASII (pSZ6014) showed a prominent increase in C18+C20+C22+C24 fatty acid content from 65% to 84% with a concomitant decrease in C14+C16 fatty acid content from 35% to 16%. Overexpressing the A162V variant (pSZ7122) instead of the wild-type gene further increased the C18+C20+C22+C24 fatty acid content to 90%, while decreasing the C14+C16 fatty acid content to 10%. Likewise, overexpression of the A162N (pSZ7105), A162D (pSZ7106), A162Q (pSZ7108), A162H (pSZ7111), A162L (pSZ7113), A162F (pSZ7116), A162T (pSZ7119), or A162Y (pSZ7121) variant resulted in a similar shift in the fatty acid profile. The overexpression of many of the remaining variants—including A162C (pSZ7107), A162E (pSZ7109), A162K (pSZ7114), A162M (pSZ7115), A162S (pSZ7118), and A162W (pSZ7120)—also led to marked increases in the C18+C20+C22+C24 fatty acid content compared to the wild-type PmKASII with concomitant decreases in the C14+C16 fatty acid content, though the observed impact was less pronounced than that achieved with the A162V variant. Taken together, these results demonstrate the importance of position 162 of the PmKASII enzyme on the biosynthesis of triglycerides with elevated levels of long-chain and very long chain fatty acids (C18+C20+C22+C24).

Comparison of Overexpression of PmKASII$^{A162X}$ and Wild-type PmKASII
in *P. moriformis* strain S7485 on Oil Composition.*

| Strain/ Transformant | PmKASII | n | | C14:0 | C16:0 | C16:1 cis-7 | C16:1 cis-9 | C14 + C16 | C18:0 | C18:1 | C18:2 |
|---|---|---|---|---|---|---|---|---|---|---|---|
| S7485 | None | 4 | Avg | 1.9 | 32.2 | 0.0 | 0.8 | 34.8 | 3.8 | 55.2 | 4.8 |
|  |  |  | Std Dev | 0.00 | 0.08 | 0.01 | 0.02 | 0.09 | 0.01 | 0.01 | 0.03 |
| S7485- pSZ6014 | Wild- type | 4 | Avg | 2.0 | 13.4 | 0.1 | 0.3 | 15.7 | 6.0 | 71.6 | 5.1 |
|  |  |  | Std Dev | 0.01 | 0.08 | 0.01 | 0.01 | 0.08 | 0.02 | 0.12 | 0.05 |

Comparison of Overexpression of PmKASII^{A162X} and Wild-type PmKASII in *P. moriformis* strain S7485 on Oil Composition.*

| Strain/Transformant | PmKASII | n | | | | | | | | | |
|---|---|---|---|---|---|---|---|---|---|---|---|
| S7485-pSZ7122 | A162V | 5 | Avg | 1.1 | 8.3 | 0.1 | 0.2 | 9.6 | 7.1 | 76.4 | 5.1 |
| | | | Std Dev | 0.01 | 0.05 | 0.01 | 0.01 | 0.07 | 0.07 | 0.14 | 0.08 |
| S7485-pSZ7104 | A162R | 4 | Avg | 1.5 | 13.6 | 0.1 | 0.3 | 15.5 | 6.1 | 71.9 | 5.1 |
| | | | Std Dev | 0.02 | 0.21 | 0.02 | 0.01 | 0.22 | 0.09 | 0.25 | 0.07 |
| S7485-pSZ7105 | A162N | 4 | Avg | 1.3 | 9.0 | 0.1 | 0.2 | 10.5 | 7.2 | 75.4 | 5.1 |
| | | | Std Dev | 0.02 | 0.14 | 0.01 | 0.01 | 0.16 | 0.07 | 0.23 | 0.09 |
| S7485-pSZ7106 | A162D | 6 | Avg | 1.2 | 9.3 | 0.1 | 0.2 | 10.8 | 7.0 | 75.3 | 5.1 |
| | | | Std Dev | 0.03 | 0.21 | 0.00 | 0.00 | 0.24 | 0.12 | 0.39 | 0.06 |
| S7845-pSZ7107 | A612C | 6 | Avg | 1.6 | 12.1 | 0.1 | 0.2 | 13.9 | 6.2 | 73.2 | 5.1 |
| | | | Std Dev | 0.06 | 0.10 | 0.03 | 0.01 | 0.13 | 0.18 | 0.11 | 0.08 |
| S7845-pSZ7108 | A612Q | 6 | Avg | 1.2 | 8.1 | 0.1 | 0.2 | 9.6 | 7.0 | 76.7 | 5.0 |
| | | | Std Dev | 0.01 | 0.07 | 0.01 | 0.01 | 0.07 | 0.03 | 0.01 | 0.08 |
| S7845-pSZ7109 | A612E | 6 | Avg | 1.4 | 11.3 | 0.1 | 0.2 | 13.0 | 6.4 | 73.8 | 5.1 |
| | | | Std Dev | 0.02 | 0.12 | 0.01 | 0.01 | 0.15 | 0.10 | 0.16 | 0.05 |
| S7845-pSZ7110 | A612G | 6 | Avg | 2.1 | 14.8 | 0.1 | 0.3 | 17.3 | 5.7 | 70.4 | 5.1 |
| | | | Std Dev | 0.02 | 0.12 | 0.01 | 0.01 | 0.15 | 0.09 | 0.13 | 0.05 |
| S7845-pSZ7111 | A612H | 5 | Avg | 1.2 | 8.6 | 0.1 | 0.2 | 10.1 | 6.8 | 76.3 | 5.1 |
| | | | Std Dev | 0.02 | 0.13 | 0.01 | 0.01 | 0.16 | 0.13 | 0.35 | 0.10 |
| S7845-pSZ7112 | A612I | 8 | Avg | 1.9 | 13.2 | 0.1 | 0.3 | 15.5 | 5.9 | 72.0 | 5.1 |
| | | | Std Dev | 0.05 | 0.23 | 0.01 | 0.01 | 0.28 | 0.08 | 0.36 | 0.08 |
| S7845-pSZ7113 | A612L | 7 | Avg | 1.1 | 8.7 | 0.1 | 0.2 | 10.0 | 7.1 | 76.0 | 5.2 |
| | | | Std Dev | 0.01 | 0.12 | 0.01 | 0.01 | 0.12 | 0.12 | 0.20 | 0.13 |
| S7845-pSZ7114 | A612K | 6 | Avg | 1.3 | 10.0 | 0.1 | 0.2 | 11.6 | 6.7 | 74.9 | 5.1 |
| | | | Std Dev | 0.02 | 0.13 | 0.01 | 0.01 | 0.16 | 0.03 | 0.17 | 0.03 |
| S7845-pSZ7115 | A612M | 8 | Avg | 1.3 | 11.1 | 0.1 | 0.2 | 12.7 | 6.4 | 74.2 | 5.1 |
| | | | Std Dev | 0.04 | 0.51 | 0.01 | 0.03 | 0.52 | 0.24 | 0.53 | 0.09 |
| S7845-pSZ7116 | A612F | 7 | Avg | 1.1 | 7.9 | 0.1 | 0.2 | 9.3 | 7.0 | 76.9 | 5.1 |
| | | | Std Dev | 0.02 | 0.08 | 0.01 | 0.00 | 0.09 | 0.05 | 0.14 | 0.04 |
| S7845-pSZ7117 | A612P | 8 | Avg | 1.9 | 13.1 | 0.1 | 0.3 | 15.4 | 6.0 | 72.0 | 5.1 |
| | | | Std Dev | 0.03 | 0.10 | 0.01 | 0.01 | 0.11 | 0.10 | 0.26 | 0.03 |
| S7845-pSZ7118 | A612S | 6 | Avg | 1.5 | 10.3 | 0.1 | 0.2 | 12.2 | 6.5 | 74.5 | 5.2 |
| | | | Std Dev | 0.03 | 0.16 | 0.01 | 0.01 | 0.20 | 0.12 | 0.08 | 0.04 |
| S7845-pSZ7119 | A612T | 7 | Avg | 1.1 | 7.3 | 0.1 | 0.1 | 8.7 | 7.3 | 77.0 | 5.2 |
| | | | Std Dev | 0.04 | 0.36 | 0.01 | 0.01 | 0.40 | 0.13 | 0.33 | 0.07 |
| S7845-pSZ7120 | A612W | 6 | Avg | 1.3 | 10.8 | 0.1 | 0.2 | 12.3 | 6.4 | 74.5 | 5.1 |
| | | | Std Dev | 0.03 | 0.13 | 0.01 | 0.01 | 0.15 | 0.04 | 0.19 | 0.06 |
| S7845-pSZ7121 | A612Y | 8 | Avg | 1.1 | 7.7 | 0.1 | 0.2 | 9.1 | 6.9 | 77.2 | 5.1 |
| | | | Std Dev | 0.03 | 0.14 | 0.01 | 0.01 | 0.19 | 0.22 | 0.30 | 0.11 |

| Strain/Transformant | PmKASII | n | | Fatty Acid Profile (%) | | | | | | |
|---|---|---|---|---|---|---|---|---|---|---|
| | | | | C18:3 α | C20:0 | C20:1 | C20:2 | C22:0 | C24:0 | C18 + C20 + C22 + C24 |
| S7485 | None | 4 | Avg | 0.4 | 0.3 | 0.0 | 0.0 | 0.1 | 0.0 | 64.6 |
| | | | Std Dev | 0.01 | 0.01 | 0.02 | 0.00 | 0.01 | 0.00 | 0.09 |
| S7485-pSZ6014 | Wild-type | 4 | Avg | 0.4 | 0.4 | 0.1 | 0.0 | 0.1 | 0.0 | 83.7 |
| | | | Std Dev | 0.01 | 0.01 | 0.10 | 0.00 | 0.01 | 0.00 | 0.12 |
| S7485-pSZ7122 | A162V | 5 | Avg | 0.4 | 0.5 | 0.1 | 0.0 | 0.1 | 0.0 | 89.6 |
| | | | Std Dev | 0.01 | 0.01 | 0.17 | 0.00 | 0.01 | 0.00 | 0.13 |
| S7485-pSZ7104 | A162R | 4 | Avg | 0.4 | 0.4 | 0.1 | 0.0 | 0.1 | 0.0 | 84.0 |
| | | | Std Dev | 0.01 | 0.01 | 0.10 | 0.00 | 0.01 | 0.00 | 0.28 |

Comparison of Overexpression of PmKASII$^{A162X}$ and Wild-type PmKASII in *P. moriformis* strain S7485 on Oil Composition.*

| Strain | Mutation | n | Stat | | | | | | | |
|---|---|---|---|---|---|---|---|---|---|---|
| S7485-pSZ7105 | A162N | 4 | Avg | 0.4 | 0.5 | 0.2 | 0.0 | 0.1 | 0.0 | 88.9 |
| | | | Std Dev | 0.01 | 0.01 | 0.14 | 0.00 | 0.01 | 0.00 | 0.22 |
| S7485-pSZ7106 | A162D | 6 | Avg | 0.4 | 0.5 | 0.1 | 0.0 | 0.1 | 0.0 | 88.5 |
| | | | Std Dev | 0.01 | 0.01 | 0.18 | 0.00 | 0.01 | 0.00 | 0.21 |
| S7845-pSZ7107 | A612C | 6 | Avg | 0.4 | 0.4 | 0.0 | 0.0 | 0.1 | 0.0 | 85.4 |
| | | | Std Dev | 0.02 | 0.03 | 0.07 | 0.00 | 0.01 | 0.00 | 0.17 |
| S7845-pSZ7108 | A612Q | 6 | Avg | 0.4 | 0.5 | 0.3 | 0.0 | 0.1 | 0.0 | 89.9 |
| | | | Std Dev | 0.02 | 0.01 | 0.13 | 0.00 | 0.01 | 0.00 | 0.17 |
| S7845-pSZ7109 | A612E | 6 | Avg | 0.4 | 0.5 | 0.1 | 0.0 | 0.1 | 0.0 | 86.4 |
| | | | Std Dev | 0.01 | 0.01 | 0.17 | 0.00 | 0.01 | 0.00 | 0.12 |
| S7845-pSZ7110 | A612G | 6 | Avg | 0.4 | 0.4 | 0.0 | 0.0 | 0.1 | 0.0 | 82.0 |
| | | | Std Dev | 0.01 | 0.02 | 0.07 | 0.00 | 0.01 | 0.00 | 0.22 |
| S7845-pSZ7111 | A612H | 5 | Avg | 0.4 | 0.5 | 0.1 | 0.0 | 0.1 | 0.0 | 89.2 |
| | | | Std Dev | 0.01 | 0.01 | 0.15 | 0.00 | 0.01 | 0.00 | 0.24 |
| S7845-pSZ7112 | A612I | 8 | Avg | 0.4 | 0.4 | 0.0 | 0.0 | 0.1 | 0.0 | 83.9 |
| | | | Std Dev | 0.01 | 0.01 | 0.04 | 0.00 | 0.01 | 0.00 | 0.29 |
| S7845-pSZ7113 | A612L | 7 | Avg | 0.4 | 0.5 | 0.1 | 0.0 | 0.1 | 0.0 | 89.3 |
| | | | Std Dev | 0.01 | 0.02 | 0.17 | 0.00 | 0.01 | 0.00 | 0.21 |
| S7845-pSZ7114 | A612K | 6 | Avg | 0.4 | 0.5 | 0.0 | 0.0 | 0.1 | 0.0 | 87.7 |
| | | | Std Dev | 0.01 | 0.01 | 0.10 | 0.00 | 0.01 | 0.00 | 0.17 |
| S7845-pSZ7115 | A612M | 8 | Avg | 0.4 | 0.4 | 0.1 | 0.0 | 0.1 | 0.0 | 86.6 |
| | | | Std Dev | 0.01 | 0.01 | 0.10 | 0.00 | 0.01 | 0.00 | 0.47 |
| S7845-pSZ7116 | A612F | 7 | Avg | 0.4 | 0.5 | 0.2 | 0.0 | 0.1 | 0.0 | 90.2 |
| | | | Std Dev | 0.01 | 0.01 | 0.14 | 0.00 | 0.01 | 0.00 | 0.16 |
| S7845-pSZ7117 | A612P | 8 | Avg | 0.4 | 0.4 | 0.1 | 0.0 | 0.1 | 0.0 | 84.0 |
| | | | Std Dev | 0.01 | 0.02 | 0.07 | 0.00 | 0.01 | 0.00 | 0.16 |
| S7845-pSZ7118 | A612S | 6 | Avg | 0.4 | 0.5 | 0.1 | 0.0 | 0.1 | 0.0 | 87.1 |
| | | | Std Dev | 0.01 | 0.02 | 0.12 | 0.00 | 0.01 | 0.00 | 0.28 |
| S7845-pSZ7119 | A612T | 7 | Avg | 0.4 | 0.5 | 0.0 | 0.0 | 0.1 | 0.0 | 90.5 |
| | | | Std Dev | 0.01 | 0.03 | 0.00 | 0.00 | 0.01 | 0.00 | 0.37 |
| S7845-pSZ7120 | A612W | 6 | Avg | 0.4 | 0.4 | 0.0 | 0.0 | 0.1 | 0.0 | 87.0 |
| | | | Std Dev | 0.01 | 0.02 | 0.09 | 0.00 | 0.01 | 0.00 | 0.14 |
| S7845-pSZ7121 | A612Y | 8 | Avg | 0.4 | 0.5 | 0.0 | 0.0 | 0.1 | 0.0 | 90.2 |
| | | | Std Dev | 0.01 | 0.02 | 0.11 | 0.00 | 0.01 | 0.00 | 0.16 |

*The parental strain S7485 was transformed with construct pSZ6014, pSZ7122, or pSZ7104-pSZ7121 (Table 3). Each of these constructs expresses either the wild-type PmKASII or one of the enzyme variants containing an amino acid substitution at position 162. All clonally-purified transformants were tested in five-day lipid production cultures at pH 5 under low nitrogen conditions. Data for outlier transformants are not included. Fatty acid profiles of oils produced by single integrants of the PmKASII gene are shown. The highlighted variants represent the amino acid substitutions that confer the greatest increase in long-chain and very long-chain fatty acid content (C18 + C20 + C22 + C24). n = total of replicates or transformants tested.

TABLE 3

Codons used to encode specific amino acids in various expression constructs.

| Construct | Amino Acid | Codon |
|---|---|---|
| pSZ7104 | Arg | CGC |
| pSZ7105 | Asn | AAC |
| pSZ7106 | Asp | GAC |
| pSZ7107 | Cys | TGC |
| pSZ7108 | Gln | CAG |
| pSZ7109 | Glu | GAG |
| pSZ7110 | Gly | GGC |
| pSZ7111 | His | CAC |
| pSZ7112 | Ile | ATC |
| pSZ7113 | Leu | CTG |
| pSZ7114 | Lys | AAG |
| pSZ7115 | Met | ATG |
| pSZ7116 | Phe | TTC |
| pSZ7117 | Pro | CCG |
| pSZ7118 | Ser | AGC |
| pSZ7119 | Thr | ACG |
| pSZ7120 | Trp | TGG |
| pSZ7121 | Tyr | TAC |
| pSZ7122 | Val | GTC |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A polynucleotide encoding a non-natural variant β-ketoacyl-acyl carrier protein (ACP) synthase (KAS) II enzyme (KASII), wherein the non-natural KASII comprises at least about 80%, 85%, 90%, 91%, 92%, 93%, 94%, 95%, 96%, 97%, 98% or 99% sequence identity to amino acid residues 39-469 of SEQ ID NO:2 and comprises an X at the position corresponding to position 162; wherein X is an amino acid residue selected from the group consisting of cysteine (C), aspartate (D), glutamate (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W) and tyrosine (Y), wherein the positions are with reference to SEQ ID NO:2, and wherein the non-natural KASII catalyzes the elongation of C14 acyl-ACP to C16 acyl-ACP or C16 acyl-ACP to C18 acyl-ACP.

2. The polynucleotide of claim 1, wherein the non-natural KASII preferentially produces C18 acyl-ACP, or wherein the non-natural KASII facilitates the production of increased levels of C18, C20, C22, and/or C24 fatty acids in comparison to a wild-type KASII having SEQ ID NO: 1, or wherein the non-natural KASII facilitates the production of an increased level of C18:1 fatty acid in comparison to a wild-type KASII having SEQ ID NO: 1, and/or wherein the non-natural KASII facilitates a decreased level of C16:0 in comparison to a wild-type KASII having SEQ ID NO: 1.

3. The polynucleotide of claim 1, wherein the X at position 162 is an amino acid residue selected from cysteine (C), glutamate (E), lysine (K), methionine (M), serine (S), tryptophan (W), valine (V), asparagine (N), aspartate (D), glutamine (Q), histidine (H), leucine (L), phenylalanine (F), threonine (T), and tyrosine (Y).

4. A host cell comprising the polynucleotide of claim 3, further comprising a polynucleotide encoding a fatty acyl-ACP thioesterase.

5. A method of producing triglyceride lipids comprising predominantly C18, C20, C22, and/or C24 fatty acids, comprising cultivating a microalgal host cell comprising:
   (a) a polynucleotide encoding a fatty acyl-ACP thioesterase; and
   (b) the polynucleotide of claim 3,
   so as to produce triglyceride lipids comprising at least about 40% C18, C20, C22, and/or C24 fatty acids, or optionally at least about 45%, 50%, 55%, 60%, 65%, 70%, 75%, 80%, 85%, 90%, 95%, 97%, or more, C18, C20, C22, and/or C24 fatty acids.

6. The polynucleotide of claim 1, wherein the X at position 162 is an amino acid selected from valine (V), asparagine (N), aspartate (D), glutamine (Q), histidine (H), leucine (L), phenylalanine (F), threonine (T), and tyrosine (Y).

7. A host cell comprising the polynucleotide of claim 6, further comprising a polynucleotide encoding a fatty acyl-ACP thioesterase.

8. A method of producing triglyceride lipids comprising predominantly C18, C20, C22, and/or C24 fatty acids, comprising cultivating a microalgal host cell comprising:
   (a) a polynucleotide encoding a fatty acyl-ACP thioesterase; and
   (b) the polynucleotide of claim 6,
   so as to produce triglyceride lipids comprising at least about 40% C18, C20, C22, and/or C24 fatty acids, or optionally at least about 45%, 50%, 55%, 60%, 65%, 70%, 75%, 80%, 85%, 90%, 95%, 97%, or more, C18, C20, C22, and/or C24 fatty acids.

9. The polynucleotide of claim 1, wherein the non-natural or variant KASII comprises a plastid transit peptide.

10. The polynucleotide of claim 9, wherein the plastid transit peptide comprises at least about 80%, 85%, 90%, 91%, 92%, 93%, 94%, 95%, 96%, 97%, 98% or 99% identity to SEQ ID NO:7, SEQ ID NO:8, SEQ ID NO:9 or SEQ ID NO:10.

11. The polynucleotide of claim 1, comprising at least about 80%, 85%, 90%, 91%, 92%, 93%, 94%, 95%, 96%, 97%, 98% or 99% identity to:
   a) nucleic acid residues 115-1407 of SEQ ID NO:6;
   b) nucleic acid residues 1-1407 of SEQ ID NO:6; or,
   c) SEQ ID NO:6.

12. The polynucleotide of claim 11, wherein the polynucleotide comprises a thymine (T) at residue position 1080.

13. The polynucleotide of claim 1, comprising codon bias for improved expression in a microalgal host cell, optionally in a *Prototheca* or *Chlorella* microalgal host cell.

14. A host cell comprising the polynucleotide of claim 1, further comprising a polynucleotide encoding a fatty acyl-ACP thioesterase.

15. The host cell of claim 14, wherein the thioesterase preferentially hydrolyzes C18 acyl-ACP substrates.

16. The host cell of claim 14, wherein the thioesterase preferentially hydrolyzes C18:0 acyl-ACP, C18:1 acyl-ACP or C18:2 acyl-ACP substrates.

17. The host cell of claim 14, wherein the thioesterase is from a plant genus selected from *Brassica, Carthamus, Camelina, Garcinia, Glycine, Mangifera, Helianthus, Madhura, Arachis, Monts, Ricinus, Herrania, Corchorus, Corchorus, Jatropha, Ziziphus, Trema orientalis, Hevea, Theobroma, Quercus, Cucurbita, Dorcoceras, Rosa, Asparagus, Cephalotus, Parasponia, Carica, Arabidopsis, Capsella* and *Eutrema*.

18. The host cell of claim 14, wherein the polynucleotide encodes a *Garcinia mangostana* (GmFATA) thioesterase, optionally comprising one or more amino acid substitutions selected from the group consisting of L91F, L91K, L91S, G96A, G96T, G96V, G108A, G108V, S111A, S111V, T156F, T156A, T156K, T156V and V193A, wherein the amino acid positions are with reference to SEQ ID NO:11.

19. The host cell of claim 14, wherein the host cell is a microalga cell of the genus *Prototheca* or *Chlorella*.

20. The host cell of claim 19, wherein the microalga cell is selected from the group consisting of *Prototheca moriformis, Prototheca krugani, Prototheca stagnora, Prototheca zopfii* and *Chlorella protothecoides*.

21. A method of producing triglyceride lipids comprising predominantly C18, C20, C22, and/or C24 fatty acids, comprising cultivating a microalgal host cell comprising the polynucleotide of claim 1 so as to produce triglyceride lipids comprising at least about 40% C18, C20, C22, and/or C24 fatty acids, or optionally at least about 45%, 50%, 55%, 60%, 65%, 70%, 75%, 80%, 85%, 90%, 95%, 97%, or more, C18, C20, C22, and/or C24 fatty acids.

22. A method of producing triglyceride lipids comprising predominantly C18, C20, C22, and/or C24 fatty acids, comprising cultivating a microalgal host cell comprising:
   (a) a polynucleotide encoding a fatty acyl-ACP thioesterase; and
   (b) the polynucleotide of claim 1,
   so as to produce triglyceride lipids comprising at least about 40% C18, C20, C22, and/or C24 fatty acids, or optionally at least about 45%, 50%, 55%, 60%, 65%, 70%, 75%, 80%, 85%, 90%, 95%, 97%, or more, C18, C20, C22, and/or C24 fatty acids.

* * * * *

UNITED STATES PATENT AND TRADEMARK OFFICE
CERTIFICATE OF CORRECTION

PATENT NO. : 11,618,890 B2  
APPLICATION NO. : 17/270141  
DATED : April 4, 2023  
INVENTOR(S) : Nien-Hsi Ko et al.

Page 1 of 1

It is certified that error appears in the above-identified patent and that said Letters Patent is hereby corrected as shown below:

In the Claims

In Column 80, Claim 17, Line 15, please replace "*Monts*" with "*Morus*".

Signed and Sealed this  
Sixth Day of June, 2023

Katherine Kelly Vidal  
*Director of the United States Patent and Trademark Office*